(12) United States Patent
Roux et al.

(10) Patent No.: US 7,923,216 B2
(45) Date of Patent: Apr. 12, 2011

(54) IN VIVO MODULATION OF NEURONAL TRANSPORT

(75) Inventors: Sylvie Roux, Paris (FR); Philippe Brulet, Paris (FR); Cécile Saint Cloment, Paris (FR); Julien Barbier, Paris (FR); Jordi Molgo, Paris (FR)

(73) Assignees: Institut Pasteur, Paris (FR); Centre Nationale de la Recherche Scientifique, Paris (FR)

( * ) Notice: Subject to any disclaimer, the term of this patent is extended or adjusted under 35 U.S.C. 154(b) by 1401 days.

(21) Appl. No.: 10/662,808

(22) Filed: Sep. 16, 2003

(65) Prior Publication Data

US 2004/0170651 A1 Sep. 2, 2004

Related U.S. Application Data

(63) Continuation-in-part of application No. 09/816,467, filed on Mar. 26, 2001, which is a continuation of application No. 09/129,368, filed on Aug. 5, 1998, now abandoned.

(60) Provisional application No. 60/055,615, filed on Aug. 14, 1997, provisional application No. 60/065,236, filed on Nov. 13, 1997.

(51) Int. Cl.
*G01N 33/53* (2006.01)
*G01N 33/567* (2006.01)
*C07K 1/00* (2006.01)
*C07K 14/00* (2006.01)
*A61K 38/24* (2006.01)

(52) U.S. Cl. ............ 435/7.8; 435/7.1; 435/7.2; 530/350; 530/399

(58) Field of Classification Search .................. 530/350, 530/399; 435/7.1, 7.2, 7.8
See application file for complete search history.

(56) References Cited

U.S. PATENT DOCUMENTS

| | | | |
|---|---|---|---|
| 4,479,940 | A | 10/1984 | Bizzini |
| 4,594,336 | A | 6/1986 | Bizzini |
| 5,004,683 | A | 4/1991 | Erichsen et al. |
| 5,082,670 | A | 1/1992 | Gage et al. |
| 5,443,966 | A | 8/1995 | Fairweather et al. |
| 5,580,859 | A | 12/1996 | Felgner et al. |
| 5,589,466 | A | 12/1996 | Felgner et al. |
| 5,643,578 | A | 7/1997 | Robinson et al. |
| 5,728,383 | A | 3/1998 | Johnson et al. |
| 5,728,399 | A | 3/1998 | Wu et al. |
| 5,762,926 | A | 6/1998 | Gage et al. |
| 5,766,948 | A | 6/1998 | Gage et al. |
| 5,780,024 | A | 7/1998 | Brown et al. |
| 5,840,540 | A | 11/1998 | George-Hyslop et al. |
| 6,005,004 | A | 12/1999 | Katz et al. |
| 6,159,948 | A | 12/2000 | Robertson et al. |
| 2003/0004121 | A1 | 1/2003 | Coen et al. |
| 2003/0083299 | A1 | 5/2003 | Ferguson |
| 2004/0170651 | A1 | 9/2004 | Roux et al. |
| 2005/0060761 | A1 | 3/2005 | Vazquez-Martinez et al. |
| 2007/0092449 | A1 | 4/2007 | Vazquez-Martinez et al. |

FOREIGN PATENT DOCUMENTS

| | | |
|---|---|---|
| CA | 1152493 | 8/1983 |
| CA | 1178949 | 12/1984 |
| EP | 0 030 496 | 6/1981 |
| WO | WO 95/04151 A2 | 2/1995 |
| WO | WO 97/07668 | 8/1996 |
| WO | WO 99/09057 | 2/1999 |
| WO | WO 01/52843 A | 7/2001 |
| WO | WO 01/58936 A2 | 8/2001 |

OTHER PUBLICATIONS

Davis, C. G., 1990, The New Biologist, vol. 2, No. 5, p. 410-419.*
Skolnick et al., 2000, Trends in Biotech, vol. 18, p. 34-39.*
Miana-Mena et al., 2002, PNAS, vol. 99, No. 5, p. 3234-3239.*
Poo, M-M., 2001, Nature Review, Neuroscience, vol. 2, p. 24-32.*
Stoop et al., 1996, The Journal of Neuroscience, vol. 16, No. 10, p. 3256-3264.*
Erdmann et al., "Intraaxonal and Extraaxonal Transport of $^{125}$I-Tetanus Toxin in Early Local Tetanus," *Naunyn-Schmiedeberg's Arch. Pharmacol*, 290, pp. 357-373 (1975).
Price et al., "Tetanus Toxin: Direct Evidence for Retrograde Intraaxonal Transport," *Science*, vol. 188, pp. 945-947 (1975).
Stockel et al., "Comparison Between the Retrograde Axonal Transport of Nerve Growth Factor and Tetanus Toxin in Motor, Sensory and Adrenergic Neurons," *Brain Research*, 99, pp. 1-16 (1975).
Schwab et al., "Electron Microscopic Evidence for a Transsynaptic Migration of Tetanus Toxin in Spinal Cord Motoneurons: An Autoradiographic and Morphometric Study," *Brain Research*, 105, pp. 213-227 (1976). Helting et al., "Structure of Tetanus Toxin," *The Journal of Biological Chemistry*, 252, (1), pp. 187-193 (1977).
Eisel et al., "Tetanus Toxin: Primary Structure, Expression in *E. coli*, and Homology with Botulinum Toxins," *The EMBO Journal*, 5, (10), pp. 2495-2502 (1986).
Francis et al., "CuZn Superoxide Dismutase (SOD-1): Tetanus Toxin Fragment C Hybrid Protein for Targeted Delivery of SOD-1 to Neuronal Cells," *The Journal of Biological Chemistry*, 270, (25), pp. 15434-15442 (1995).
Kuypers et al., "Viruses as Transneuronal Tracers," *TINS*, 13, (2), pp. 71-75 (1990).
Figueiredo et al., "Delivery of Recombinant Tetanus-Superoxide Dismutase Proteins to Central Nervous System Neurons by Retrograde Axonal Transport," *Experimental Neurology*, 145, pp. 546-554 (1997).

(Continued)

*Primary Examiner* — Shin-Lin Chen
(74) *Attorney, Agent, or Firm* — Finnegan, Henderson, Farabow, Garrett & Dunner LLP

(57) ABSTRACT

A hybrid protein (GFP-TTC) comprising the non-toxic proteolytic C fragment of tetanus toxin fused to green fluorescent protein was used to analyze the functional synaptic organization of neural networks. When injected intramuscularly in vivo, the GFP-TTC hybrid protein binds to tetanus neurotoxin receptors and clusters very rapidly to the active neuromuscular junction. Membrane traffic by GFP-TTC at the pre-synaptic level of the neuromuscular junction is strongly and rapidly influenced by exogenously co-injecting neurotrophic factors, such as BDNF, NT-4, and GDNF, but not by NGF, NT-3, and CNTF. The membrane traffic, directly detected using GFP-TTC in vivo, permits methods of analyzing synaptic functioning as well as methods of modulating neuronal transport using neurotrophic factors and agonists or antagonists thereof.

14 Claims, 24 Drawing Sheets

OTHER PUBLICATIONS

Beaude et al., "Retrograde Axonal Transport of an Exogenous Enzyme Covalently Linked to B-II$_b$ Fragment of Tetanus Toxin," *Biochem. J.*, 271, pp. 87-91 (1990).

Fishman et al., "Enhanced CNS Uptake of Systemically Administered Proteins Through Conjunction with Tetanus C-fragment," *Journal of the Neurological Sciences*, 98, pp. 311-325 (1990).

Orkin et al., *Recommendations of the Panel to Assess the NIH Investment in Research on Gene Therapy* (Dec. 1995).

Montecucco et al., "Structure and Function of Tetanus and Botulinum Nerotoxins," *Quarterly Reviews of Biophysics*, 28 pp. 423-472 (1995).

Hazinski et al., *Am. J. Respir. Cell Mol. Biol.*, vol. 4(3), pp. 206-209 (1991).

P. Boucher et al., "Neutralizing Antibodies and Immunoprotection Against Pertussis and Tetanus Obtained by Use of a Recombinant Pertussis Toxin-Tetanus Toxin Fusion Protein," *Infection and Immunity*, vol. 62, No. 2, pp. 449-456 (1994).

J. Francis et al., "CuZn Superoxide Dismutase (SOD-1):Tetanus Toxin Fragment C Hybrid Protein for Targeted Delivery of SOD-1 to Neuronal Cells," *J. Biological Chemistry*, vol. 270, No. 25, pp. 15434-15442 (Jun. 23, 1995).

N. Fairweather et al., "Immunization of Mice Against Tetanus With Fragments of Tetanus Toxin Synthesized in *Escherichia coli*," *Infection and Immunity*, vol. 55, No. 11, pp. 2541-2545 (Nov. 1987).

P. Liston et al., "Suppression of Apoptosis in Mammalian Cells by NAIP and a Related Family of IAP Genes," *Nature*, vol. 379, pp. 349-353 (Jan. 25, 1996).

G.P. Mueller, ARO-27890.1-LS, Order No. AD-A290 501, NTIS, p. 1-15 (1994).

Hohne-Zell et al., *FEBS Letters*, vol. 336, No. 1, p. 175-180 (1993).

J. Rudinger, "Peptide Hormones", edited by Parsons, J., University Park Press, Baltimore, p. 1-7 (1976).

Kaye et al. *PNAS, USA*, vol. 87, pp. 6922-6926 (1990).

Bordet, et al., Mol. Cell. Neurosci., vol. 17, pp. 842-854 (2001).

Lalli, et al. J. Cell Biol. vol. 156, pp. 233-239 (2002).

International Search Report for PCT/EP2004/010991.

Bartheld, C. S. von, et al., "Anterograde Axonal Transport, Transcytosis, and Recycling of Neurotrophic Factors", Mol. Neruobiol. 24:1-28 (2001).

Bendig et al., "Differential Expression of the *Xenopus laevis* Tadpole and Adult β-Globin When Injected into Fertilized *Xenopus laevis* Eggs", MCB 4:567-570 (1984).

Bendig et al., "Replication and expression of *Xenopus laevis* globin into fertilized *Xenopus* eggs", PNAS 80:6197-6201 (1983).

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J of Cell Bio. 111:2129-2138, (1990).

Bürki et al., "Transplantation of the human insulin gene into fertilized mouse eggs", EMBO 1:127-131 (1982).

Chanock et al., "Immunization by Selective Infection With Type 4 Adenovirus Grown in Human Diploid Tissue Culture", JAMA, 195:151-158 (1966).

Chen et al., Molecular Brightness Characterization of EGFP in vivo by Fluorescence Fluctuation Spectroscopy, *Biophysical Journal*, vol. 82, pp. 133-144 (Jan. 2002).

U.S. Appl. No. 09/915,467, filed Jan. 2, 2003, Coen et al.

Chudakov et al., Use of Green Fluorescent Protein (GFP) and its Homologs for in vivo Protein Motility Studies, *Biochemistry*, Abstract (Sep. 2003).

Coen et al., "A somatic gene transfer approach using recombinant fusion proteins to map muscle-motoneuron projections in Xenopus spinal cord", Int. J. Dev. Biol., vol. 43, p. 823-830 (1999).

Coen, et al., "Construction of hybrid proteins that migrate retrogradely and transsynaptically into the central nervous system", Proc. Natl..Acad. Sci., USA, National Academy of Sciences, Washington, DC, vol. 94, pp. 9400-9405 (Aug. 1997).

Cohen et al., Inducible transcription and puffing in *Drosophila melanogaster* transformed with *hsp70*-phage λ hybrid heat shock genes, PNAS 81:5509-13 (1984).

Database EMBL, EBI, XP002377205, Database accession No. EM_PRO:AF528097, p. 1, (Feb. 5, 2003).

Database EMBL, EBI, XP002377211, Datbase accession No. EM PRO:AE005174 abstract; sequence AE005174, pp. 1-11, (Dec. 8, 2004).

Eck et al., Goodman & Gilman's The Pharmacological Basis of Therapeutics, McGraw-Hill, New York, p. 77-101 (1996).

Fishman et al., "Protein Delivery to Neurons Tetanus Toxin Compared to its Ganglioside Binding Fragment (Fragment C)", Society for Neuroscience Abstracts, vol. 22, pp. 1705 (1996).

Fox et al., "DNA-Induced Transformation in *Drosophila*: Genetic Analysis of Transformed Stocks", PNAS 68:342-346 (1971).

Gehring et al., "Functional analysis of the *white*+gene of *Drosophila* by P-factor-mediated transformation", EMBO 3:2077-85 (1984).

Gordon et al., "Gene Transfer into Mouse Embroys : Production of Transgenic Mice by Pronuclear Injection", Methods in Enzymology 101:411-433 (1983).

Gordon et al., Genetic transformation of mouse embroys by microinjection of purified DNA , PNAS 77 :7380-84 (1980).

Gorecki, "Prospects and problems of gene therapy: an update", Expert Opin. Emerging Drugs, 6(2): 187-198 (2001).

Halpern and Loftus, "Characterization of the Receptor-binding Domain of Tetanus Toxin", J. Biol. Chem., vol. 268, pp. 11188-11192 (1993).

Halpern, et al., "Cloning and expression of functional fragment C of tetanus toxin," J. Infect. Immun.., vol. 58, pp. 1004-1009 (1990).

Hoffman, R.M. Visualization of GFP-expressing Tumors and Metastasis in vivo, *Biotechniques*, May 2001, Abstract.

International Search Report for PCT/EP2005/004314, dated Aug. 8, 2006.

International Search Report for PCT/EP98/05113, dated May 26, 1999.

Kissa et al., "In vivo neuronal tracing with GFP-TTC Gene Delivery", Molecular and Cellular Neuroscience, vol. 20, p. 627-637. (2002).

Levrero et al., "Defective and nondefective adenovirus vectors for expressing foreign genes in vitro and in vivo", Gene 101:195-202 (1991).

Maskos et al., "Retrograde trans-synaptic transfer of green fluorescent protein allows the genetic mapping of neuronal circuits in transgenic mice", PNAS USA, vol. 99, pp. 10120-10125 (2002).

Miller et al., A transmissible retrovirus expressing human hypoxanthine phosphoribosyltransferase (HPRT): Gene transfer into cells obtained from humans deficient in HPTR, PNAS 80:4709-13 (1983).

Mueller et al., "Ways toward an early diagnosis in Azheimer's Disease: The Alzheimer's Disease Neuroimaging initiative", Alzheimers Dementia 1(1):55-66. (Jul. 2005).

Pawson et al., "Assembly of Cell Regulatory Systems Through Protein Interaction Domains", , Science 300:445-452. (2003).

Richards et al., "The normal developmental regulation of a cloned *sgs*3 'glue' gene chromosomally integrated in *Drosophila melanogaster* by P element transformation", EMBO J 2:2137-2142 (1983).

Roux et al., "Utilisation du fragment C-terminal de la neurotoxine tétanique pour visualiser et analyser des connexions neuronales et pour le transfert d'une activité biologique associée", Journal De La Société de Biologie, vol. 199, pp. 35-44 (2005). English Abstract.

Rubin et al., "Vectors for P element-mediated gene transfer in *Drosophila*", NAR 11:6341-6351 (1983).

Rusconi et al., "Transformation of frog embryos with a rabbit β-globin gene", PNAS 78:5051-5055 (1981).

Schwab and Thoenen, "Electron Microscopic Evidence for a Trans-synaptic Migration of Tetanus Toxin in Spinal Cord Motoneurons: An Autoradiographic and Morphometric Study", Brain Research, vol. 105, pp. 213-27 (1976).

St. Pierre and Linn, "A refined vector system for the in vitro construction of single-copy transcriptional or translational fusions to lacZ" Gene, vol. 169, pp. 65-68 (996)., 1996.

Steller et al., "Regulated expression of genes injected into early *Drosophila* embryos", EMBO 3:165-173 (1984).

Stuhlmann et al., "Introduction of a selectable gene into different animal tissue by retrovirus recombinant vector", PNAS 7151-7155 (1984).

Top et al., "Immunization with Live Types 7 and 4 Adenovirus Vaccines", Journal of Infectious Diseases, 124:148-154 (1971).
Wagner et al., Microinjection of a rabbit β-globin gene into zygotes and its subsequent expression in adult mice and their offspring, PNAS 78:6376-80 (1981).
Copending U.S. Appl. No. 11/375,093, filed Mar. 15, 2006.
Copending U.S. Appl. No. 11/543,164, filed Oct. 5, 2006.
Copending U.S. Appl. No. 09/501,787, filed Feb. 11, 2000.
Copending U.S. Appl. No. 11/812,812, filed Jun. 21, 2007.
Office Action mailed Apr. 21, 2009 in U.S. Appl. No. 10/817,961.
Advisory Action mailed Feb. 10, 2009 in U.S. Appl. No. 10/817,961.
Office Action mailed Oct. 17, 2008 in U.S. Appl. No. 10/817,961.
Office Action mailed Oct. 24, 2007 in U.S. Appl. No. 10/817,961.
Advisory Action mailed Aug. 13, 2007 in U.S. Appl. No. 10/817,961.
Office Action mailed Feb. 13, 2007 in U.S. Appl. No. 10/817,961.
Office Action mailed Jun. 13, 2006 in U.S. Appl. No. 10/817,961.
Office Action mailed May 27, 2009 in U.S. Appl. No. 11/375,093.
Advisory Action mailed Jul. 21, 2008 in U.S. Appl. No. 11/375,093.
Office Action mailed Feb. 20, 2008 in U.S. Appl. No. 11/375,093.
Office Action mailed May 29, 2007 in U.S. Appl. No. 11/375,093.
Office Action mailed Sep. 16, 2009 in U.S. Appl. No. 11/543,164.
Office Action mailed Feb. 2, 2009 in U.S. Appl. No. 11/543,164.
Advisory Action mailed Nov. 19, 2008 in U.S. Appl. No. 11/543,164.
Office Action mailed May 6, 2008 in U.S. Appl. No. 11/543,164.
Office Action mailed Jul. 23, 2007 in U.S. Appl. No. 11/543,164.
Office Action mailed Dec. 22, 2006 in U.S. Appl. No. 09/501,787.
Advisory Action mailed Aug. 16, 2006 in U.S. Appl. No. 09/501,787.
Office Action mailed Jan. 12, 2006 in U.S. Appl. No. 09/501,787.
Office Action mailed Apr. 14, 2004 in U.S. Appl. No. 09/501,787.
Advisory Action mailed Feb. 7, 2003 in U.S. Appl. No. 09/501,787.
Office Action mailed Jun. 18, 2002 in U.S. Appl. No. 09/501,787.
Office Action mailed Oct. 5, 2001 in U.S. Appl. No. 09/501,787.

\* cited by examiner

SK-TTC -> Genes

DNA sequence  1600 b.p.

```
  1 ggaaacagctatgaccatgattacgccaagctcgaaattaaccctcactaaagggaacaaagctggagctcggtacccg        80 ggaaacagctat ... gtcgttttacaa     linear 81 ggccacc ATG GTT GAT AAT AAT GAT GTT TTT TCA ACA ATT CCA ATT GTA GAT CTG GAT TGT TGG       141
  1         M   V   D   N   N   D   V   F   S   T   I   P   I   V   D   L   D   C   W        18

142 GTT GAT GAA GAT ATA TCA GAT ATA AAT GGC AAA GCA ATT GAA TAT TCT AAA AAG AGT ACA ATT TTA AAT       201
 19  V   D   E   D   I   S   D   I   N   G   K   A   I   E   Y   S   K   K   S   T   I   L   N       38

202 ATT AAT GAT ATT ATA TCA GAT ATA AAT GGC ATG GAT CCT AAA TCT ATG AAT AAC TTA CCT GAT TTA AAT CAT       261
 39  I   N   D   I   I   S   D   I   N   G   M   D   P   K   S   M   N   N   L   P   D   L   N   H       58

262 GAT GCT CAA TTG GTG CCC GGA CCC GGA CAT AAA GAT ATT GAA GTA AAA ATA ATA CCT GAT AGA TTA TCT TCT AAT GCT       321
 59  D   A   Q   L   V   P   G   P   G   H   K   D   I   E   V   K   I   I   P   D   R   L   S   S   N   A       78

322 TCT GAA GTT ATA GTG TGG TTG CAT AAA GAT ATT GAA TAT GCT AGT AGT CAT AGT CTA TTA AAA GAT TAT CCA AAT       381
 79  S   E   V   I   V   W   L   H   K   D   I   E   Y   A   S   S   H   S   L   L   K   D   Y   P   N       98

382 ACC GTT AGC TTT TGG TTG AGG TTG TTG TGG ACT TTT TCT TCT AAT GCT AGA GAG GCT ATT AGA GAG AAT TTT       441
 99  T   V   S   F   W   L   R   L   L   W   T   F   S   S   N   A   R   E   A   I   R   E   N   F       118

442 ACA AAT GAG GTA TCA CTT ACT ATA ATT GGT AGG ATT ACT GAT ATT AAT GCT CTA AAA CAT CTA TTA GAA CAA GGA TAT GGC       501
119  T   N   E   V   S   L   T   I   I   G   R   I   T   D   I   N   A   L   K   H   L   L   E   Q   G   Y   G       138

502 TGG AGT GTA CAA ATA ACT ATA ATT GAG AGT ATG AAT AAC CCT GAT ATT AAT GCT CTT AAT AGT TAT ATA TCA GGA GAA TCT GGT       561
139  W   S   V   Q   I   T   I   I   E   S   M   N   N   P   D   I   N   A   L   N   S   Y   I   S   G   E   S   G       158

562 GTT AGA CAA ATA TTT ATT ATT ACT AGA TTA GAT GAT AAA TTT TCT TCT AAT GCT ATT AGA GAG GAT AAT AAT TTT       621
159  V   R   Q   I   F   I   I   T   R   L   D   D   K   F   S   S   N   A   I   R   E   D   N   N   F       178

622 TGG GTT TTT ATA ACT ATA TTG TAT GCT AAT AGA GAG GCT ATT AGA GAG GAT AAT GCA AAT GGA       681
179  W   V   F   I   T   I   L   Y   A   N   R   E   A   I   R   E   D   N   A   N   G       198

682 GTA CTT ATG GGA AGT GCA GAA ATT ACT GGT TTA GGA GCT ATT AGA GAG GAT AAT ATA       741
199  V   L   M   G   S   A   E   I   T   G   L   G   A   I   R   E   D   N   I       218
```

FIG. 1A

| | | | | | | | | | | |
|---|---|---|---|---|---|---|---|---|---|---|
| 742<br>219 | ACA<br>T | TTA<br>L | AAA<br>K | CTA<br>L | GAT<br>D | AGA<br>R | TGT<br>C | AAT<br>N | AAT<br>N | AAT<br>N | CAA<br>Q | TAC<br>Y | GTT<br>V | TCT<br>S | ATT<br>I | GAT<br>D | AAA<br>K | TTT<br>F | AGG<br>R | 801<br>238 |
| 802<br>239 | ATA<br>I | TTT<br>F | TGC<br>C | AAA<br>K | GCA<br>A | TTA<br>L | AAT<br>N | CCA<br>P | AAA<br>K | GAG<br>E | ATT<br>I | GAA<br>E | AAA<br>K | TTA<br>L | TAC<br>Y | ACA<br>T | AGT<br>S | TTA<br>L | TCT<br>S | 861<br>258 |
| 862<br>259 | ATA<br>I | ACC<br>T | TTT<br>F | TTA<br>L | AGA<br>R | GAC<br>D | TTC<br>F | TGG<br>W | GGA<br>G | AAC<br>N | CCT<br>P | TTA<br>L | CGA<br>R | TAT<br>Y | GAT<br>D | ACA<br>T | GAA<br>E | TAT<br>Y | TAT<br>Y | 921<br>278 |
| 922<br>279 | ATA<br>I | CCA<br>P | GTA<br>V | GCT<br>A | TCT<br>S | AGT<br>S | AAA<br>K | GAT<br>D | GTT<br>V | CAA<br>Q | TTG<br>L | AAA<br>K | GAT<br>D | GTT<br>V | ACA<br>T | GAT<br>D | TAT<br>Y | ATG<br>M | TAT<br>Y | 981<br>298 |
| 982<br>299 | TTG<br>L | ACA<br>T | AAT<br>N | GCG<br>A | CCA<br>P | TCG<br>S | TAT<br>Y | ACT<br>T | AAC<br>N | GGA<br>G | AAA<br>K | ATA<br>I | TAT<br>Y | AGA<br>R | ATA<br>I | GAG<br>E | CAC<br>H | TTA<br>L | TAT<br>Y | 1041<br>318 |
| 1042<br>319 | AAT<br>N | GGA<br>G | CTA<br>L | AAA<br>K | TTT<br>F | ATT<br>I | ATA<br>I | AAA<br>K | CGA<br>R | TAT<br>Y | ACA<br>T | TCA<br>S | GTA<br>V | AAT<br>N | AAC<br>N | AAT<br>N | CCT<br>P | TTT<br>F | GTT<br>V | 1101<br>338 |
| 1102<br>339 | AAA<br>K | TCA<br>S | GGT<br>G | GAT<br>D | ATC<br>I | CCT<br>P | CTT<br>L | TAT<br>Y | AAT<br>N | GCC<br>A | TTT<br>F | AAA<br>K | TAT<br>Y | CTT<br>L | GAT<br>D | AGA<br>R | GAA<br>E | ATG<br>M | ATT<br>I | 1161<br>358 |
| 1162<br>359 | TAT<br>Y | CCG<br>P | AAA<br>K | GAT<br>D | GGA<br>G | CTT<br>L | CCT<br>P | CTT<br>L | TAT<br>Y | ATA<br>I | AAA<br>K | ATG<br>M | GAA<br>E | GCA<br>A | AAT<br>N | AAT<br>N | CTA<br>L | TTG<br>L | CGT<br>R | 1221<br>378 |
| 1222<br>379 | GCC<br>A | CCA<br>P | GAT<br>D | CAA<br>Q | ATC<br>I | TAT<br>Y | CTT<br>L | TAT<br>Y | AAA<br>K | TTA<br>L | TAT<br>Y | ACA<br>T | TCA<br>S | TAT<br>Y | CTT<br>L | GAA<br>E | ATG<br>M | GAT<br>D | AAA<br>K | 1281<br>398 |
| 1282<br>399 | TAT<br>Y | TCT<br>S | GTA<br>V | CAA<br>Q | CTT<br>L | AAT<br>N | TTA<br>L | TAT<br>Y | GAT<br>D | GAT<br>D | AAA<br>K | AAT<br>N | AGG<br>R | TGT<br>C | GAT<br>D | TGG<br>W | TAC<br>Y | TTT<br>F | GTA<br>V | 1341<br>418 |
| 1342<br>419 | CAT<br>H | AAT<br>N | CAT<br>H | GTA<br>V | CAA<br>Q | ATA<br>I | CCT<br>P | TAT<br>Y | AAT<br>N | CTT<br>L | AAT<br>N | GAT<br>D | CTT<br>L | AGA<br>R | GGA<br>G | CTA<br>L | GTA<br>V | GGT<br>G | ACC<br>T | 1401<br>438 |
| 1402<br>439 | TTT<br>F | AAT<br>N | GGT<br>G | CAA<br>Q | CTA<br>L | TAT<br>Y | AAA<br>K | GGC<br>G | AAC<br>N | GAT<br>D | CCA<br>P | AAT<br>N | AGG<br>R | GAT<br>D | ATA<br>I | TTA<br>L | ATT<br>I | AGC<br>S | TGG<br>W | 1461<br>458 |
| 1462<br>459 | GGA<br>G | TGG<br>W | ACA<br>T | AAT<br>N | CAT<br>D | GAT<br>* | TAA<br> | acagattgatatgttcatgacatatgcccgggatcctctagagtcgacctcgagg<br>(SEQ ID NO:2) | | | | | | | | | | | | 1535<br>464 |
| 1536 | ggggcccggtaccaattcgccctatagtgagtcgtattacaattcactggccgtcgttttacaa (SEQ ID NO:1) | | | | | | | | | | | | | | | | | | | 1600 |

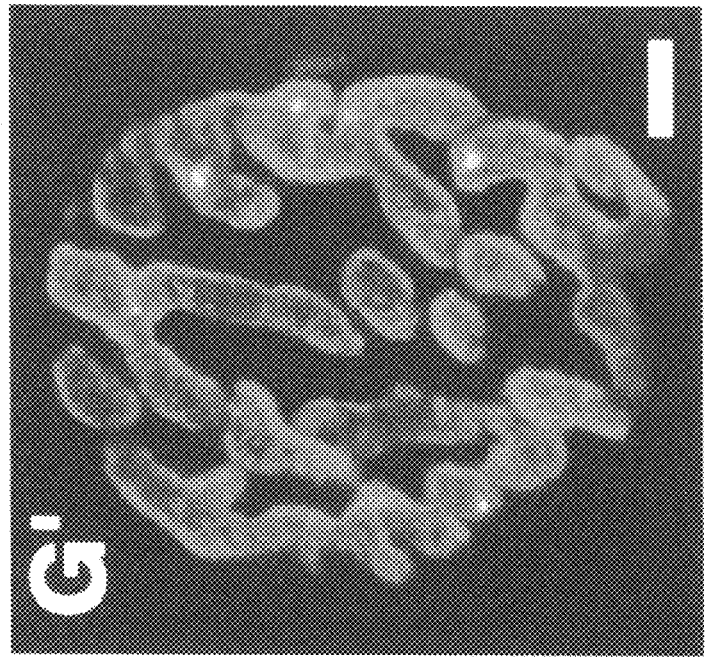
FIG. 6G'
FIG. 6G

GFP-TTC/TrkB

GFP-TTC/TrkB

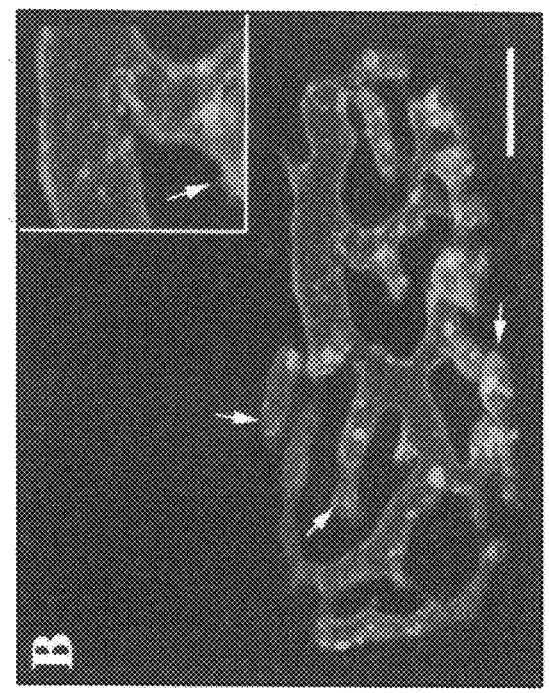
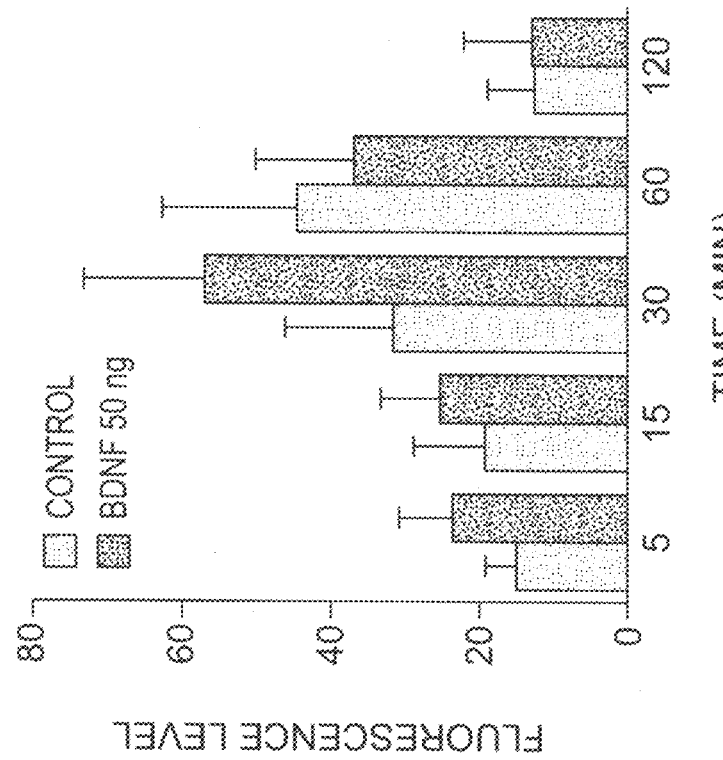
FIG. 9B
FIG. 9A

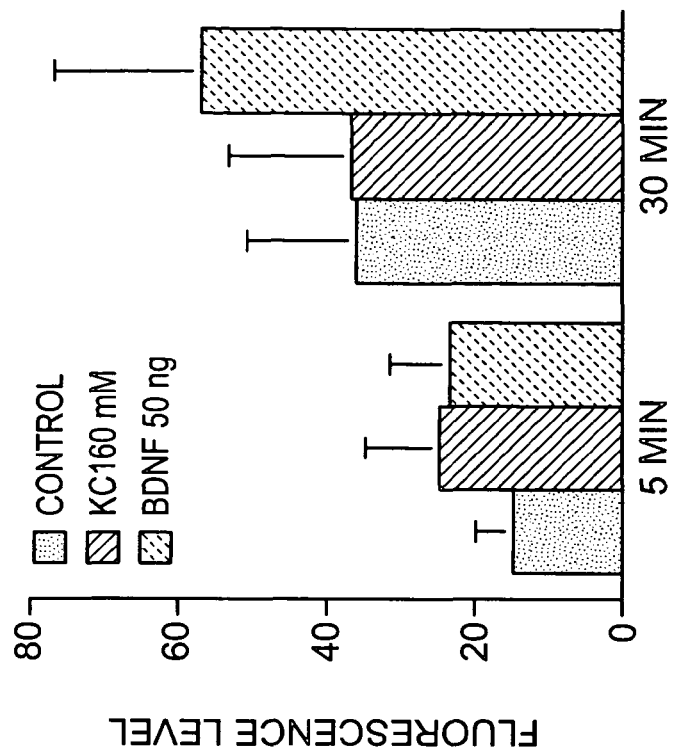
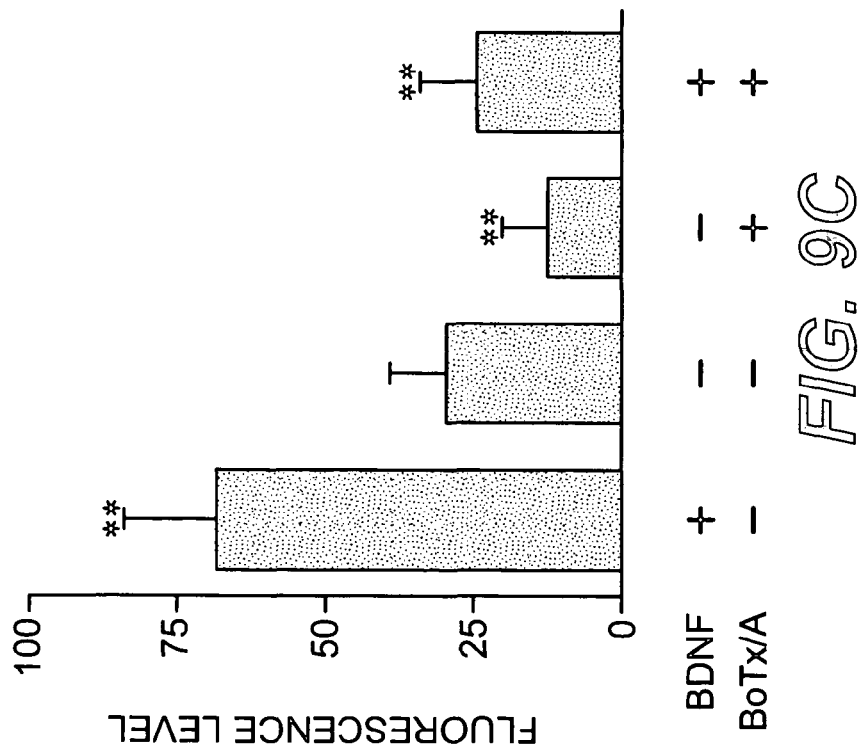
FIG. 9D
FIG. 9C

SEQUENCE LISTING

<160> NUMBER OF SEQ ID NOS: 18

<210> SEQ ID NO 1
<211> LENGTH: 1600
<212> TYPE: DNA
<213> ORGANISM: Clostridium tetani
<220> FEATURE:
<221> NAME/KEY: CDS
<222> LOCATION: (88)..(1476)

<400> SEQUENCE: 1

```
ggaaacagct atgaccatga ttacgccaag ctcgaaatta accctcacta aagggaacaa      60
aagctggagc tcggtacccg ggccacc atg gtt ttt tca aca cca att cca ttt     114
                                Met Val Phe Ser Thr Pro Ile Pro Phe
                                  1               5 tct tat tct aaa aat ctg gat tgt tgg gtt gat aat gaa gaa gat ata        162
Ser Tyr Ser Lys Asn Leu Asp Cys Trp Val Asp Asn Glu Glu Asp Ile
 10              15                  20                  25 gat gtt ata tta aaa aag agt aca att tta aat tta gat att aat aat        210
Asp Val Ile Leu Lys Lys Ser Thr Ile Leu Asn Leu Asp Ile Asn Asn
             30                  35                  40 gat att ata tca gat ata tct ggg ttt aat tca tct gta ata aca tat        258
Asp Ile Ile Ser Asp Ile Ser Gly Phe Asn Ser Ser Val Ile Thr Tyr
         45                  50                  55 cca gat gct caa ttg gtg ccc gga ata aat ggc aaa gca ata cat tta        306
Pro Asp Ala Gln Leu Val Pro Gly Ile Asn Gly Lys Ala Ile His Leu
     60                  65                  70 gta aac aat gaa tct tct gaa gtt ata gtg cat aaa gct atg gat att        354
Val Asn Asn Glu Ser Ser Glu Val Ile Val His Lys Ala Met Asp Ile
 75                  80                  85 gaa tat aat gat atg ttt aat aat ttt acc gtt agc ttt tgg ttg agg        402
Glu Tyr Asn Asp Met Phe Asn Asn Phe Thr Val Ser Phe Trp Leu Arg
 90                  95                 100                 105 gtt cct aaa gta tct gct agt cat tta gaa caa tat ggc aca aat gag        450
Val Pro Lys Val Ser Ala Ser His Leu Glu Gln Tyr Gly Thr Asn Glu
            110                 115                 120 tat tca ata att agc tct atg aaa aaa cat agt cta tca ata gga tct        498
Tyr Ser Ile Ile Ser Ser Met Lys Lys His Ser Leu Ser Ile Gly Ser
        125                 130                 135 ggt tgg agt gta tca ctt aaa ggt aat aac tta ata tgg act tta aaa        546
Gly Trp Ser Val Ser Leu Lys Gly Asn Asn Leu Ile Trp Thr Leu Lys
    140                 145                 150 gat tcc gcg gga gaa gtt aga caa ata act ttt agg gat tta cct gat        594
Asp Ser Ala Gly Glu Val Arg Gln Ile Thr Phe Arg Asp Leu Pro Asp
155                 160                 165 aaa ttt aat gct tat tta gca aat aaa tgg gtt ttt ata act att act        642
Lys Phe Asn Ala Tyr Leu Ala Asn Lys Trp Val Phe Ile Thr Ile Thr
170                 175                 180                 185
```

```
aat gat aga tta tct tct gct aat ttg tat ata aat gga gta ctt atg      690
Asn Asp Arg Leu Ser Ser Ala Asn Leu Tyr Ile Asn Gly Val Leu Met
            190                 195                 200 gga agt gca gaa att act ggt tta gga gct att aga gag gat aat aat      738
Gly Ser Ala Glu Ile Thr Gly Leu Gly Ala Ile Arg Glu Asp Asn Asn
        205                 210                 215 ata aca tta aaa cta gat aga tgt aat aat aat caa tac gtt tct          786
Ile Thr Leu Lys Leu Asp Arg Cys Asn Asn Asn Gln Tyr Val Ser
    220                 225                 230 att gat aaa ttt agg ata ttt tgc aaa gca tta aat cca aaa gag att      834
Ile Asp Lys Phe Arg Ile Phe Cys Lys Ala Leu Asn Pro Lys Glu Ile
235                 240                 245 gaa aaa tta tac aca agt tat tta tct ata acc ttt tta aga gac ttc      882
Glu Lys Leu Tyr Thr Ser Tyr Leu Ser Ile Thr Phe Leu Arg Asp Phe
250                 255                 260                 265 tgg gga aac cct tta cga tat gat aca gaa tat tat tta ata cca gta      930
Trp Gly Asn Pro Leu Arg Tyr Asp Thr Glu Tyr Tyr Leu Ile Pro Val
                270                 275                 280 gct tct agt tct aaa gat gtt caa ttg aaa aat ata aca gat tat atg      978
Ala Ser Ser Ser Lys Asp Val Gln Leu Lys Asn Ile Thr Asp Tyr Met
            285                 290                 295 tat ttg aca aat gcg cca tcg tat act aac gga aaa ttg aat ata tat     1026
Tyr Leu Thr Asn Ala Pro Ser Tyr Thr Asn Gly Lys Leu Asn Ile Tyr
        300                 305                 310 tat aga agg tta tat aat gga cta aaa ttt att ata aaa aga tat aca     1074
Tyr Arg Arg Leu Tyr Asn Gly Leu Lys Phe Ile Ile Lys Arg Tyr Thr
    315                 320                 325 cct aat aat gaa ata gat tct ttt gtt aaa tca ggt gat ttt att aaa     1122
Pro Asn Asn Glu Ile Asp Ser Phe Val Lys Ser Gly Asp Phe Ile Lys
330                 335                 340                 345 tta tat gta tca tat aac aat aat gag cac att gta ggt tat ccg aaa     1170
Leu Tyr Val Ser Tyr Asn Asn Asn Glu His Ile Val Gly Tyr Pro Lys
                350                 355                 360 gat gga aat gcc ttt aat aat ctt gat aga att cta aga gta ggt tat     1218
Asp Gly Asn Ala Phe Asn Asn Leu Asp Arg Ile Leu Arg Val Gly Tyr
            365                 370                 375 aat gcc cca ggt atc cct ctt tat aaa aaa atg gaa gca gta aaa ttg     1266
Asn Ala Pro Gly Ile Pro Leu Tyr Lys Lys Met Glu Ala Val Lys Leu
        380                 385                 390 cgt gat tta aaa acc tat tct gta caa ctt aaa tta tat gat gat aaa     1314
Arg Asp Leu Lys Thr Tyr Ser Val Gln Leu Lys Leu Tyr Asp Asp Lys
    395                 400                 405 aat gca tct tta gga cta gta ggt acc cat aat ggt caa ata ggc aac     1362
Asn Ala Ser Leu Gly Leu Val Gly Thr His Asn Gly Gln Ile Gly Asn
410                 415                 420                 425 gat cca aat agg gat ata tta att gca agc aac tgg tac ttt aat cat     1410
Asp Pro Asn Arg Asp Ile Leu Ile Ala Ser Asn Trp Tyr Phe Asn His
                430                 435                 440 tta aaa gat aaa att tta gga tgt gat tgg tac ttt gta cct aca gat     1458
Leu Lys Asp Lys Ile Leu Gly Cys Asp Trp Tyr Phe Val Pro Thr Asp
            445                 450                 455 gag gga tgg aca aat gat taaacagatt gatatgttca tgacatatgc             1506
Glu Gly Trp Thr Asn Asp
            460 ccgggatcct ctagagtcga cctcgagggg gggcccggta cccaattcgc cctatagtga   1566 gtcgtattac aattcactgg ccgtcgtttt acaa                               1600

<210> SEQ ID NO 2
<211> LENGTH: 463
```

```
<212> TYPE: PRT
<213> ORGANISM: Clostridium tetani

<400> SEQUENCE: 2
```

| | | | | | | | | | | | | | | |
|---|---|---|---|---|---|---|---|---|---|---|---|---|---|---|
|Met|Val|Phe|Ser|Thr|Pro|Ile|Pro|Phe|Ser|Tyr|Ser|Lys|Asn|Leu|Asp
|1| | | |5| | | | |10| | | | |15

Cys Trp Val Asp Asn Glu Glu Asp Ile Asp Val Ile Leu Lys Lys Ser
            20                  25                  30

Thr Ile Leu Asn Leu Asp Ile Asn Asn Asp Ile Ile Ser Asp Ile Ser
                35                  40                  45

Gly Phe Asn Ser Ser Val Ile Thr Tyr Pro Asp Ala Gln Leu Val Pro
 50                  55                  60

Gly Ile Asn Gly Lys Ala Ile His Leu Val Asn Asn Glu Ser Ser Glu
 65                  70                  75                  80

Val Ile Val His Lys Ala Met Asp Ile Glu Tyr Asn Asp Met Phe Asn
                85                  90                  95

Asn Phe Thr Val Ser Phe Trp Leu Arg Val Pro Lys Val Ser Ala Ser
            100                 105                 110

His Leu Glu Gln Tyr Gly Thr Asn Glu Tyr Ser Ile Ile Ser Ser Met
        115                 120                 125

Lys Lys His Ser Leu Ser Ile Gly Ser Gly Trp Ser Val Ser Leu Lys
130                 135                 140

Gly Asn Asn Leu Ile Trp Thr Leu Lys Asp Ser Ala Gly Glu Val Arg
145                 150                 155                 160

Gln Ile Thr Phe Arg Asp Leu Pro Asp Lys Phe Asn Ala Tyr Leu Ala
                165                 170                 175

Asn Lys Trp Val Phe Ile Thr Ile Thr Asn Asp Arg Leu Ser Ser Ala
            180                 185                 190

Asn Leu Tyr Ile Asn Gly Val Leu Met Gly Ser Ala Glu Ile Thr Gly
        195                 200                 205

Leu Gly Ala Ile Arg Glu Asp Asn Asn Ile Thr Leu Lys Leu Asp Arg
210                 215                 220

Cys Asn Asn Asn Asn Gln Tyr Val Ser Ile Asp Lys Phe Arg Ile Phe
225                 230                 235                 240

Cys Lys Ala Leu Asn Pro Lys Glu Ile Glu Lys Leu Tyr Thr Ser Tyr
                245                 250                 255

Leu Ser Ile Thr Phe Leu Arg Asp Phe Trp Gly Asn Pro Leu Arg Tyr
            260                 265                 270

Asp Thr Glu Tyr Tyr Leu Ile Pro Val Ala Ser Ser Ser Lys Asp Val
        275                 280                 285

Gln Leu Lys Asn Ile Thr Asp Tyr Met Tyr Leu Thr Asn Ala Pro Ser
290                 295                 300

Tyr Thr Asn Gly Lys Leu Asn Ile Tyr Tyr Arg Arg Leu Tyr Asn Gly
305                 310                 315                 320

Leu Lys Phe Ile Ile Lys Arg Tyr Thr Pro Asn Asn Glu Ile Asp Ser
                325                 330                 335

Phe Val Lys Ser Gly Asp Phe Ile Lys Leu Tyr Val Ser Tyr Asn Asn
            340                 345                 350

Asn Glu His Ile Val Gly Tyr Pro Lys Asp Gly Asn Ala Phe Asn Asn
        355                 360                 365

Leu Asp Arg Ile Leu Arg Val Gly Tyr Asn Ala Pro Gly Ile Pro Leu
370                 375                 380

Tyr Lys Lys Met Glu Ala Val Lys Leu Arg Asp Leu Lys Thr Tyr Ser
385                 390                 395                 400

```
Val Gln Leu Lys Leu Tyr Asp Asp Lys Asn Ala Ser Leu Gly Leu Val
            405                 410                 415

Gly Thr His Asn Gly Gln Ile Gly Asn Asp Pro Asn Arg Asp Ile Leu
            420                 425                 430

Ile Ala Ser Asn Trp Tyr Phe Asn His Leu Lys Asp Lys Ile Leu Gly
            435                 440                 445

Cys Asp Trp Tyr Phe Val Pro Thr Asp Glu Gly Trp Thr Asn Asp
            450                 455                 460

<210> SEQ ID NO 3
<211> LENGTH: 1392
<212> TYPE: DNA
<213> ORGANISM: Clostridium tetani

<400> SEQUENCE: 3
atggtttttt caacaccaat tccattttct tattctaaaa atctggattg ttgggttgat      60
aatgaagaag atatagatgt tatattaaaa aagagtacaa ttttaaattt agatattaat     120
aatgatatta tatcagatat atctgggttt aattcatctg taataacata tccagatgct     180
caattggtgc ccgaataaaa tggcaaagca atacatttag taaacaatga atcttctgaa     240
gttatagtgc ataaagctat ggatattgaa tataatgata tgtttaataa ttttaccgtt     300
agcttttggt tgagggttcc taaagtatct gctagtcatt agaacaata tggcacaaat      360 gagtattcaa taattagctc tatgaaaaaa catagtctat caataggatc tggttggagt     420
gtatcactta aagtaataa cttaatatgg actttaaaag attccgcggg agaagttaga     480
caaataactt ttagggattt acctgataaa tttaatgctt atttagcaaa taatgggtt      540 tttataacta ttactaatga tagattatct tctgctaatt tgtatataaa tggagtactt     600
atgggaagtg cagaaaattac tggtttagga gctattagag aggataataa tataacatta     660
aaactagata gatgtaataa taataatcaa tacgtttcta ttgataaatt taggatattt     720
tgcaaagcat taaatccaaa agagattgaa aaattataca aagttatttt atctataacc     780 ttttttaagag acttctgggg aaaaccctta cgatatgata cagaatatta tttaatacca     840
gtagcttcta gttctaaaga tgttcaattg aaaaatataa cagattatat gtatttgaca     900
aatgcgccat cgtatactaa cggaaaattg aatatatatt atagaaggtt atataatgga     960 ctaaaatta ttataaaag atatacacct aataatgaaa tagattcttt tgttaaatca     1020
ggtgatttta ttaaattata tgtatcatat aacaataatg agcacattgt aggttatccg     1080
aaaagtggaa atgcctttaa taatcttgat agaattctaa gagtaggtta taatgcccca     1140
ggtatccctc tttataaaaa aatggaagca gtaaaattgc gtgatttaaa aacctattct     1200
gtacaactta attatatga tgataaaaat gcatctttag gactagtagg tacccataat     1260
ggtcaaatag gcaacgatcc aaatagggat atattaattg caagcaactg gtactttaat     1320
catttaaaag ataaaatttt aggatgtgat tggtactttg tacctacaga tgagggatgg     1380
acaaatgatt aa                                                         1392

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 4
ccccccgggc caccatggtt ttttcaacac caattccatt ttcttattc                    49
```

```
<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5
ctaaaccagt aatttctg                                                    18

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
aattatggac tttaaaagat tccgc                                            25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
ggcattataa cctactctta gaat                                             24

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8
aatgccttta ataatcttga tagaaat                                          27

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 9
ccccccgggc atatgtcatg aacatatcaa tctgtttaat c                          41

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
ctgaatatcg acggtttcca tatg                                             24

<210> SEQ ID NO 11
<211> LENGTH: 40
<212> TYPE: DNA
<213> ORGANISM: Artificial Sequence
<220> FEATURE:
<223> OTHER INFORMATION: Description of Artificial Sequence: Primer
```

<400> SEQUENCE: 11
ggcagtctcg agtctagacc atggctttt gacaccagac                40

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 12
catgactggg gatccccagt                                     20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 13
tatgataaaa atgcatcttt agga                                24

<210> SEQ ID NO 14
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 14
tggagtcgac gctagcagga tcatttgtcc atccttc                  37

<210> SEQ ID NO 15
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 15 gctagcgc                                                   8

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 16
gatatcggcg cgccagc                                        17

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 17
tggcgcgccg atatcgc                                        17

```
<210> SEQ ID NO 18
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide linker

<400> SEQUENCE: 18
tcgatggcgc gcca                                                         14
```

IN VIVO MODULATION OF NEURONAL TRANSPORT

CROSS REFERENCE TO RELATED APPLICATIONS

The present application is a continuation-in-part of copending U.S. application Ser. No. 09/816,467, filed Mar. 26, 2001, which is a continuation of U.S. application Ser. No. 09/129,368, filed Aug. 5, 1998, now abandoned, which claims the benefit of Provisional Application No. 60/055,615, filed Aug. 14, 1997 and Provisional Application No. 60/065,236, filed Nov. 13, 1997. The entire disclosure of each of these applications is relied upon and incorporated by reference herein.

BACKGROUND OF THE INVENTION

This invention relates to the use of part of tetanus toxin for delivering a composition to the central nervous system of a human or animal. This invention also relates to a hybrid fragment of tetanus toxin, a polynucleotide that hybridizes with natural tetanus toxin, and a composition containing the tetanus toxin fragment as an active molecule. Further, this invention relates to a vector comprising a promoter and a nucleic acid sequence encoding the tetanus toxin fragment.

Tetanus toxin is produced by *Clostridium tetani* as an inactive, single, polypeptide chain of 150 kD composed of three 50 kD domains connected by protease-sensitive loops. The toxin is activated upon selective proteolytic cleavage, which generates two disulfide-linked chains: L (light, 50 kD) and H (heavy, 100 kD) [Montecucco C. and Schiavo G. Q. Rev. Biophys., (1995), 28: 423-472].

Evidence for the retrograde axonal transport of tetanus toxin to central nervous system (CNS) has been described by Erdmann et al. [Naunyn Schmiedebergs Arch Phamacol., (1975), 290:357-373], Price et al. [Science, (1975), 188:945-94], and Stoeckel et al. [Brain Res., (1975), 99:1-16]. In each of these studies, radiolabeled toxin was found inside membrane bound vesicles. Another property was the transynaptic movement of tetanus toxin that was demonstrated first by autoradiographic localization of $^{125}$I-labeled tetanus toxin in spinal cord interneurons after injection into a muscle [Schwab and Thoenen, Brain Res., (1976), 105:218-227].

The structure of this tetanus toxin has been elucidated by Helting et al. [J. Biol. Chem., (1977), 252:187-193]. Papain cleaves the tetanus toxin in two fragments:

- the C terminal part of the heavy chain, 451 amino acids, also called fragment C; and
- the other part contained the complementary portion called fragment B linked to the light chain (fragment A) via a disulfide bond.

European Patent No. EP 0 030 496 B1 showed the retrograde transport of a fragment B-II$_b$ to the CNS and was detected after injection in the median muscle of the eye in primary and second order neurons. This fragment may consist of "isofragments" obtained by clostridial proteolysis. Later, this fragment B-II$_b$ was demonstrated to be identical to fragment C obtained by papain digestion by Eisel et al. [EMBO J., 1986, 5:2495-2502].

This EP patent also demonstrated the retrograde transport of a conjugate consisting of a I$_{bc}$ tetanus toxin fragment coupled by a disulfide bond to B-II$_b$ from axonal endings within the muscle to the motoneuronal perikarya and pericellular spaces. (The I$_{bc}$ fragment corresponds to the other part obtained by papain digestion as described above by Helting et al.). There is no evidence that this conjugate was found in second order neurons. The authors indicated that a conjugate consisting of the fragment B-II$_b$ coupled by a disulfide bond to a therapeutic agent was capable of specific fixation to gangliosides and synaptic membranes. No result showed any retrograde axonal transport or a transynaptic transport for such conjugate.

Another European Patent, No. EP 0 057 140 B1, showed equally the retrograde transport of a fragment II$_c$ to the CNS. As in the European Patent No. EP 0 030 496 B1, the authors indicated that a conjugate consisting of the fragment II$_c$ and a therapeutic agent was capable of specific fixation, but no result illustrated such allegation. This fragment II$_c$ corresponds to the now called fragment C obtained by papain digestion.

Francis et al. [J. Biol. Chem., (1995), 270(25):15434-15442] led an in vitro study showing the internalization by neurons of hybrid between SOD-1 (Cu Zn superoxide dismutase) and a recombinant C tetanus toxin fragment by genetic recombination. This recombinant C tetanus toxin fragment was obtained from Halpern group. (See ref. 11).

Moreover, Kuypers H. G. J. M and Ugolini G. [TINS, (1990), 13(2):71-75] indicated in their publication concerning viruses as transneuronal tracers that, despite the fact that tetanus toxin fragment binds to specific receptors on neuronal membranes, transneuronal labeling is relatively weak and can be detected only in some of the synaptically connected neurons.

Notwithstanding these advances in the art, there still exists a need for methods for delivering compositions into the human or animal central nervous system. There also exists a need in the art for biological agents that can achieve this result.

Additionally, activity-dependent modification of neuronal connectivity and synaptic plasticity play an important role in the development and function of the nervous system. Recently, much effort has been dedicated to following such modifications by the engineering of new optically detectable genetic tools. For example, fused to a reporter gene such as LacZ or GFP (Green Fluorescent Protein), the atoxic C-terminal fragment of tetanus toxin (or TTC fragment) can traffic retrogradely and transsynaptically inside a restricted neural network either after direct injection of the hybrid protein (Coen et al., 1997), or when expressed as a transgene in mice (Maskos et al., 2002). The dynamics of βgal-TTC clustering at the neuromuscular junction (NMJ) is strongly dependent on a presynaptic neuronal activity and probably involves fast endocytic pathways (Miana-Mena et al., 2002). Neuronal activity may induce this clustering and internalization at the NMJ by enhancing the secretion and/or action of various molecules at the synapse.

Over the past decade, various data indicate that neurotrophins, a family of structurally and functionally related proteins, including NGF (Nerve Growth Factor); BDNF (Brain Derived Neurotrophic Factor); Neurotrophin 3 (NT-3) and Neurotrophin 4 (NT-4), not only promote neuronal survival and morphological differentiation, but also can acutely modify synaptic transmission and connectivity in central synapses, thus providing a connection between neuronal activity and synaptic plasticity (McAllister et al., 1999; Poo, 2001; Tao and Poo, 2001). The role of these factors in neurotransmission between motoneurons and skeletal muscle cells has been studied using Xenopus nerve-muscle co-culture studies, whereby the treatment of these cultures with exogenous BDNF, NT-3 or NT-4 leads to an increase of synaptic transmission by enhancing neurotransmitter secretion (Lohof et al., 1993; Stoop and Poo, 1996; Wang and Poo, 1997). Moreover, the muscular expression of NT-3 and NT-4 (Funakoshi et al., 1995; Xie et al., 1997), as well as NT-4 secretion (Wang and Poo, 1997) are regulated by electrical activity. This family of proteins thus provides a molecular link between electrical neuronal activity and synaptic changes.

The cellular actions of neurotrophins are mediated by two types of receptors: the $p75^{NTR}$ receptor, mainly expressed during early neuronal development, and a Trk tyrosine kinase receptor (Bothwell, 1995). The interaction of neurotrophins with Trk receptors is specific. TrkB and TrkC, are activated by BDNF/NT-4 and NT-3, respectively, and are expressed by motor neurons. TrkA, which is expressed by sensory neurons, is activated by NGF. Recently, evidence for a co-trafficking between TTC and the neurotrophin receptor $p75^{NTR}$ has been reported in cultured motoneurons (Lalli and Schiavo, 2002), as well as the activation by tetanus toxin and the TTC fragment of intracellular pathways involving Trk receptors in cultured cortical neurons (Gil et al., 2003).

Notwithstanding the knowledge in the art, there still exists a need for understanding the influences of neurotrophins and other neurotrophic factors on TTC traffic at the NMJ in vivo and for developing methods of using these neurotrophins and neurotrophic factors, and agonists or antagonists thereof, to modulate the neuronal transport of a tetanus toxin or a fusion protein comprising a fragment C of the tetanus toxin.

SUMMARY OF THE INVENTION

This invention aids in fulfilling these needs in the art. More particularly, this invention provides a method for in vivo delivery of desired composition into the central nervous system (CNS) of the mammal, wherein the composition comprises a non-toxic proteolytic fragment of tetanus toxin (TT) in association with at least a molecule having a biological function. The composition is capable of in vivo retrograde transport and transynaptic transport into the CNS and of being delivered to different areas of the CNS.

This invention also provides a hybrid fragment of tetanus toxin comprising fragment C and fragment B or a fraction thereof of at least 11 amino acid residues or a hybrid fragment of tetanus toxin comprising fragment C and fragment B or a fraction thereof of at least 11 amino acid residues and a fraction of fragment A devoid of its toxic activity corresponding to the proteolytic domain having a Zinc-binding motif located in the central part of the chain between the amino acids 225 and 245, capable of transferring in vivo a protein, a peptide, or a polynucleotide through a neuromuscular junction and at least one synapse.

Further, this invention provides a composition comprising an active molecule in association with the hybrid fragment of tetanus toxin (TT) or a variant thereof. The composition is useful for the treatment of a patient or an animal affected with CNS disease, which comprises delivering a composition of the invention to the patient or animal. In addition, the composition of this invention may be useful to elicit a immune response in the patient or animal affected with CNS, which comprises delivering a composition of the invention to the patient or animal.

Moreover, this invention provides polynucleotide variant fragments capable of hybridizing under stringent conditions with the natural tetanus toxin sequence. The stringent conditions are for example as follows: at 42° C. for 4 to 6 hours in the presence of 6×SSC buffer, 1× Denhardt's Solution, 1% SDS, and 250 µg/ml of tRNA. (1×SSC corresponds to 0.15 M NaCl and 0.05 M sodium citrate; 1× Denhardt's solution corresponds to 0.02% Ficoll, 0.02% polyvinyl pyrrolidone and 0.02% bovine serum albumin). The two wash steps are performed at room temperature in the presence of 0.1×SCC and 0.1% SDS.

A polynucleotide variant fragment means a polynucleotide encoding for a tetanus toxin sequence derived from the native tetanus toxin sequence and having the same properties of transport.

In addition, the invention provides a vector comprising a promoter capable of expression in muscle cells and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be the CMV promoter and preferably the CMV promoter contained in pcDNA 3.1 (In Vitrogen, ref. V790-20), or the promoter β actin as described in Bronson S. V. et al. (PNAS, 1996, 93:9067-9072).

In addition, the invention provides a vector comprising a promoter capable of expression in neuronal cells or in precursors (such NT2(hNT) precursor cells from Stratagene reference # 204101) and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be β actin (see the above reference). These vectors are useful for the treatment of a patient or an animal infected with CNS disease comprising delivering the vector of the invention to the patient or animal. In addition, these vectors are useful for eliciting immune responses in the patient or animal.

One advantage of the present invention comprising the fragment of tetanus toxin (fragment A, B, and C) is to obtain a better transport of the fragment inside the organism compared with fragment C. Another advantage of the composition of the invention is to obtain a well defined amino acid sequence and not a multimeric composition. Thus, one can easily manipulate this composition in gene therapy.

In another embodiment, this invention provides a method of modulating the transport in a neuron of a neurotoxin, such as the tetanus toxin, or a fusion protein comprising a fragment C of the tetanus toxin. These methods comprise administering neurotrophic factors such as BDNF, NT-4, and GDNF, and agonists and antagonists thereof, to modulate internalization at a neuromuscular junction of a neurotoxin or a fusion protein comprising the TTC fragment according to the invention.

In one embodiment, these methods further comprise administering to the neuron a TrkB receptor agonist or a TrkB receptor antagonist in an amount sufficient to modulate the neuronal transport of the tetanus toxin or the fusion protein. The term "modulate" and its cognates refer to the capability of a compound acting as either an agonist or an antagonist of a certain reaction or activity. The term modulate, therefore, encompasses the terms "increase" and "decrease." The term "increase," for example, refers to an increase in the neuronal transport of a polypeptide in the presence of a modulatory compound, relative to the transport of the polypeptide in the absence of the same compound. Analogously, the term "decrease" refers to a decrease in the neuronal transport of a polypeptide in the presence of a modulatory compound, relative to the transport of the polypeptide in the absence of the same compound. The neuronal transport of polypeptides can be measured as described herein or by techniques generally known in the art.

The TrkB receptor agonists include neurotrophic factors that activate a TrkB receptor, such as a Brain Derived Neurotrophic Factor or a Neurotrophin 4. The TrkB receptor agonists can also include antibodies that bind to TrkB receptors and activate them. These methods of using TrkB receptor agonists provide useful methods for enhancing the neuronal transport of a tetanus toxin or a tetanus toxin fusion protein.

The TrkB receptor antagonists include antibodies that bind to a TrkB receptor agonist, such as those described above, and thereby decrease the activation of a TrkB receptor. For example, these antibodies can be directed to neurotrophic factors that activate a TrkB receptor, such as a Brain Derived Neurotrophic Factor or a Neurotrophin 4. In addition, TrkB receptor antagonists include antibodies that bind to TrkB receptors and inactivate them. These methods of using TrkB receptor agonists provide useful methods for decreasing or preventing the neuronal transport of a tetanus toxin or a tetanus toxin fusion protein.

In another embodiment, these methods further comprise administering to the neuron a GFRα/cRET receptor agonist or a GFRα/cRET receptor antagonist in an amount sufficient to modulate the neuronal transport of the tetanus toxin or the fusion protein.

The GFRα/cRET receptor agonists include neurotrophic factors that activate a GFRα/cRET receptor, such as a Glial-Derived Neurotrophic Factor. The GFRα/cRET receptor agonists can also include antibodies that bind to GFRα/cRET receptors and activate them. These methods of using GFRα/cRET receptor agonists provide useful methods for enhancing the neuronal transport of a tetanus toxin or a tetanus toxin fusion protein.

The GFRα/cRET receptor antagonists include antibodies that bind to a GFRα/cRET receptor agonist, such as those described above, and thereby decrease the activation of a GFRα/cRET receptor. For example, these antibodies can be directed to neurotrophic factors that activate a GFRα/cRET receptor, such as a Glial-Derived Neurotrophic Factor. In addition, GFRα/cRET receptor antagonists include antibodies that bind to GFRα/cRET receptors and inactivate them. These methods of using GFRα/cRET receptor agonists provide useful methods for decreasing or preventing the neuronal transport of a tetanus toxin or a tetanus toxin fusion protein.

In these methods, the agonist or antagonist can be administered to neuronal cells that already contain a tetanus toxin or a fusion protein. Alternatively, the tetanus toxin or fusion protein can be administered concurrently with or after the administration of the agonist or antagonist.

In one embodiment, the TTC-containing fusion proteins of the present invention comprises a second protein that is encoded by a reporter gene, such as the lac Z gene or the Green Fluorescent Protein gene. Such fusion proteins are useful for visualizing modulation of the synaptic plasticity in vivo, including in a human, for example by magnetic resonance imaging. For example, the fusion proteins can be used to monitor and detect the effects of a compound, such as a neurotrophic factor, on neuronal transport. In these methods, the compound and the fusion protein are administered to a neuron, and the fusion protein is detected to determine the effect of the compound on the neuronal transport. In addition, the fusion proteins can be used to detect modifications in trafficking patterns within a restricted neural network, such as those used in known animal models for neurodegenerative diseases. The fusion proteins can also be used in screening methods to detect compounds that reduce or prevent neuronal transport of a tetanus toxin. Compounds so identified can be used to prevent or treat tetanus infections.

The TTC fragment can also be coupled to a neurotrophic factor and administered to a patient to treat CNS pathologies associated with production defects of different factors. The TTC fragment could also be used as a vector for modulating interactions with proteins involved in neurodegenerative diseases.

The present invention also provides compositions comprising a TrkB receptor agonist or a GFRα/cRET receptor agonist and a fusion protein comprising a fragment C of the tetanus toxin fused to a second protein. In one embodiment, the TrkB agonist is a neurotrophic factor such as a Brain Derived Neurotrophic Factor or a Neurotrophin 4. In another embodiment, the GFRα/cRET receptor agonist is a neurotrophic factor, such as Glial-Derived Neurotrophic Factor

BRIEF DESCRIPTION OF THE DRAWINGS

This invention will be more fully described with reference to the drawings in which.

Figure 2:
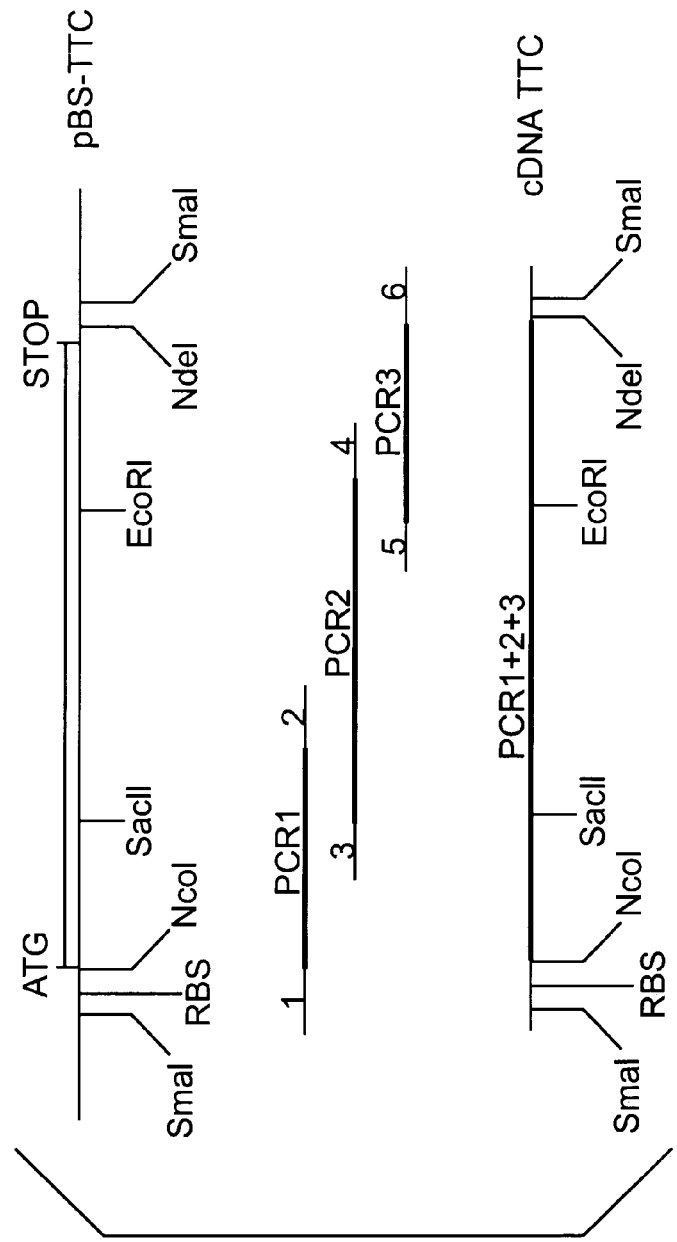
FIG. 2 shows the details of construct pBS:TTC, which is further described in Example 1.
Figure 3:
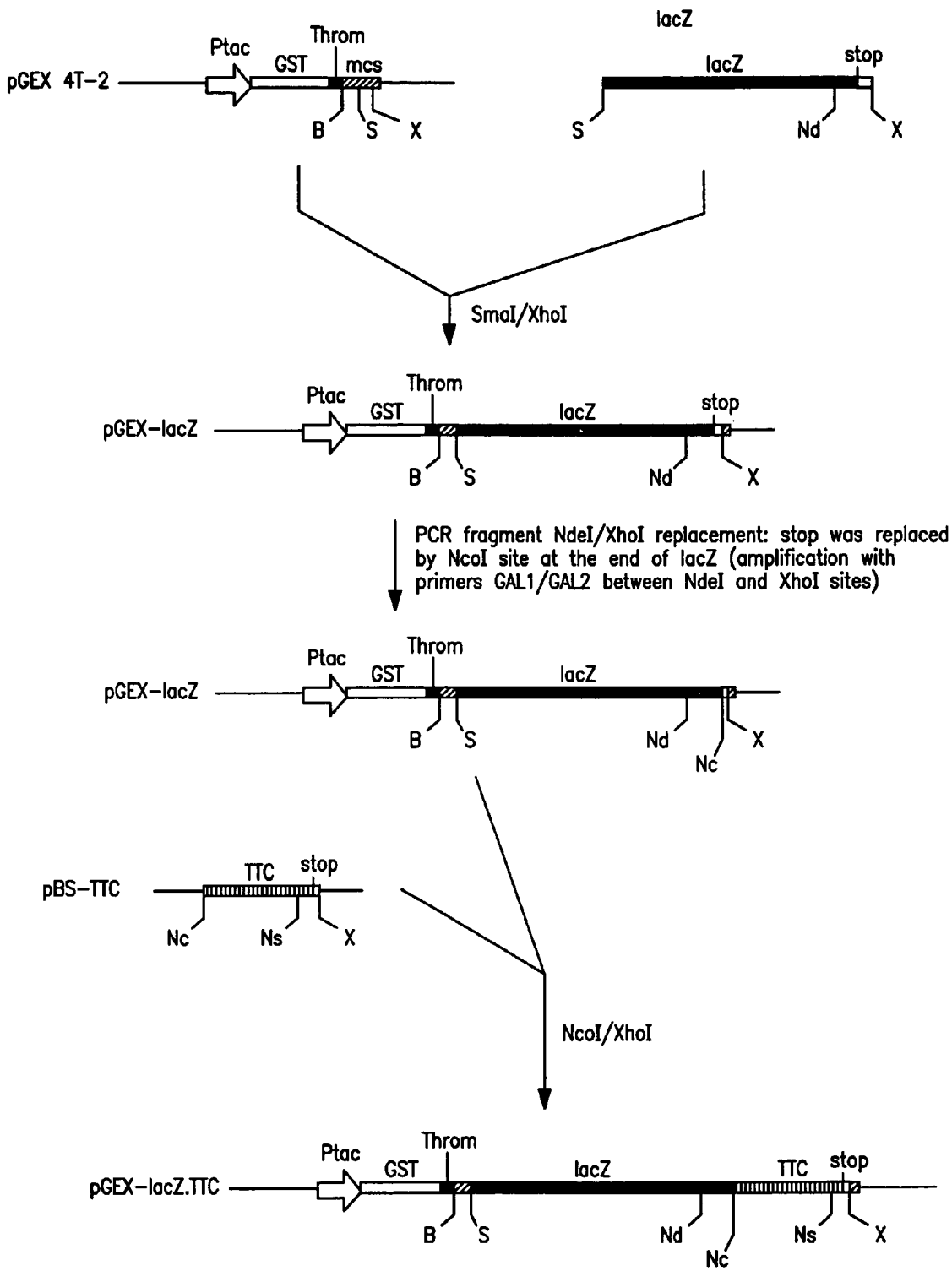
FIG. 3 depicts pGEX:lacZ-TTC construct.

(A) Two hours after the subcutaneous injection of GFP-TTC in the vicinity of the LAL muscle, the probe (green) was concentrated at motor nerve endings of NMJ. Associated intramuscular motor axons were immunostained (red) with an antibody against NF200. GFP-TTC labeling was also detected in sensory nerve fibers (arrows) and at the nodes of Ranvier of myelinated axons (arrowheads). (B) Strong nodal labeling with GFP-TTC (green) (arrow) in a single living myelinated axon. Myelin was passively stained with RH414 dye (red). (C) Two hours after injection as in A, LAL muscle fibers were fixed and labeled for troponin T by indirect immunofluorescence. (C' and C") Inset is a side view image of a NMJ showing that GFP-TTC staining (green) is located presynaptically. (D-G) LAL was harvested at various times after GFP-TTC injection and NMJ identified in red by labeling with TRITC-a-BTX (D'-G'). D-D': 5 min E-E': 30 min; F-F': 2 h and G-G': 24 h.

Scale bars: A, 20 µm; B, 8 µm; C: 20 µm; D, 2 µm; E-G, 5 µm.

FIG. 7 shows that BDNF increases GFP-TTC recruitment at the NMJ in a dose-dependent manner.

(A1-A6) The NMJ on LAL muscles was identified by TRITC-a-BTX labeling 30 min after in vivo co-injection of GFP-TTC with various amounts of BDNF. The level of GFP fluorescence was quantified over these areas (see B). An enhancement of axonal labeling (arrows), more pronounced with higher BDNF concentration, was also detected. Scale bars: 20 µm (B) Confocal sections of the NMJ were collected for analysis and projections generated. TRIT-a-BTX labeling determines the area of the NMJ over which the global GFP fluorescent signal was measured. For each, (n=15-20), the GFP fluorescence was divided by NMJ area (in µm$^2$) to obtain the fluorescence level. Error bars indicate S.D. **P<0.005; t-test, vs control.

FIG. 8 depicts the immunofluorescence visualization of TrkB at the LAL NMJ. Two hours after GFP-TTC injection in LAL, confocal analysis was performed. (A-B) The fusion protein was identified in green directly by GFP fluorescence. (C-D) TrkB, identified (in red) by indirect immunofluorescence (see material and methods), was located at the NMJ.

(E-F) However, when the two projections were overlaid, no overlap was found between the TrkB and the GFP-TTC signals.

Scale bar: Top: 5 μm; Bottom: 2 μm

FIG. 9 represents the results of experiments elucidating the mechanisms of GFP-TTC recruitment to the NMJ.

(A) Quantification of GFP-TTC fluorescence was performed, as described in FIG. 7 at various time after co-injection with or without 50 ng BDNF.

(B) After in vitro loading for 45 min with GFP-TTC, the excised LAL muscle was fixed and SV2 protein detected by indirect immunofluorescence (red). SV2 labeling was mostly diffuse and concentrated in a few areas of the NMJ (arrows). Colocalization of SV2 with GFP-TTC staining was only observed in a very limited number of areas. Scale bar: 8 μm.

(C) Treatment with *botulinum* type-A neurotoxin to block synaptic vesicles exocytosis and endocytosis. 48 hours after BoTx/A injection (as described in material and methods), GFP-TTC, associated or not with 50 ng BDNF, was injected in LAL muscle and GFP fluorescence quantified as previously. **P<0.005; t-test, vs control; *P<0.005; t-test vs BoTx/A treatment.

(D) Comparison of KCl induced depolarization and BDNF effects on GFP-TTC localization at the NMJ.

FIG. 10 depicts the localization of GFP-TTC probe in lipid microdomains.

(A) 2 hours after intramuscular injection, GFP-TTC was found in detergent resistant membranes (DRMs) (lanes 4-6) isolated from gastrocnemius muscle, which also contained the raft marker caveolin-3. A small amount of GFP-TTC was also detected in the soluble fraction (lane 12).

(B) Left three columns of panels: GFP-TTC colocalized with the raft marker GM1 at the NMJ. NMJ were identified by Alexa 647-a-BTX binding (in blue). Whereas GFP-TTC was detected in less than 5 min at the NMJ, CT-b requires 3-5 hours. At this time, a diffuse staining which colocalized with the similar GFP-TTC labeling, was obtained, while a few patches labeling only for CT-b were also observed. Right column of panels: (C) Intensity profiles of GFP-TTC (green) and Alexa 594 labeled-CT-b (red) were performed 5 or 24 h after intramuscular co-injection of both probes in gastrocnemius.

Scale bar: 5 μm.

FIG. 11 shows a comparison of GFP-TTC and CT-b localization in motoneuron cell bodies. Twenty four hours after β-gal-TTC (A) or GFP-TTC and CT-b (B-E) intramuscular injection in gastrocnemius muscle, mice were perfused intracardially and their spinal cords removed. (A) X-gal reaction on spinal cord transerve sections showed labeling in motoneuron cell bodies but also in neurites (inset). (B) GFP-TTC and CT-b were detected on longitudinal section of spinal cord in a significant number of motoneurons. (C) Probes were detected in vesicles highly concentrated in cell bodies but also in neurites. (D) In neuronal extensions, GFP-TTC and CT-b were detected in different vesicular-like structures. Note that only few of them were positive for both probes. (E) Note that neither GFP-TTC nor CT-b were detected in the nucleus as shown in one optical section.

Scale bars: A, 0.2 mm; inset, 50 μm; B, 20 μm; C, 10 μm; D, 5 μm; E, 2 μm.

DETAILED DESCRIPTION

Tetanus toxin is a potent neurotoxin of 1315 amino acids that is produced by *Clostridium tetani* (1, 2). It prevents the inhibitory neurotransmitter release from spinal cord interneurons by a specific mechanism of cell intoxication (for review see ref 3). This pathological mechanism has been demonstrated to involve retrograde axonal and transynaptic transport of the tetanus toxin. The toxin is taken up by nerve endings at the neuromuscular junction, but does not act at this site; rather, the toxin is transported into a vesicular compartment and travels along motor axons for a considerable distance until it reaches its targets. The transynaptic movement of tetanus toxin was first demonstrated by autoradiographic localization in spinal cord interneurons after injection into a muscle (4). However, previous studies of transynaptic passage of tetanus toxin from motoneurons were limited by the rapid development of clinical tetanus and death of the experimental animal (4, 5, 6).

A fragment of tetanus toxin obtained by protease digestion, the C fragment, has been shown to be transported by neurons in a similar manner to that of the native toxin without causing clinical symptoms (7, 8, 9, 10). A recombinant C fragment was reported to possess the same properties as the fragment obtained by protease digestion (11). The fact that an atoxic fragment of the toxin molecule was able to migrate retrogradely within the axons and to accumulate into the CNS led to speculation that such a fragment could be used as a neurotrophic carrier (12). A C fragment chemically conjugated to various large proteins was taken up by neurons in tissue culture (13) and by motor neurons in animal models (ref. 12, 14, and 15). According to the invention the fragment of tetanus toxin consists of a non-toxic proteolytic fragment of tetanus toxin (TT) comprising a fragment C and a fragment B or a fraction thereof of at least 11 amino acid residues or a non-toxic proteolytic fragment of tetanus toxin (TT) comprising a fragment C and a fragment B or a fraction thereof of at least 11 amino acids residues and a fraction of a fragment A devoid of its toxic activity corresponding to the proteolytic domain having a zinc-binding motif located in the central part of the chain between the amino acids 225 and 245 (cf. Montecucco C. and Schiavo G. Q. Rev. Biophys., (1995), 28:423472). Thus the fraction of the fragment A comprises, for example, the amino acid sequence 1 to 225 or the amino acid sequence 245 to 457, or the amino acid sequence 1 to 225 associated with amino acid sequence 245 to 457.

The molecule having a biological function is selected from the group consisting of protein of interest, for example, for the compensation or the modulation of the functions under the control of the CNS or the spinal cord or the modulation of the functions in the CNS or the spinal cord, or protein of interest to be delivered by gene therapy expression system to the CNS or the spinal cord. The proteins of interest are, for example, the protein SMN implicated in spinal muscular atrophy (Lefebvre et al., Cell, (1995), 80:155-165 and Roy et al., Cell, (1955), 80:167-178); neurotrophic factors, such as BDNF (Brain-derived neurotrophic factor); NT-3 (Neurotrophin-3); NT4/5; GDNF (Glial cell-line-derived neurotrophic factor); IGF (Insulin-like growth factor) (Oppenheim, Neuron, (1996), 17:195-197; Thoenen et al., Exp. Neurol., (1933), 124:47-55 and Henderson et al., Adv. Neurol., (1995), 68:235-240); or PNI (protease nexin I) promoting neurite outgrowth (this factor can be used for the treatment of Alzheimer disease (Houenou et al., PNAS, (1995), 92:895-899)); or SPI3 a serine protease inhibitor protein (Safaei, Dev. Brain Res., (1997), 100: 5-12); or ICE (Interleukin-1β converting Enzyme) a factor implicated in apoptosis, to avoid apoptosis (Nagata, Cell, (1997), 88:355-365); or Bcl-2, a key intracellular regulator of programmed cell death (Jacobson, M. D. (1997), Current Biology, 7:R277-R281); or green fluorescent protein (Lang et al., Neuron, (1997), 18:857-863) as a marker; enzyme (ex: β-Gal); endonuclease like 1-SceI (Choulika A., et al. (1995), Molecular and Cellular biology, 15 (4):1968-

1973 or CRE (Gu H., et al. (1994), Science, 265:103-106); specific antibodies; drugs specifically directed against neurodegenerative diseases such as latero spinal amyotrophy. Several molecules can be associated with a TT fragment.

In association means an association obtained by genetic recombination. This association can be realized upstream as well as downstream to the TT fragment. The preferred mode of realization of the invention is upstream and is described in detail; a downstream realization is also contemplated. (Despite Halpern et al., J. Biol. Chem., (1993), 268(15):11188-11192, who indicated that the carboxyl-terminal amino acids contain the domain required for binding to purified gangliosides and neuronal cells.)

The desired CNS area means, for example, the tongue which is chosen to direct the transport to hypoglossal motoneuron; the arm muscle which is chosen to direct the transport to the spinal cord motoneurons.

For this realization of transplantation of a neuron to the CNS or the spinal cord see Gage, F. H. et al. (1987), Neuroscience, 23:725-807, "Grafting genetically modified cells to the brain: possibilities for the future."

The techniques for introducing the polynucleotides to cells are described in U.S. Pat. Nos. 5,580,859 and 5,589,466, which is relied upon and incorporated by reference herein. For example, the nucleotides may be introduced by transfection in vitro before reimplantation in area of the CNS or the spinal cord.

A chemical linkage is considered for a particular embodiment of the invention and comprises the association between the TT fragment and a polynucleotide encoding the molecule of interest with its regulatory elements, such as promoter and enhancer capable of expressing said polynucleotide. Then the TT fragment allows the retrograde axonal transport and/or the transynaptic transport, and the product of the polynucleotide is expressed directly in the neurons. This chemical linkage can be covalent or not, but preferably covalent performed by thiolation reaction or by any other binding reaction as described in "Bioconjugate Techniques" from Gret T. Hermanson (Academic press, 1996).

The axonal retrograde transport begins at the muscle level, where the composition of interest is taken up at the neuromuscular junction, and migrates to the neuronal body of the motoneurons (which are also called the first order neurons) in the CNS or spinal cord. First order neurons mean neurons that have internalized the composition of interest, and thus in this case, correspond to motoneurons.

The transynaptic retrograde transport corresponds to interneuron communications via the synapses from the motoneurons, and comprises second order neurons and higher order neurons (fourth order corresponding to neurons in the cerebral cortex).

The different stages of the neuronal transport are through the neuromuscular junction, the motoneuron, also called first order neuron, the synapse at any stage between the neurons of different order, neuron of order second to fourth order, which corresponds to the cerebral cortex.

In one embodiment of this invention, it is shown that a β-gal-TTC (TT-fragment C) hybrid protein retains the biological activities of both proteins in vivo. Therefore, the hybrid protein can undergo retrograde and transneuronal transport through a chain of interconnected neurons, as traced by its enzymatic activity. These results are consistent with those of others who used chemically conjugated TTC, or TTC fused to other proteins (12, 13, 14, 15). In these in vitro analyses, the activity of the conjugated or hybrid proteins was likewise retained or only weakly diminished. Depending on the nature of the TTC fusion partner, different types of potential applications can be envisioned. For example, this application can be used to deliver a biologically active protein into the CNS for therapeutic purposes. Such hybrid genes can also be used to analyze and map synaptically connected neurons if reporters, such as lacZ or the green fluorescent protein (GFP; 29) gene, were fused to TTC.

The retrograde transport of the hybrid protein may be demonstrated as follows. When injected into a muscle, β-gal activity rapidly localized to the somata of motoneurons that innervate the muscle. The arborization of the whole nerve, axon, somata and dendrites can easily be visualized. However, in comparison to the neurotropic viruses, the extent of retrograde transneuronal transport of the hybrid protein from the hypoglossal neurons indicates that only a subset of interconnected neurons is detected, although most areas containing second-order interneurons have been identified by the β-gal-TTC marker. Transneuronal uptake is mostly restricted to second order neurons. In such experiments, when a limited amount of a neuronal tracer is injected into a muscle or cell, only a fraction will be transported through a synapse, thereby imposing an experimental constraint on its detection. Presently, the most efficient method, in terms of the extent of transport, relies on neurotropic viruses. Examples include: alpha-herpes viruses, such as herpes simplex type 1 (HSV-1), pseudorabies virus (PrV), and rhabdoviruses (24, 25). Viral methods are very sensitive because each time a virus infects a new cell, it replicates, thereby amplifying the signal and permitting visualization of higher order neurons in a chain. Ultimately, however, one wants to map a neuronal network in an in vivo situation such as a transgenic animal. Here, the disadvantage of viral labeling is its potential toxicity. Most viruses are not innocuous for the neural cell, and their replication induces a cellular response and sometimes cell degeneration (24). Furthermore, depending on experimental conditions, budding of the virus can occur leading to its spread into adjoining cells and tissues.

Differences in mechanisms of transneuronal migration could also account for the restricted number of neurons labeled by β-gal-TTC. Matteoli et al have provided strong evidence that the intact tetanus toxin crosses the synapses by parasitizing the physiological process of synaptic vesicle recycling at the nerve terminal (22). The toxin probably binds to the inner surface of a synaptic vesicle during the time the lumen is exposed to the external medium. Vesicle endocytosis would then presumably provide the mechanism for internalization of the toxin. Because the TTC fragment is known to mimic the migration of the toxin in vivo, it could therefore direct the fusion protein along a similar transynaptic pathway. If this hypothesis is confirmed, it would strongly suggest that synaptic activity is required for the transneuronal transport of β-gal-TTC. Therefore, only active neuronal circuits would be detected by the hybrid protein. The possible dependence of β-gal-TTC on synaptic vesicle exocytosis and endocytosis could be further investigated, since techniques are now available to record synaptic activity in neural networks in vitro (30). In contrast, the transneuronal pathway of neurotropic viruses has not yet been elucidated and could be fundamentally different, involving virus budding in the vicinity of a synapse. Finally, the transneuronal transport of the hybrid protein might depend on a synaptic specificity, although the tetanus toxin is not known to display any (7, 23). It is therefore likely that a virus would cross different or inactive synapses. In summary, the restricted spectrum of interneuronal transport, in addition to its non-toxicity, make the β-gal-TTC hybrid protein a novel and powerful tool for analysis of neural pathways.

One advantage of the fusion gene of the invention for neuronal mapping is that it derives from a single genetic entity that is amenable to genetic manipulation and engineering. Several years ago, a technique based on homologous recombination in embryonic stem cells was developed to specifically replace genes in the mouse (31, 32). This method generates a null mutation in the substituted gene, although in a slightly modified strategy, a dicistronic messenger RNA can also be produced (33, 34). When a reporter gene, such as *E. coli* lacZ, is used as the substituting gene, this technique provides a means of marking the mutated cells so that they can be followed during embryogenesis. Thus, this technique greatly simplifies the analysis of both the heterozygote expression of the targeted gene as well as the phenotype of null (homozygous) mutant animals.

Another advantage of this invention is that the composition comprising the fusion gene may encode an antigen or antigens. Thus, the composition may be used to elicit an immune response in its host and subsequently confer protection of the host against the antigen or antigens expressed. These immunization methods are described in Robinson et al., U.S. Pat. No. 5,43,578, which is herein incorporated by reference. In particular, the method of immunizing a patient or animal host comprises introducing a DNA transcription unit encoding comprising the fusion gene of this invention, which encodes a desired antigen or antigens. The uptake of the DNA transcription unit by the host results in the expression of the desired antigen or antigens and the subsequent elicitation of humoral and/or cell-mediated immune responses.

Neural cells establish specific and complex networks of interconnected cells. If a gene were mutated in a given neural cell, we would expect this mutation to have an impact on the functions of other, interconnected neural cells. With these considerations in mind, a genetic marker that can diffuse through active synapses would be very useful in analyzing the effect of the mutation. In heterozygous mutant animals, the cells in which the targeted gene is normally transcribed could be identified, as could the synaptically connected cells of a neural network. In a homozygous animal, the impact of the mutation on the establishment or activity of the neural network could be determined. The feasibility of such an in vivo approach depends critically on the efficiency of synaptic transfer of the fusion protein, as well as its stability and cellular localization.

Another extension of the invention is to gene therapy applied to the CNS. This invention provides for uptake of a non-toxic, enzyme-vector conjugate by axon terminals and conveyance retrogradely to brainstem motoneurons. A selective retrograde transynaptic mechanism subsequently transports the hybrid protein into second-order connected neurons. Such a pathway, which by-passes the blood-brain barrier, can deliver macromolecules to the CNS. In fact, pathogenic agents, such as tetanus toxin and neurotropic viruses, are similarly taken up by nerve endings, internalized, and retrogradely transported to the nerve cell somata. In such a scenario, the lacZ reporter would be replaced by a gene encoding a protein that provides a necessary or interesting activity and/or function. For example, the human CuZn superoxide dismutase, SOD-1, and the human enzyme β-N-acetylhexosaminidase A, HexA, have been fused or chemically coupled to the TTC fragment (13, 16), and their uptake by neurons in vitro was considerably increased and their enzymatic functions partially conserved. Combined with the in vivo experiments described here using β-gal-TTC, a gene therapy approach based on TTC hybrid proteins appears to be a feasible method of delivering a biological function to the CNS. However, ways have to be found to target the TTC hybrid proteins, which are likely to be sequestrated into vesicles, to the appropriate subcellular compartment. Such a therapeutic strategy could be particularly useful for treating neurodegenerative and motoneuron diseases, such as amyotrophy lateral sclerosis (ALS, 35), spinal muscular atrophies (SMA, 36, 37), or neurodegenerative lysosomal storage diseases (38, 39). Injection into selected muscles, even in utero, could help to specifically target the appropriate neurons. In addition, such an approach would avoid the secondary and potentially toxic effects associated with the use of defective viruses to deliver a gene (40, 41).

EXAMPLE 1

Figure 4:
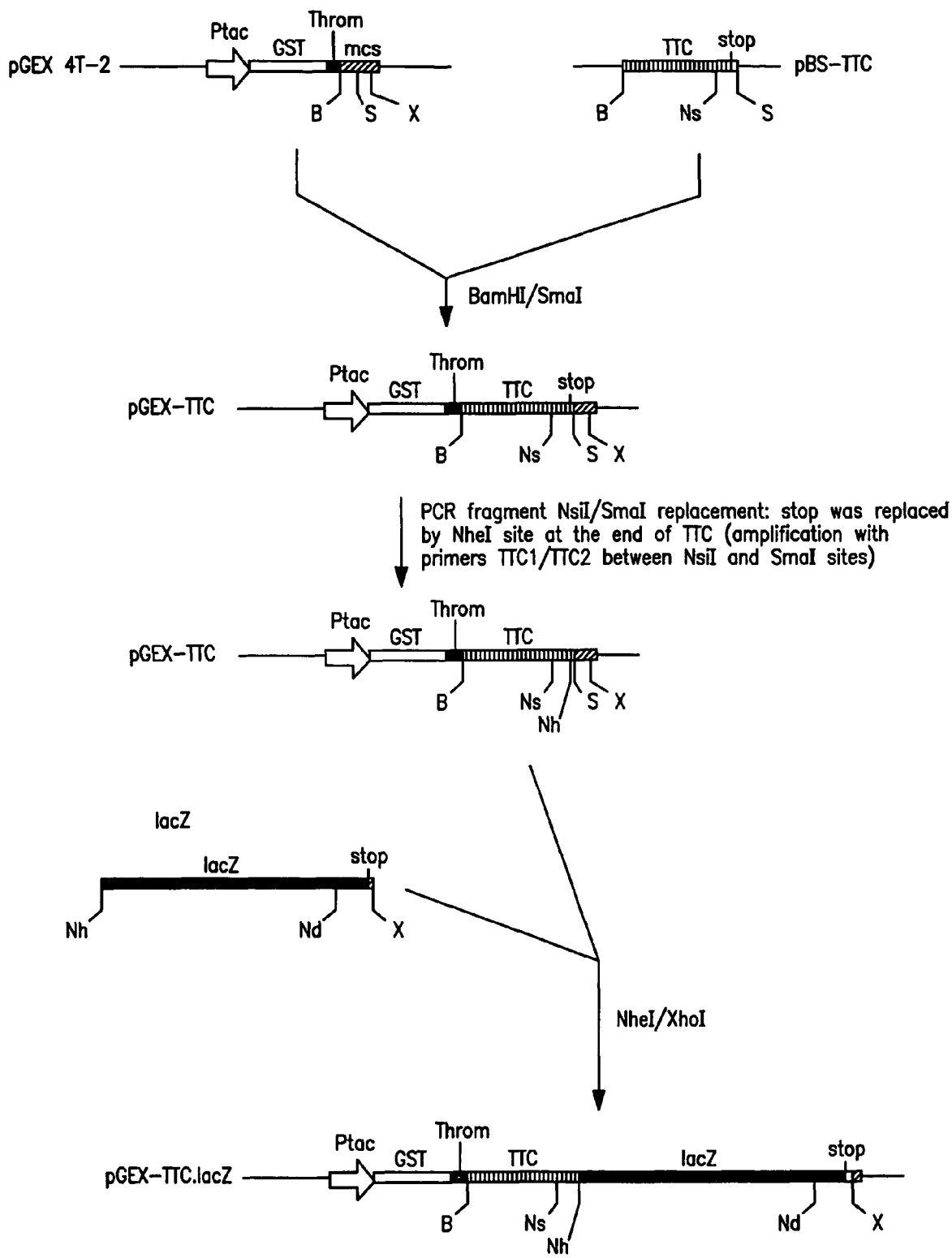
FIG. 4 shows construct pGEX:TTC-lacZ.
Figure 5:
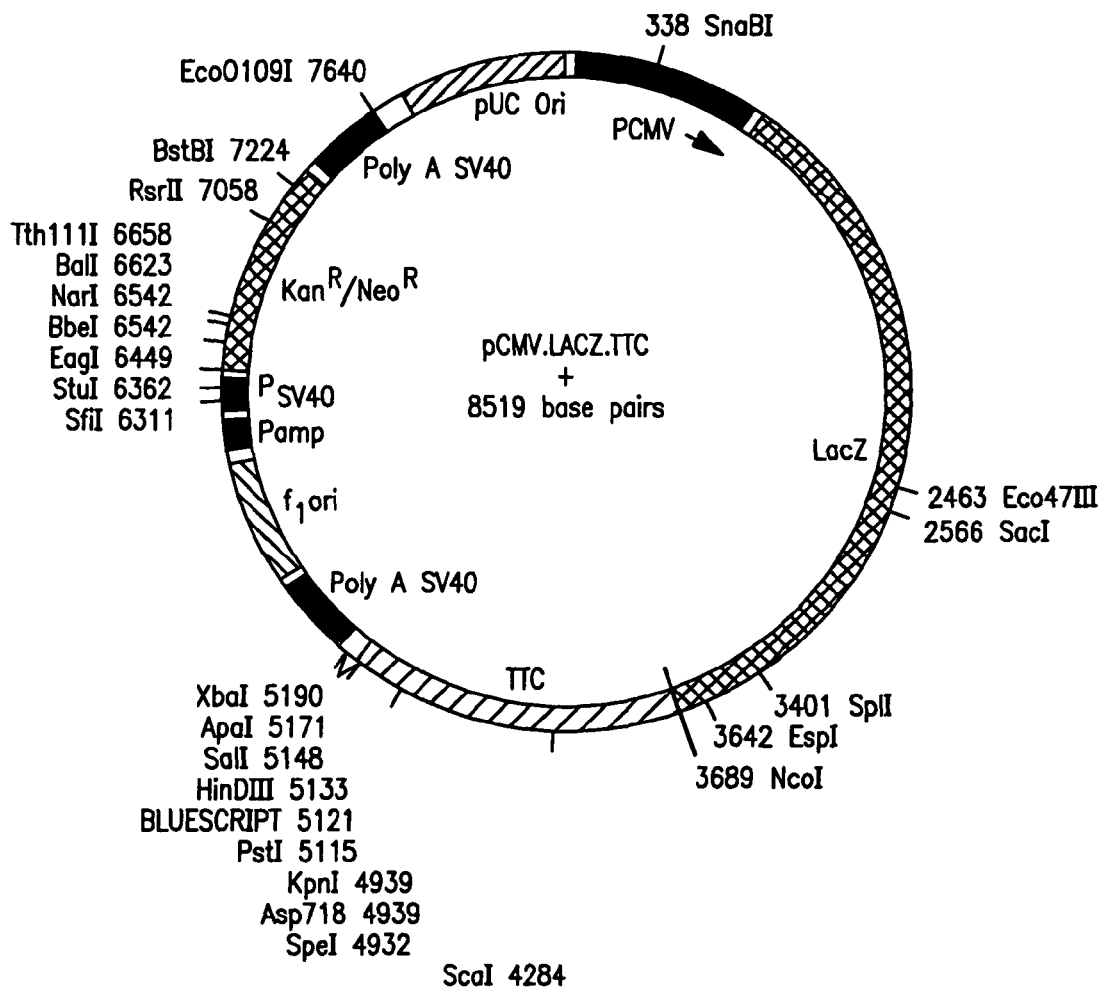
FIG. 5 depicts the details of the construct pCMV:lacZ-TTC.

Plasmid Constructions (A) TTC Cloning:

Full length TTC DNA was generated from the genomic DNA from the *Clostridium Tetani* strain (a gift from Dr. M. Popoff, Institut Pasteur) using PCR. Three overlapping fragments were synthesized: PCR1 of 465 bp (primer 1: 5'-CCC CCC GGG CCA CCA TGG TTT TTT CAA CAC CAA TTC CAT TTT CTT ATT C-3' (SEQ ID NO:4) and primer 2: 5'-CTA AAC CAG TAA TTT CTG-3' (SEQ ID NO:5)), PCR2 of 648 bp (primer 3: 5'-AAT TAT GGA CTT TAA AAG ATT CCG C-3' (SEQ ID NO:6) and primer 4: 5'-GGC ATT ATA ACC TAC TCT TAG AAT-3' (SEQ ID NO:7)) and PCR3 of 338 bp (primer 5: 5'-AAT GCC TTT AAT AAT CTT GAT AGA AAT-3' (SEQ ID NO:8) and primer 6: 5'-CCC CCC GGG CAT ATG TCA TGA ACA TAT CAA TCT GTT TAA TC-3' (SEQ ID NO:9)). The three fragments were sequentially introduced into pBluescript KS+ (Stratagene) to give pBS:TTC plasmid. The upstream primer 1 also contains an optimized eukaryotic Ribosome Binding Site (RBS) and translational initiation signals. Our TTC fragment (462 amino acids) represents the amino acids 854-1315 of tetanus holotoxin, i.e. the carboxy-terminal 451 amino acids of the heavy chain, which constitute the fragment C plus 11 amino acids of the heavy chain that immediately precede the amino terminus of the fragment C. The DNA sequence and amino acid sequence of the TTC fragment cloned in pBS:TTC is shown in FIG. 1. The construct pBS:TTC is shown in FIG. 2.

(B) pGEX:lacZ-TTC:

pGEX:lacZ was obtained by cloning a SmaI/XhoI lacZ fragment from the pGNA vector (a gift from Dr. H. Le Mouellic) into pGEX 4T-2 (Pharmacia). PCR was used to convert the lacZ stop codon into an NcoI restriction site. Two primers (upstream: 5'-CTG AAT ATC GAC GGT TTC CAT ATG-3' (SEQ ID NO:10) and downstream: 5'-GGC AGT CTC GAG TCT AGA CCA TGG CTT TTT GAC ACC AGA C-3' (SEQ ID NO:11)) were used to amplify the sequence between NdeI and XhoI, generating pGEX:lacZ(NcoI) from pGEX:lacZ. pGEX:lacZ-TTC was obtained by insertion of the TTC NcoI/XhoI fragment into pGEX:lacZ(NcoI), fusing TTC immediately downstream of the lacZ coding region and in the same reading frame. FIG. 3 shows the details of the pGEX:lacZ-TTC construct.

(C) pGEX:TTC-lacZ:

pBS:TTC was modified to change NcoI into a BamHI restriction site (linker 5'-CAT GAC TGG GGA TCC CCA GT-3' (SEQ ID NO:12)) at the start of the TTC DNA, to give pBS:TTC(BamHI) plasmid. pGEX:TTC was obtained by cloning The TTC BamHI/SmaI fragment from pBS:TTC (BamHI) into pGEX 4T-2 (Pharmacia). PCR was used to convert the TTC stop codon into an NheI restriction site. Two primers (upstream: 5'-TAT GAT AAA AAT GCA TCT TTA GGA-3' (SEQ ID NO:13) and downstream: 5'-TGG AGT CGA CGC TAG CAG GAT CAT TTG TCC ATC CTT C-3' (SEQ ID NO:14)) were used to amplify the sequence between NsiI and SmaI, generating pGEX:TTC(NheI) from pGEX: TTC. The lacZ cDNA from plasmid pGNA was modified in its 5' extremity to change SacII into an NheI restriction site (linker 5'-GCT AGC GC-3' (SEQ ID NO:15)). pGEX:TTC-lacZ was obtained by insertion of the lacZ NheI/XhoI fragment into pGEX:TTC(NheI), fusing lacZ immediately downstream of the TTC coding region and in the same reading frame. The details of the construct of pGEX:TTC-lacZ are shown in FIG. 4.

(D) pCMV:lacZ-TTC:

pCMV vector was obtained from pGFP-C1 (Clontech laboratories) after some modifications: GFP sequence was deleted by a BglII/NheI digestion and relegation, and SacII in the polylinker was converted into an AscI restriction site (linkers 5'-GAT ATC GGC GCG CCA GC-3' (SEQ ID NO:16) and 5'-TGG CGC GCC GAT ATC GC-3' (SEQ ID NO:17)).

pBluescript KS+ (Stratagene) was modified to change XhoI into an AscI restriction site (linker 5'-TCG ATG GCG CGC CA-3' (SEQ ID NO:18)), giving pBS(AscI) plasmid. pBS:lacZ-TTC was obtained by cloning a XmaI lacZ-TTC fragment from pGEX:lacZ-TTC into pBS(AscI). pCMV: lacZ-TTC was obtained by insertion of the lacZ-TTC XmnI/AscI fragment into pCMV vector at the XhoI and AscI sites (XhoI and XmnI was eliminated with the clonage), putting the fusion downstream of the CMV promotor. FIG. 8 shows the details of the construct pCMV:lacZ-TTC. Plasmid pCMV:lacZ-TTC was deposited on Aug. 12, 1997, at the Collection Nationale de Cultures de Microorganisms (CNCM), Institut Pasteur, 25, Rue de Docteur Roux, F-75724, Paris Cedex 15, France, under Accession No. I-1912.

EXAMPLE 2

Purification of the Hybrid Protein

The *E. coli* strain SR3315 (a gift from Dr. A. Pugsley, Institut Pasteur) transfected with pGEX:lacz-TTC was used for protein production. An overnight bacterial culture was diluted 1:100 in LB medium containing 100 µg/ml ampicillin, and grown for several hours at 32° C. until an OD of 0.5 was reached. Induction from the Ptac promoter was achieved by the addition of 1 mM IPTG and 1 mM $MgCl_2$ and a further 2 hrs incubation. The induced bacteria were pelleted by centrifugation for 20 min at 3000 rpm, washed with PBS and resuspended in lysis buffer containing 0.1 M Tris pH 7.8, 0.1M NaCl, 20% glycerol, 10 mM EDTA, 0.1% Triton-X100, 4 mM DTT, 1 mg/ml lysosyme, and a mixture of anti-proteases (100 µg/ml Pefablok, 1 µg/ml leupeptin, 1 µg/ml pepstatin, 1 mM benzamidine). After cell disruption in a French Press, total bacterial lysate was centrifuged for 10 min at 30000 rpm. The resulting supernatant was incubated overnight at 4° C. with the affinity matrix Glutathione Sepharose 4B (Stratagene) with slow agitation. After centrifugation for 5 min at 3000 rpm, the matrix was washed three times with the same lysis buffer but without lysosyme and glycerol, and then three times with PBS. The resin was incubated overnight at 4° C. with Thrombin (10 U/ml; Sigma) in PBS in order to cleave the β-gal-TTC fusion protein from the Glutatione-S-transferase (GST) sequence and thereby elute it from the affinity column. Concentration of the eluted fusion protein was achieved by centrifugation in centricon X-100 tubes (Amicon; 100,000 MW cutoff membrane).

Purified hybrid protein was analyzed by Western blotting after electrophoretic separation in 8% acrylamide SDS/PAGE under reducing conditions followed by electrophoretic transfer onto nitrocellulose membranes (0.2 mm porosity, Bio-Rad). Immunodetection of blotted proteins was performed with a Vectastaln ABC-alkaline phosphatase kit (Vector Laboratories) and DAB color development. Antibodies were used as follows: rabbit anti-β-gal antisera (Capel), dilution 1:1000; rabbit anti-TTC antisera (Calbiochem), dilution 1:20000. A major band with a relative molecular mass of 180 kDa corresponding to the β-Gal-TTC hybrid protein was detected with both anti-β-Gal anti-TTC antibodies.

EXAMPLE 3

Binding and Internalization of Recombinant Protein in Differentiated 1009 Cells

The 1009 cell line was derived from a spontaneous testicular teratocarcinoma arising in a recombinant inbred mouse strain (129×B6) (17). The 1009 cells were grown in Dulbecco's modified Eagle's medium (DMEM) containing 10% fetal calf serum and passaged at subconfluence. In vitro differentiation with retinoic acid and cAMP was performed as described (18). Eight days after retinoic acid treatment, cells were used for the internalization experiments with either the hybrid protein or β-gal.

Binding and internalization of the β-Gal-TTC fusion were assessed using a modified protocol (16). Differentiated 1009 cells were incubated for 2 hrs at 37° C. with 5 µg/ml of p-Gal-TTC or p-Gal protein diluted in binding buffer (0.25% sucrose, 20 mM Tris acetate 1 mM CaCl2, 1 mM $MgCl_2$, 0.25% bovine serum albumin, in PBS). The cells were then incubated with 1 µg/ml Pronase E (Sigma) in PBS for 10 min at 37° C., followed by washing with proteases inhibitors diluted in PBS (100 µg/ml Pefablok, 1 mM benzamidine).

The cells were fixed with 4% formalin in PBS for 10 min at room temperature (RT) and then washed extensively with PBS. β-gal activity was detected on fixed cells by an overnight staining at 37° C. in X-Gal solution (0.8 mg/ml X-Gal, 4 mM potassium ferricyanide, 4 mM potassium ferrocyanide, 4 mM $MgCl_2$ in PBS). For electron microscopy, the cells were further fixed in 2.5% glutaraldehyde for 18 hrs, and then processed as described (19).

For immunohistochemical labeling, cells were fixed with 4% paraformaldehyde in PBS for 10 min at RT then washed extensively with PBS, followed by a 1 hr incubation at RT with 2% BSA/0.02% Triton X-100 in PBS. Cells were co-incubated in primary antibodies diluted in 2% BSA/0.02% Triton X-100 in PBS for 2 hrs at RT. Antibodies used were a mouse anti-neurofilament antibody (NF 200 Kd, dilution 1:50; Sigma) or the rabbit anti-TTC antibody (dilution 1:1000). The labeling was visualized using fluorescent secondary antibodies: Cy3, goat anti-rabbit IgG (dilution 1:500; Amersham) or anti-mouse IgG with extravidin-FITC (dilution 1:200; Sigma). Cells were mounted in moviol and visualized with epifluorescence.

EXAMPLE 4

In Vivo Recombinant Protein Injection 14-week old B6D2 µl mice were obtained from IFFA-CREDO. The animal's tongue muscle was injected using an Hamilton syringe (20 µl per animal) while under general anesthesia with 3% Avertin (15 µl/g of animal). The protein concentration was 0.5 to 5 µg/µl in PBS; therefore, mice received approximately 10 to 100 µg per injection. Animals were kept alive for 12 hrs to 48 hrs post-injection to permit migration of the injected protein, and in no case were any tetanus symptoms detected. The mice were sacrificed by intracardiac perfusion with 4% paraformaldehyde in PBS while under deep anesthesia. Brains were harvested, rinsed in PBS and incubated in 15% sucrose overnight at 4° C., then mounted in tissue-tek before sectioning, 15 µm thick slices using a cryostat.

EXAMPLE 5

Histology, Immunohistology, and X-Gal Staining

For in toto X-Gal staining of the dissected brain and tongue, mice (10 animals) were sacrificed and fixed as described above. The brain was further cut with a scalpel along a median plane and directly incubated for 12 hrs in X-Gal solution.

For immunohistology, sections were incubated In a 1:5000 dilution of anti-TTC antibody in 2% BSA/0.02% Triton X-100 in PBS overnight at 4° C. after nonspecific antibody binding sites were blocked by a 1 hr incubation in the same buffer. Antibody detection was carried out using the Vectastain ABC-alkaline phosphatase kit with DAB color development. For X-Gal staining, sections were incubated in X-Gal solution and counterstained for 30 sec with hematoxylin 115 (v/v) in PBS. Histology on adjacent sections was done after X-Gal staining, using a 30 sec incubation in hematoxylin/thionin solution. All sections were mounted in moviol before eight microscopy analysis.

EXAMPLE 6A

Internalization of the β-gal-TTC Fusion Protein by Neurons In Vitro

Differentiation of 1009 cells with retinoic acid and cAMP in vitro yields neuronal and glial cells (18, 20). X-Gal staining or immunolabeling were performed after incubation with the β-gal-TTC fusion protein or with either the β-gal or TTC proteins alone. Only when the hybrid protein was incubated with differentiated 1009 cells was a strong X-Gal staining detected in cells having a neuronal phenotype. No signal was detected when β-gal alone was incubated under the same conditions. A similar X-Gal staining pattern was obtained after pronase treatment of the cells to remove surface bound proteins, indicating that the hybrid protein had been internalized. The intracellular localization of the hybrid protein was further confirmed by electron microscopic analysis of X-Gal-stained cells. Furthermore, the enzymatic activity observed in axons seemed to be localized in vesicles associated with filaments, which is in agreement with previous work on TTC fragment or native tetanus toxin (14, 21, 22). Co-labeling with anti-TTC and anti-neurofilament antibodies revealed that β-gal activity co-localized with TTC fragment in neuronal cells. No glial cells were labeled with either antibody.

EXAMPLE 6B

Internalization of the TTC-β-gal Fusion Protein by Neurons In Vitro

The method used for the internalization was identical to that described in Example 6 above. The results show efficiently internalization of the hybrid as in Example 6 above.

EXAMPLE 7

Retrograde Transport of the Hybrid Protein In Vivo

To study the behavior of the β-gal-TTC protein in vivo, the hybrid protein was tested in a well characterized neuronal network, the hypoglossal system. After intramuscular injection of β-gal-TTC protein into the mouse tongue, the distribution of the hybrid protein in the CNS was analyzed by X-Gal staining. Various dilutions of the protein were injected and sequential time points were analyzed to permit protein transport into hypoglossal motoneurons (XII), and its further transneuronal migration into connected second order neurons.

A well-defined profile of large, apparently retrogradely labeled neurons was clearly evident in the hypoglossal structure, analyzed in toto at 12 hrs post-injection. A strong labeling was also apparent in the hypoglossal nerve (XIIn) of the tongue of the injected mice. At the level of muscle fibers, button structures were observed that might reflect labeling of neuromuscular junctions where the hybrid protein was internalized into nerve axons. These data demonstrate that the β-gal-TTC hybrid protein can migrate rapidly by retrograde axonal transport as far as motoneuron cell bodies, after prior uptake by nerve terminals in the tongue. This specific uptake and the intraaxonal transport are similar to the properties that have been described for the native toxin (6, 21, 23).

Transport of the hybrid protein was examined in greater detail by analyzing X-Gal-stained brain sections. Motoneurons of the hypoglossal nucleus became labeled rapidly, with 12 hrs being the earliest time point examined. Most of the label was confined to neuronal somata, the cell nuclei being unlabeled. The intensity of the labeling depends upon the concentration of the β-gal-TTC protein injected: when 10 µg of protein was injected, only the hypoglossal somata were detected, whereas with 25 to 50 µg a fuzzy network of dendrites was visualized; transynaptic transfer was detected with 100 µg of hybrid protein. An identical distribution of label was observed then brain sections were immunostained with an anti-TTC antibody, demonstrating that β-gal and TTC fragment co-localize within cells. Finally, injection of β-gal alone did not result in labeling of the hypoglossal nuclei and therefore confirms that transport of the hybrid protein is TTC-dependent. Labeling with an anti-TTC antibody was less informative than detection of β-gal activity; for instance, the nerve pathway to the brain could not be visualized by anti-TTC immunostaining. At 18 hrs post-injection, labeling was observed in the hypoglossal nuclei: all motoneuron cell bodies and the most proximal part of their dendrites were very densely stained. In contrast, no labeling was ever detected in glial cells adjoining XII motoneurons or their axons. Our results are in accordance with others who reported an identical pattern of immunolabeling after injection of the TTC fragment alone (9). Transneuronal transfer is detectable after 24 hrs. An additional 24 hrs and beyond did not yield a different staining.

EXAMPLE 8

Transneuronal Transport of the Hybrid Protein

Second order interneurons, as well as higher order neurons that synapse with the hypoglossal motoneurons, have been extensively analyzed using conventional markers, such as the wheat germ agglutinin-horseradish peroxidase complex (WGA-HRP) or neurotropic viruses such as alpha-herpes (24) and rhabdoviruses (25). An exhaustive compilation of regions in the brain that synaptically connect to the hypoglossal nucleus has also been described recently (25). In this invention, the distribution of the β-gal-TTC fusion depended on the initial concentration of protein injected into the muscle and the time allowed for transport after injection. Up to 24 hrs post-injection, labeling was restricted to the hypoglossal nuclei. After 24 hrs, the distribution of second order transneuronally labeled cells in various regions of the brain was consistent and reproducible. Even at longer time points (e.g. 48 hrs), labeling of the hypoglossal nucleus remained constant. At higher magnification, a discrete and localized staining of second-order neurons was observed, suggesting that the hybrid protein had been targeted to vesicles within cell somata, synapses and axons. A similar patchy distribution was previously described for tetanus toxin and TTC fragment alone (14, 21, 22).

Intense transneuronal labeling was detected in the lateral reticular formation (LRF), where medullary reticular neurons have been reported to form numerous projections onto the hypoglossal nucleus (26, 27). β-gal activity was detected bilaterally in these sections. Label led LRF projections formed a continuous column along the rostrocaudal axis, beginning lateral to the hypoglossal nucleus, with a few neurons being preferentially stained in the medullary reticular dorsal (MdD) and the medullary reticular ventral (MdV) nuclei. This column extends rostrally through the medulla, with neurons more intensely labeled in the parvicellular reticular nucleus (PCRt, caudal and rostral). After 48 hrs, cells in MdD and PCRt were more intensely stained. A second bilateral distribution of medullary neurons projecting to the hypoglossal nucleus was detected in the solitary nucleus (Sol) but the labeling was less intense than in the reticular formation, presumably because relatively few cells of the solitary nucleus project onto the hypoglossal nucleus (26). However, no labeling was found in the spinal trigeminal nucleus (Sp5), which has also been shown to project onto the hypoglossal nucleus (26). Transynaptic transport of the β-gal-TTC protein was also detected in the pontine reticular nucleus caudal (PnC), the locus coeruleus (LC), the medial vestibular nucleus (MVe) and in a few cells of the inferior vestibular nucleus (IV). These cell groups are known to project onto the hypoglossal nucleus (25), but their labeling was weak, probably because of the greater length of their axons. A few labeled cells were observed in the dorsal paragigantocellular nucleus (DPGi), the magnocellular nucleus caudal (RMc), and the caudal raphe nucleus (R); their connections to the hypoglossal nucleus have also been reported (25). Finally, labeled neurons were detected bilaterally in midbrain projections, such as those of the mesencephalic trigeminal nucleus (Me5), and a few neurons were stained in the mesencephalic central gray region (CG). These latter nuclei have been typed as putative third order cell groups related to the hypoglossal nucleus (25).

Neurons in the motor trigeminal nucleus (Mo5) and the accessory trigeminal tract (Acs5) were also labeled, along with a population of neurons in the facial nucleus (N7). However, interpretation of this labeling is more ambiguous, since it is known that motoneurons in these nuclei also innervate other parts of the muscular tissue, and diffusion of the hybrid protein might have occurred at the point of injection. Conversely, these nuclei may have also projected to the tongue musculature via nerve XII, since neurons in N7 have been reported to receive direct hypoglossal nerve input (28). This latter explanation is consistent with the fact that labeling in these nuclei was detected only after 24 hrs; however, this point was not further investigated.

Together, the data summarized in Table 1 clearly establish transneuronal transport of the β-gal-TTC fusion protein from the hypoglossal neurons into several connected regions of the brainstem.

TABLE 1

Transneuronal transport of the lacZ-TTC fusion from the XII nerve: labeling of different cells types in the central nervous system.

| Cell groups | 12-18 hrs | 24-48 hrs |
|---|---|---|
| First order neurons | | |
| First category: | | |
| XII, hypoglossal motoneurons | ++ | +++ |
| Second category: | | |
| N7, facial nu | − | ++ |
| Mo5, motor trigeminal nu | − | ++ |
| Acs5, accessory trigeminal nu | − | + |
| Second order cell groups | | |
| MdD, medullary reticular nu, dorsal | − | ++ |
| MdV, medullary reticular nu, ventral | − | +/− |
| PCRt, parvicellular reticular nu, caudal | − | ++ |
| PCRt, parvicellular reticular nu, rostral | − | ++ |
| Sol, solitary tract nu | − | + |
| DPGi, dorsal paragigantocellular nu | − | +/− |
| PnC, pontine reticular nu, caudal | − | + |
| RMc, magnocellular reticular nu | − | +/− |
| R, caudal raphe nu | − | +/− |
| MVe, medial vestibular nu | − | + |
| IV, inferior vestibular nu | − | +/− |
| LC, locus coeruleus | − | + |
| Me5, mesencephalic trigeminal nu (*) | − | + |
| CG, mesenphalic central gray (*) | − | +/− |

(*) Represents second order cell groups that also contain putative third order neurons (see text).
−, no labeling;
+ to +++, increased density of label;
+/− weak labeling.
16 animals were analysed for the 12-18 hrs p.i. data;
6 animals were analysed for the 24-48 hrs p.i. data.

In another embodiment of the invention, we have constructed a fusion protein (GFP-TTC) comprising the C-terminal fragment of tetanus toxin and the GFP reporter gene, and have demonstrated its effectiveness to map a simple neural network retrogradely and transsynaptically in transgenic mice. (Maskos et al., 2002). The GFP-TTC fusion protein permits the visualization of membrane traffic at the presynaptic level of the neuromuscular junction and can be detected opticaly without immunological or enzymatic reactions. The GFP-TTC fusion protein, therefore, permits observation of active neurons with minimal disturbance of their physiological activities.

We have also previously shown that, without neural activity, localization of a TTC fusion protein at the NMJ is impaired (Miana-Mena et al., 2002). In this aspect of the invention, therefore, we investigated in vivo, the influence of neurotrophic factors on neuronal localization and internalization of GFP-TTC and the mechanisms by which certain neurotrophic factors influence neuronal trafficking in vivo. We found that localization of GFP-TTC at the NMJ is rapidly induced by neurotrophic factors such as Brain Derived Neurotrophic Factor (BDNF), Neurotrophin 4 (NT-4), and Glial-Derived Neurotrophic Factor (GDNF) but not by Nerve Growth Factor (NGF), Neurotrophin 3 (NT-3), and Ciliary Neurotrophic Factor (CNTF).

Co-injection of various amounts of BDNF with the GFP-TTC probe induces an increase of the fluorescence measured at the neuromuscular junction (NMJ). This effect, which is detectable as early as 5 min after injection and reaches a maximum level at about 30 min after injection, indicates that BDNF treatment enhances neuronal endocytosis. Among other functions, BDNF stimulates the secretion of neurotransmitter from *Xenopus* nerve muscle co-cultures and from hippocampal neurons (Lohof et al., 1993; Tyler and Pozzo-Miller, 2001). Since tetanus toxin is known to enter neurons by means of synaptic vesicle endocytosis (Matteoli et al., 1996), BDNF might increase GFP-TTC internalization through enhancement of synaptic vesicle turnover. In our study, BDNF effects persisted after BoTx/A treatment, which blocks exocytosis and endocytosis of synaptic vesicles, showing that BDNF increases the kinetics and localization of a TTC-containing fusion protein at the NMJ through another endocytic pathway. Therefore, intramuscular injection of GFP-TTC and visualization of transport mechanisms revealed at least two different endocytic pathways: a clathrin-dependent and a clathrin-independant pathway. We found that after intramuscular injection of GFP-TTC, it displayed characteristics consistent with localization in lipid rafts, including biochemical colocalization with caveolin 3 and colocalization with GM1, a raft marker identified by CT-b binding (Orlandi and Fishman, 1998; Wolf et al., 1998). Accordingly, the clathrin-independent pathway used by GFP-TTC, appears to involve lipid microdomains. Analysis by confocal microscopy revealed morphologically two different labelings. Firstly, a GFP-TTC diffuse staining, which partially overlaps with the synaptic vesicle SV2 but also with the raft marker CT-b, indicating a mixing of synaptic vesicles and lipid rafts. Secondly, highly fluorescent domains, which are detected before and persist after the more diffuse pattern and that appear to be invaginations or infoldings of the synaptic membrane. These GFP-TTC patches contained only CT-b labeling. Indeed, lipid microdomains which play a role in cellular functions such as vesicular trafficking and signal transduction (Simons and Toomre, 2000), can move laterally and cluster into larger patches (Harder et al., 1998). They might also be specific zones of exocytosis in the presynaptic compartment, undergoing a rapid form of internal traffic in response to retrograde signaling from target cells. Similar infolding and cisternae structures have been described in frog motor nerve terminals, which replenish the pool of synaptic vesicles in a manner dependent upon neuronal activity (Richards et al., 2000). In CHO cells, tubular caveolae have also been described (Mundy et al., 2002).

Based on the kinetics of probes for NMJ localization, we observed different trafficking behaviours for GFP-TTC and CT-b. It has been postulated that targeting of toxin into the cell depends on the structure and function of endogenous ganglioside receptors, which could couple toxins to specific lipid raft microdomains (Wolf et al., 1998). Thus, in vivo, endogenous or injected BDNF might increase the amount of lipid microdomains containing TTC receptors. Tetanus toxin and cholera toxin bind to different gangliosides, known as GD1b/GT1b and GM1, respectively. Hence, the difference we observed in the dynamics of recruitment at the presynaptic motor nerve terminal may be relevant to different lipid microdomains having specific glycosphingolipids and protein composition. Neuronal membranes are rich in gangliosides and different microdomains are likely to co-exist on the cell surface. Indeed, Thy-1 and PrP prion protein, two functionally different GPI proteins, are found in adjacent microdomains (Madore et al., 1999). Similarly, syntaxins are concentrated in cholesterol-dependent microdomains, which are distinct from rafts containing GPI-linked proteins (Lang et al., 2001).

Like BDNF, NT-4 was also found to increase the concentration of GFP-TTC at the NMJ, whereas NGF and NT-3 had no effect. Since the TrkB receptor is specifically activated by BDNF and NT-4, TrkB activation might be involved in this neoronal trafficking. Interestingly, high-frequency neuronal activity and synaptic transmission have been shown to elevate the number of TrkB receptors on the surface of cultured hippocampal neurons (Du et al., 2000), apparently by recruiting extra TrkB receptors to the plasma membrane (Meyer-Franke et al., 1998). Moreover, TrkB is highly enriched in lipid microdomains from neuronal plasma membrane (Wu et al., 1997). However, no specific colocalization between GFP-TTC and TrkB or p-Trk receptors were detected at the NMJ. Thus, TrkB may act indirectly on the detected traffic at the presynaptic motor nerve membrane.

It is worth noting that the TTC fragment has been detected in cultured motoneurons in the same vesicles as $p75^{NTR}$ (Lalli and Schiavo, 2002). This colocalization may be explained by the tight association of $p75^{NTR}$, which is expressed mainly during development and in pathological conditions, with GT1b ganglioside (Yamashita et al., 2002). Binding of neurotrophins to their Trk receptors leads to phosphorylation of tyrosine residues that are recognized by several intracellular signaling proteins. Such interactions lead to the activation, by means of a kinase cascade, of the MAP kinase, PI 3-kinase and phospholipase-C-γ pathways (for review see (Huang and Reichardt, 2003)). Many of the intermediates in these signaling cascades are also present in lipid rafts (Simons and Toomre, 2000; Tsui-Pierchala et al., 2002). Activation of PKA is required for translocation of activated $p75^{NTR}$ to lipid rafts (Higuchi et al., 2003). Similarly, the coreceptor GFRα1, which binds GDNF and thus allows activation of the c-RET tyrosine kinase receptor, localize to lipid rafts. GFRα1 recruits RET to lipid rafts after GDNF stimulation and results in strong and continuous signal transduction (Paratcha et al., 2001; Tansey et al., 2000).

Another neurotrophic factor, GDNF, also induced GFP-TTC localization at the NMJ. GDNF, however, activates a different receptor (i.e., a GFRα/cRET receptor) than BDNF and NT-4. Because BDNF/NT-4 and GDNF activate different receptors, we postulated that component(s) of their activation pathways may activate the trafficking of GFP-TTC receptors in specific lipid microdomains. Indeed, various stimuli can lead to internalization of caveolae, a specialized form of lipid rafts. Thus, simian virus 40 stimulates its internalization in caveolae and transport via caveosomes (Pelkmans et al., 2001). Similarly, the albumin-docking protein pg60 activates its transendothelial transport by interaction with caveolin-1 and subsequent activation of Src kinase signaling (Minshall et al., 2000). Recently, it has been reported that tetanus toxin can activate, through the TTC fragment, intracellular pathways involving Trk receptors, extracellular signal-regulated kinases (ERK) and protein kinase C isoforms (Gil et al., 2001; Gil et al., 2000; Gil et al., 2003). In this way, tetanus toxin could therefore autoactivate its neuronal endocytosis via an uncoated pathway rather than by clathrin-dependent pathway to avoid the lysosomal degradation.

Finally, we have demonstrated that GFP-TTC trafficking is regulated by neurotrophic factors. By visualization of GFP-TTC trafficking, our data show that BDNF can stimulate both clathrin-coated and uncoated endocytic pathways, presumably via TrkB activation. Since tetanus toxin, as other pathogens or toxins, uses constitutive mechanisms for its internalization and traffic in cells, we have been able to visualize with GFP-TTC, a physiological response to neurotrophic factors.

This aspect of the invention is further discussed in the following examples.

EXAMPLE 9

GFP-TTC Localization at the NMJ

Figure 6B:
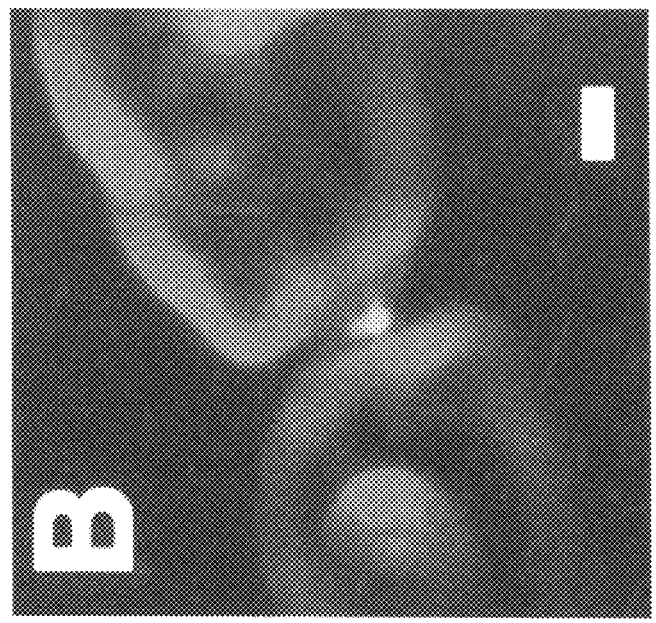
FIG. 6 shows the confocal immunofluorescence analysis of GFP-TTC membrane traffic at mature mouse LAL NMJs.
Figure 6A:
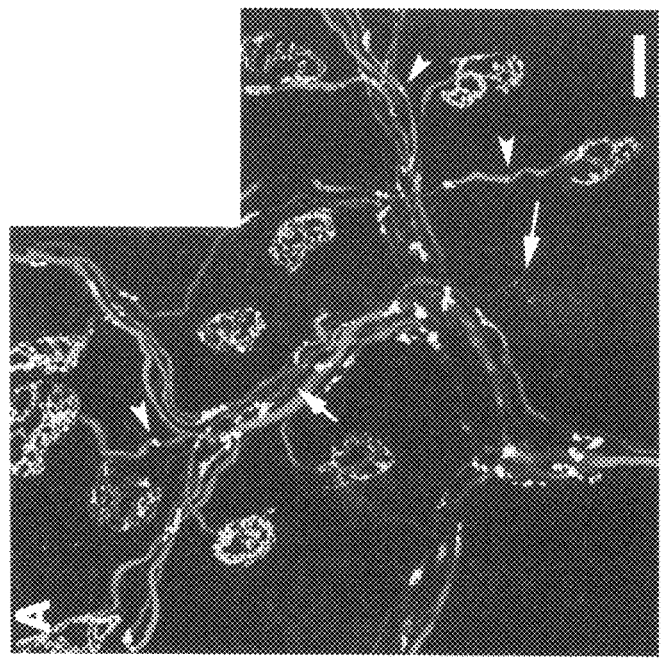
Figure 6C:
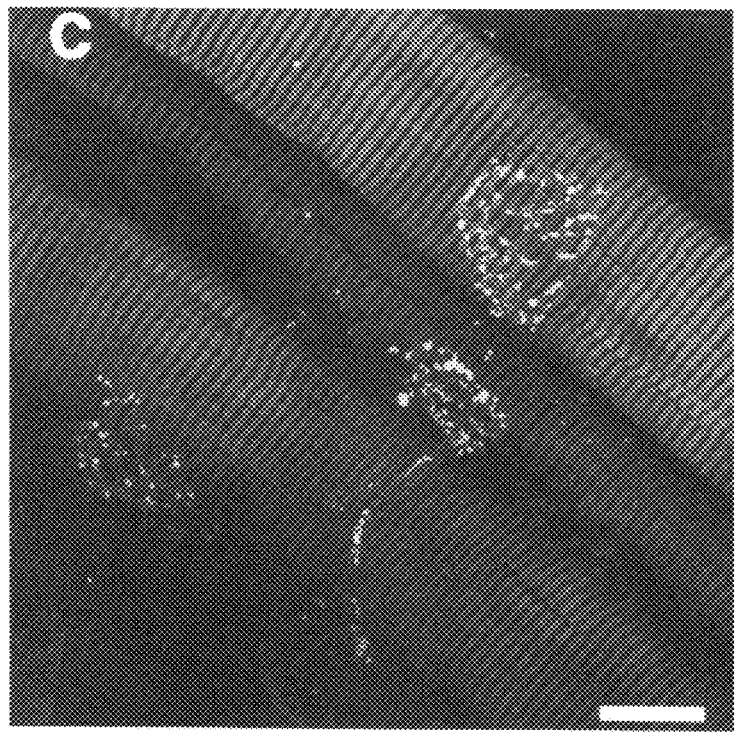
Figure 6C:
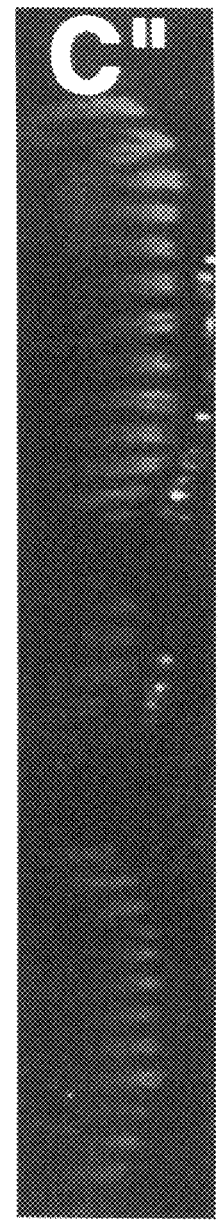
Figure 6C:
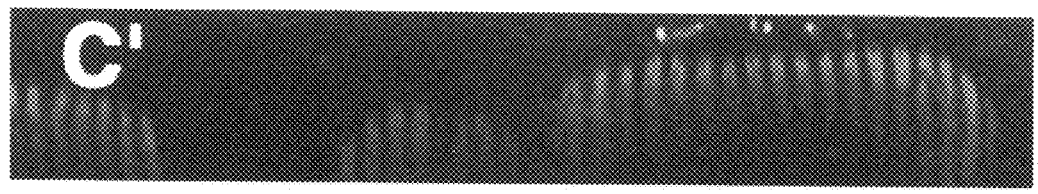
Figure 6D:
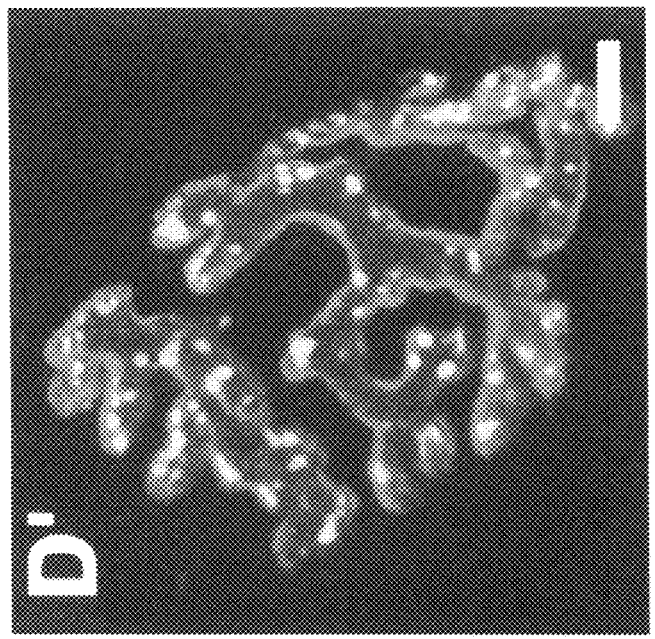
Figure 6D:
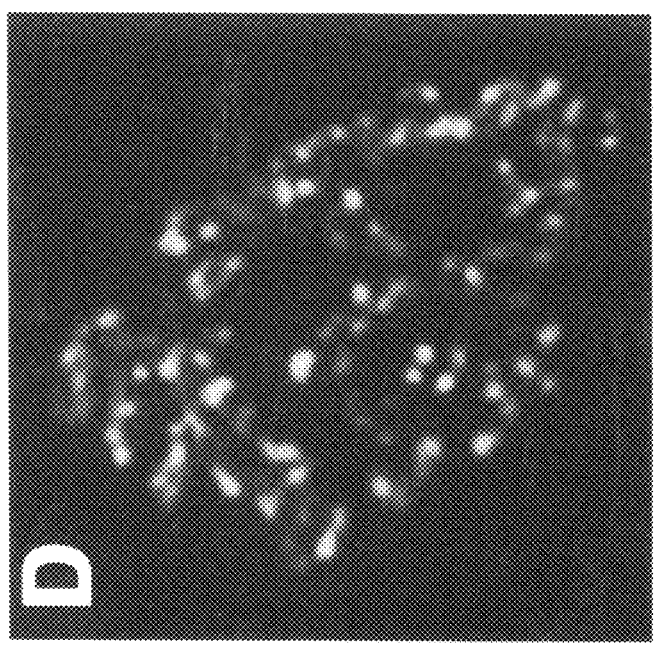
Figure 6E:
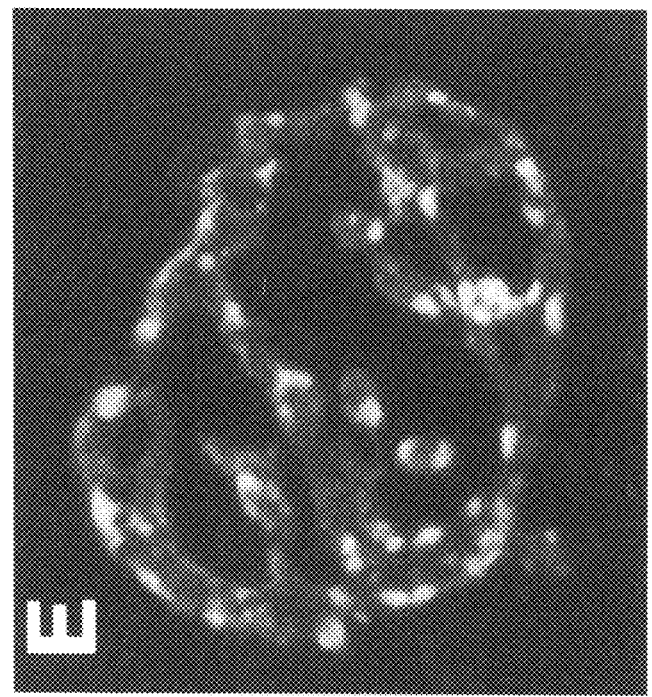
Figure 6E:
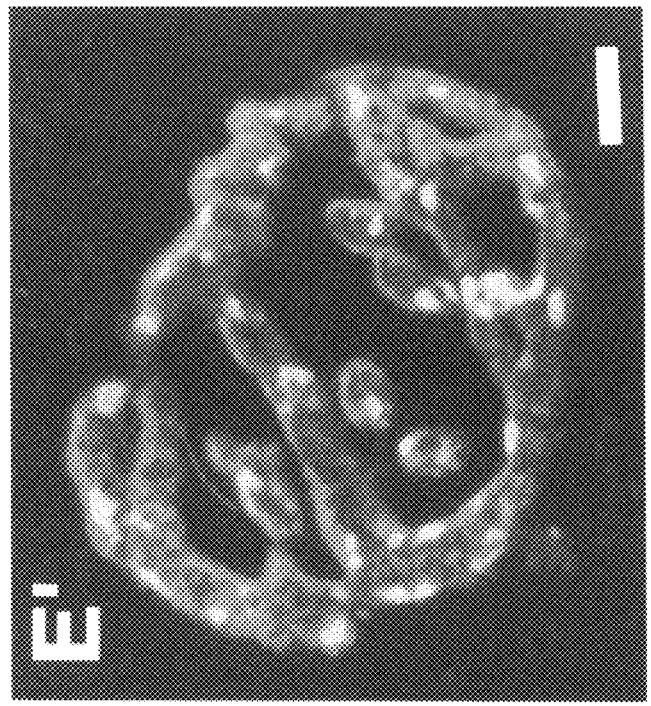
Figure 6F:
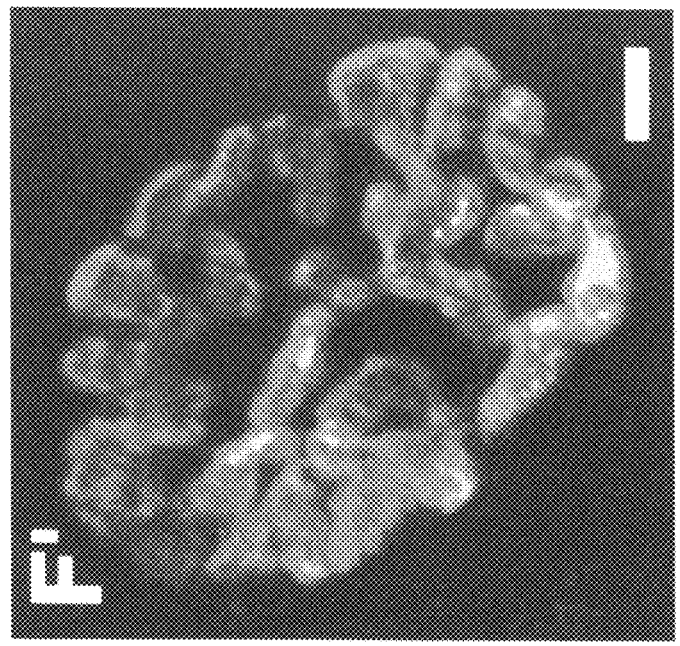
Figure 6F:
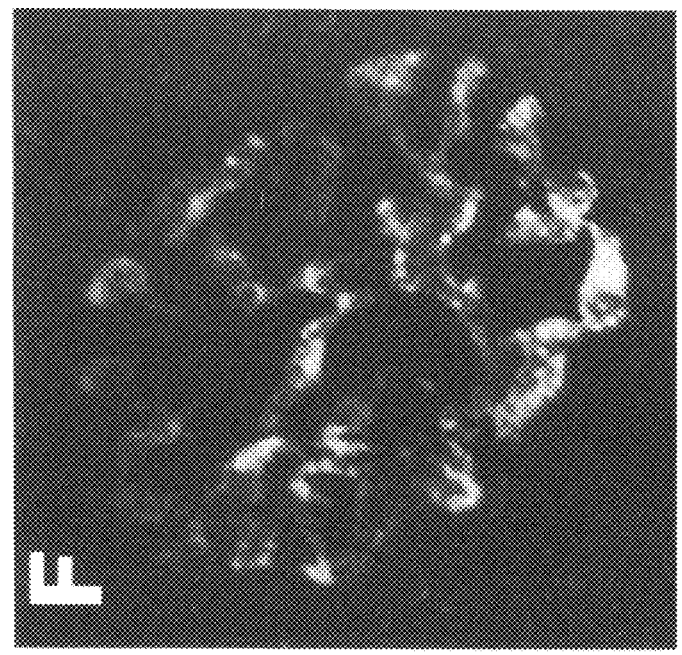
Figures 3, 7A:
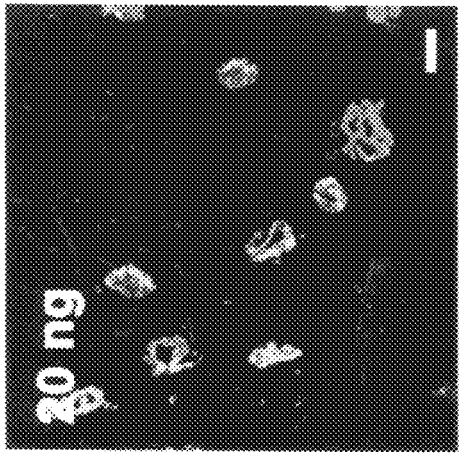
Figures 6, 7A:
Figures 2, 7A:
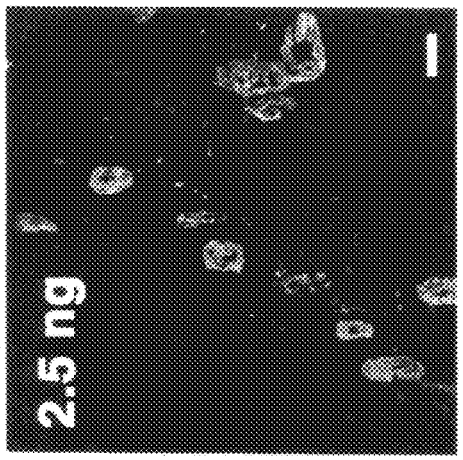
Figures 5, 7A:
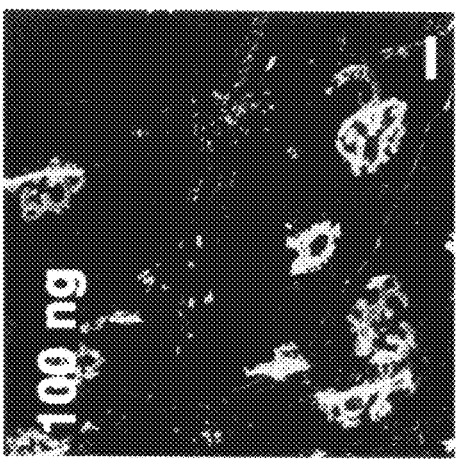
Figures 1, 7A:
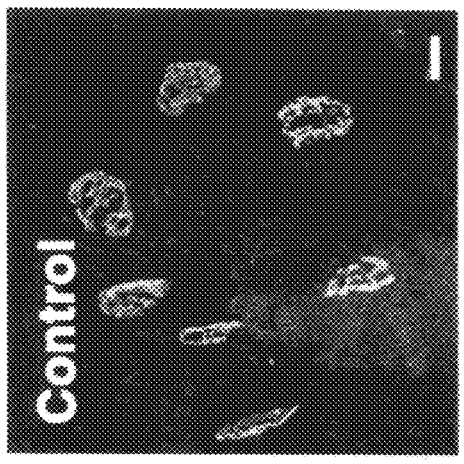
FIG. 1 shows the DNA sequence [SEQ ID NO:1] and amino acid sequence [SEQ ID NO:2] of the TTC fragment cloned in pBS:TTC.
Figures 4, 7A:
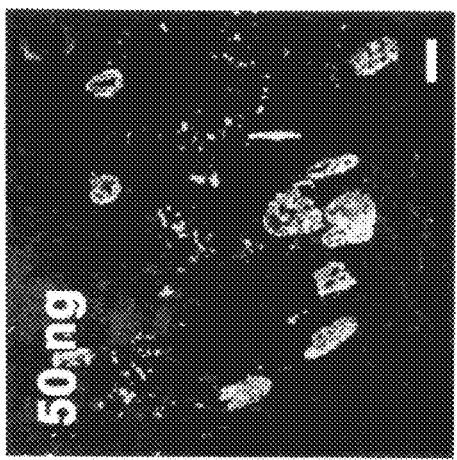
Figure 7B:
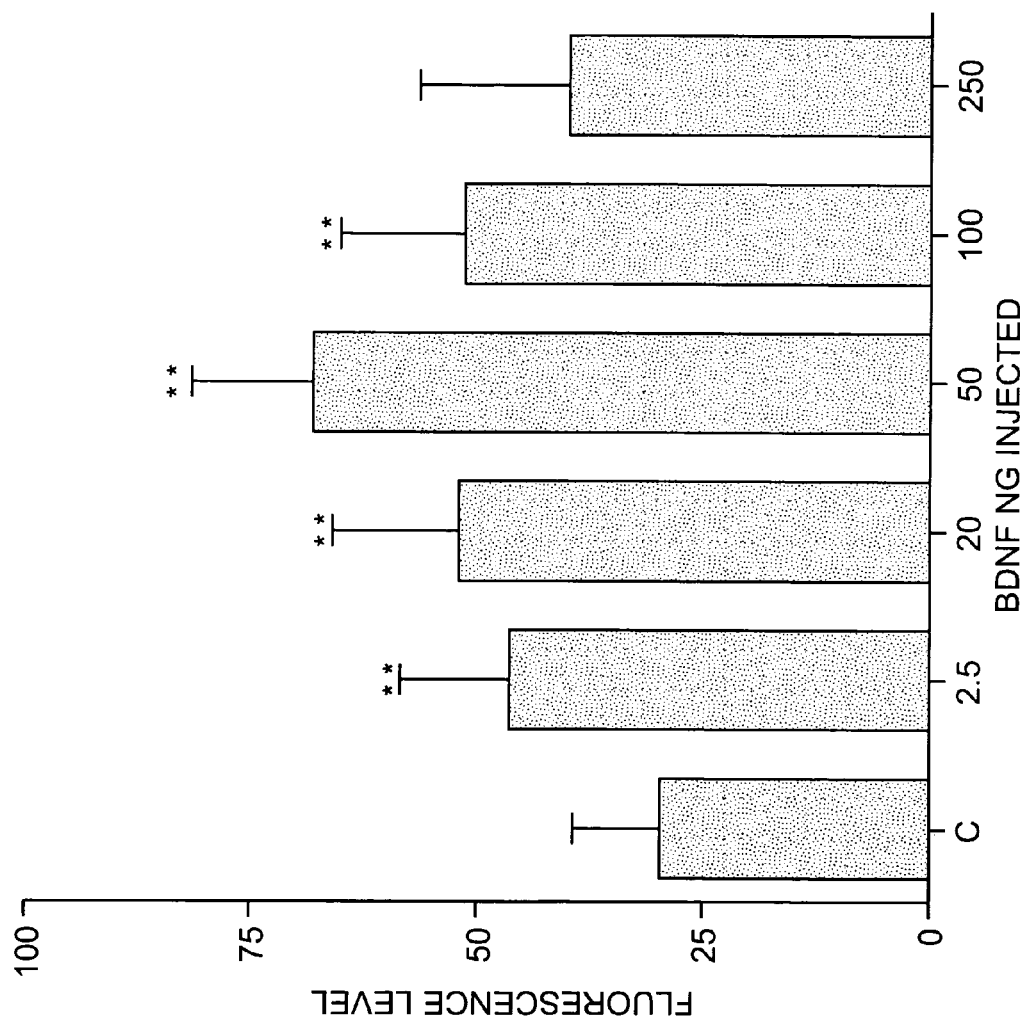
Figure 8A:
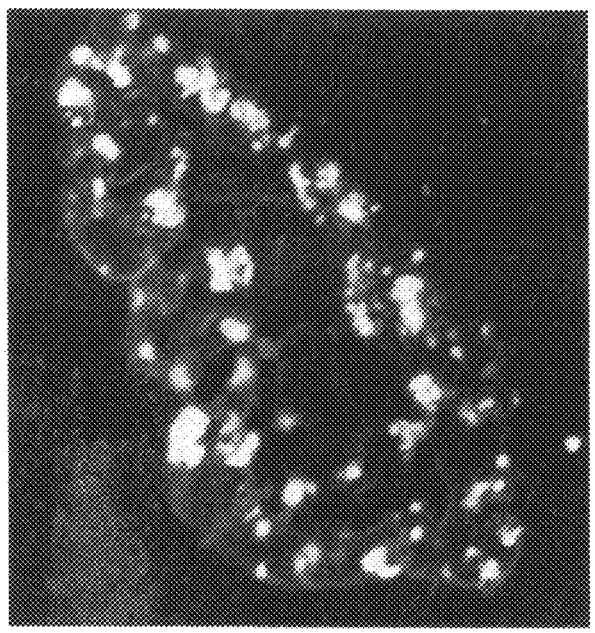
Figure 8B:
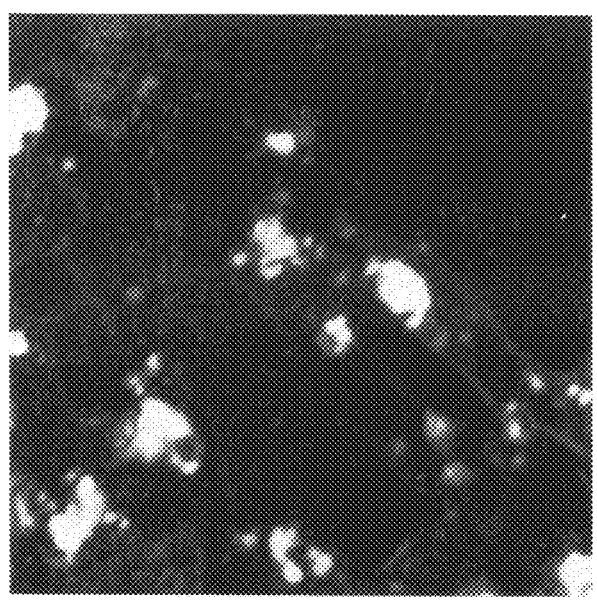
Figure 8C:
Figure 8D:
Figure 8E:
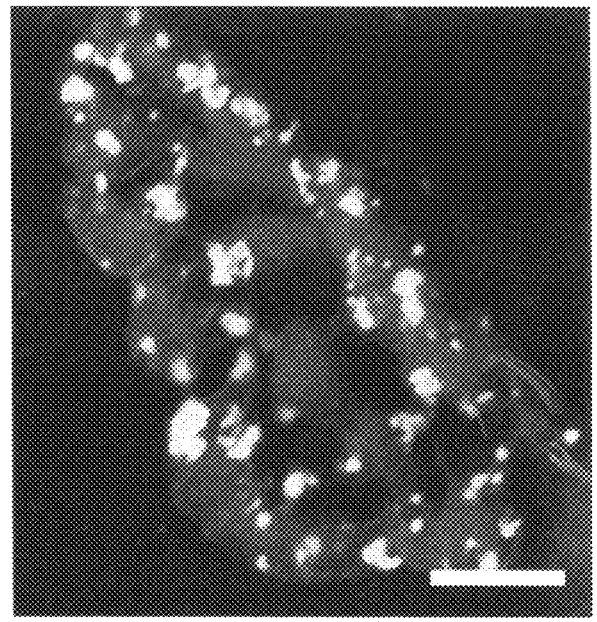
Figure 8F:
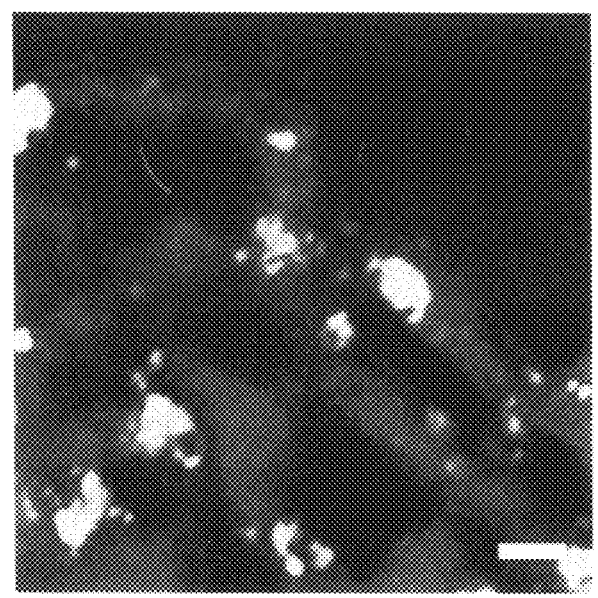

To determine the characteristics of the GFP-TTC distribution at the NMJ, a single injection of the GFP-TTC fusion protein was performed in the immediate vicinity of the Levator auris longus (LAL) muscle and at various times after the injection, the LAL was removed and examined as a whole mount. As LAL is a thin and flat muscle consisting of only a few layers of fibers, the entirety of the neuromuscular preparation with associated nerves could be examined by confocal analysis (FIG. 6A). As shown in FIG. 6, GFP-TTC rapidly concentrates at the NMJ, as identified by the staining of muscle nicotinic acetylcholine receptors with TRITC-conjugated α-bungarotoxine (α-BTX). A patchy clustering of GFP-TTC was observed after approximately 5 min following the deposit of the fusion protein onto the surface of the LAL muscle (FIGS. 6D and D'). After 30 min, a more diffuse staining was observed that was distributed over the entire surface of the NMJ (FIGS. 6E and E'), and which persisted for about 2 h (FIGS. 6F and F'). Immunostaining experiments, performed with an antibody that recognizes troponin T confirmed that GFP-TTC is concentrated mainly in presynaptic motor nerve terminals of the NMJ (FIGS. 6C and C'). We could also detect a strong GFP-TTC labeling at the nodes of Ranvier of intramuscular myelinated axons and in sensory nerve fibers (FIGS. 6A and B; arrows and arrowheads respectively). It is likely that most of the GFP-TTC probe was internalized within 24 h, since only a few fluorescent patches persisted at the NMJ 24 h after its injection (FIGS. 6G and G').

EXAMPLE 10

Influence of BDNF on GFP-TTC Trafficking in Motor Nerve Terminals

To assess whether exogenously applied neurotrophins affected GFP-TTC recruitment in motor nerve terminals, increasing concentrations of BDNF (2.5-250 ng) were co-injected with GFP-TTC in the vicinity of LAL muscles, while control mice were injected with GFP-TTC alone. Mice were sacrificied and LAL muscles harvested 30 min after injection. GFP fluorescence was quantified by confocal microscopy analysis at NMJs, after identification by TRITC-A-BTX labeling. BDNF injection produced a statistically significant concentration-dependent enhancement of GFP-TTC fluorescence at the NMJ, with the highest effect obtained with 50 ng BDNF (FIG. 7B and Table 2) while higher doses (100 and 250 ng) resulted in weaker elevations in the level of GFP-TTC concentration at the NMJ (1.72±0.12 and 1.15±0.22 fold respectively). The higher GFP-TTC axonal labeling observed at these higher doses (FIG. 7A, arrows), probably correlates to an enhanced internalization of the probe.

In TrkB mutant mice, a physiological phenotype in the facial nerve nucleus, which innervates LAL muscle has been reported (Klein et al., 1993; Silas-Santiago et al., 1997). To exclude the possibility that the BDNF effect observed could be LAL specific, a different muscle, the gastrocnemius, was also analyzed. Thirty minutes after injecting GFP-TTC (+BDNF 50 ng) in gastrocnemius, muscles were fixed, removed and serially sectioned. For each muscle, different serial sections were quantified for GFP-TTC fluorescence at the motor nerve terminals as described in material and methods. We found that the BDNF-dependent increase of GFP-TTC concentration at the NMJ, closely resembled that observed in LAL (1.51±0.12 fold increase vs 2.12±0.19 respectively).

EXAMPLE 11

Influence of Other Neurotrophic Factors on GFP-TTC Localization at Motor Nerve Terminals We also examined the effect of five additional trophic factors on GFP-TTC localization at the NMJ, including the neurotrophins NT-3; NT-4 and NGF as well as the neurocytokine CNTF (Ciliary Neurotrophic Factor), a member of the LIF cytokine family, and GDNF (Glial Derived Neurotrophic Factor), a member of the TGF-β superfamily (Table 2). Many BDNF actions in neurons are mediated via the high affinity receptor tyrosine kinase TrkB, which is also the receptor for NT-4. Like BDNF, NT-4 also induced GFP-TTC localization at the NMJ (a 1.54±0.23 fold increase). A level of induction similar to NT-4 was also observed for GDNF (Table 2). On the other hand, even at high concentrations, neither NGF, NT-3, nor CNTF exhibited a significant effect on GFP-TTC localization.

TABLE 2

Effect of various neurotrophic factors on nerve terminal's GFP-fluorescence level 30 min after in vivo GFP-TTC injection.

|  | Receptor | Relative increase in fluorescence level |
|---|---|---|
| BDNF | TrkB | 2.12 ± 0.19** |
| NT-4 | TrkB | 1.49 ± 0.23** |
| NT-3 | TrkC | 0.94 ± 0.05 |
| NGF | TrkA | 1.06 ± 0.06 |
| CNTF | CNTFRα | 0.95 ± 0.05 |
| GDNF | GFRα/cRET | 1.51 ± 0.02* |

GFP-TTC was co-injected with increasing concentrations of neurotrophic factors and GFP fluorescence quantified 30 min after as previously described. Mean of relative increase of GFP fluorescence of 2 or 3 independent experiments are indicated. Maximum fold induction was obtained for 50 ng of neurotrophic factor injected except for NT-3 (2.5 ng).
**$P < 0.005$;
*$P < 0.05$ t-test vs control.

EXAMPLE 12

Comparison of Trk Receptors Distribution and GFP-TTC Localization at Motor Nerve Endings Detection of either TrkB mRNA or protein in adult skeletal muscle and motoneurons has been reported in several studies (Funakoshi et al., 1993; Gonzalez et al., 1999; Griesbeck et al., 1995; Yan et al., 1997). Since our results indicated that the BDNF effect on GFP-TTC localization is dependent on TrkB receptor activation, it was of interest to determine whether GFP-TTC colocalized with TrkB at the NMJ of LAL muscles. Consistent with previous studies (Gonzalez et al., 1999; Sakuma et al., 2001), TrkB immunostaining was confined to the NMJ (FIG. 8). In the presynaptic side, TrkB staining was adjacent to, but not colocalized to the clusters of GFP-TTC labeling. Similar results were also obtained with an antibody that recognizes the activated Trk receptors (p-Trk, data not shown). This observation suggests that the mechanism whereby BDNF has an influence on the concentration of GFP-TTC at the nerve terminals, does not involve a direct interaction between TrkB and GFP-TTC or its receptors.

EXAMPLE 13

Mechanisms Involved in BDNF Effect on GFP-TTC Concentration at the NMJ

Possible explanations for the BDNF-induced enrichment of GFP-TTC at the NMJ could involve an elevated rate of localization of the probe at the NMJ, and/or an increased neuronal endocytosis of the probe. Confocal analysis performed 5, 15, 30, 60 and 120 min after GFP-TTC injection (+BDNF 50 ng) showed maximal labeling intensity at 30 min with BDNF injection, whereas in controls, the maximal staining occurred at 1 h and reached a level lower than that obtained with BDNF co-injection. After the first hour, similar levels of GFP-TTC were recorded at the NMJ in both conditions (FIG. 9A). These results are in accordance with previous results in Xenopus nerve-muscle co-culture indicating a time-limiting effect of BDNF (Lohof et al., 1993).

In vitro, tetanus neurotoxin internalization in neurons appears to involve both coated and uncoated-vesicular pathways (Herreros et al., 2001; Matteoli et al., 1996). Experiments performed either in vitro on excised LAL muscles with the endocytic fluid marker RH414 (data not shown), or immunostained against the SV2 synaptic vesicle proteins (FIG. 9B) and synaptophysin (data not shown) showed some overlapping with GFP-TTC labeling, indicating that the endocytosis of GFP-TTC was in part via recycling of neuronal synaptic vesicles. To differentiate between clathrin-dependent and clathrin-independent endocytic pathways, we used treatment with *botulinum* neurotoxin serotype A (BoTx/A), which blocks neurotransmitter release and endocytosis in motor nerve terminals (de Paiva et al., 1999). When BoTx/A was applied 48 hours before GFP-TTC injection, the probe level at the NMJ was markedly decreased by 50% (FIG. 9C), indicating that both clathrin-dependent and independent pathways are used to a comparable degree.

Enhanced synaptic transmission produced by application of exogenous BDNF; NT-3 or NT-4 involves a potentiation of neurotransmitter release (Lohof et al., 1993; Stoop and Poo, 1996; Wang and Poo, 1997). The increasing amount of GFP-TTC at the NMJ induced by BDNF injection could therefore be due in part to an elevated recycling of synaptic vesicles. To explore this hypothesis, increased exocytosis and endocytosis of synaptic vesicles were induced by GFP-TTC injection in a high-potassium medium. Five minutes after injection, exposure to high $K^+$ medium or BDNF induced a similar increase of GFP-TTC level at the NMJ. However, after 30 min, the effect of high $K^+$ was no longer detectable, whereas maximal induction was reached with BNDF at this time (FIG. 9D). Finally, even after neurotransmitter release and synaptic vesicle recycling were blocked by BoTx/A, an increased GFP-TTC signal was induced by BDNF treatment (FIG. 9C) with an amplitude comparable to that recorded in the non-paralyzed control NMJ (2.05 fold increase vs 2.12 respectively). Taken together, these results indicate that BDNF enhances an alternative endocytic pathway that appears to involve uncoated vesicles.

EXAMPLE 14

Evidence for Association of GFP-TTC in Detergent-insoluble Membrane at the Neuromuscular Junction Binding of TTC to plasma membranes involves association to polysialogangliosides GD1b and GT1b, as well as a N-glycosylated 15 kDa protein. These three components partition preferentially in membrane microdomains called rafts. In vitro, TTC has been shown to associate with such microdomains in NGF-differentiated PC12 cells and in cultured spinal cord neurons (Herreros et al., 2001; Vyas, 2001). To test in vivo whether GFP-TTC associated to lipid rafts, gastrocnemius muscles were submitted to detergent extraction to isolate lipid microdomains after GFP-TTC intramuscular injection. Twelve fractions from the discontinuous sucrose gradient were collected and analyzed for distribution of GFP-TTC.

Figure 10A:
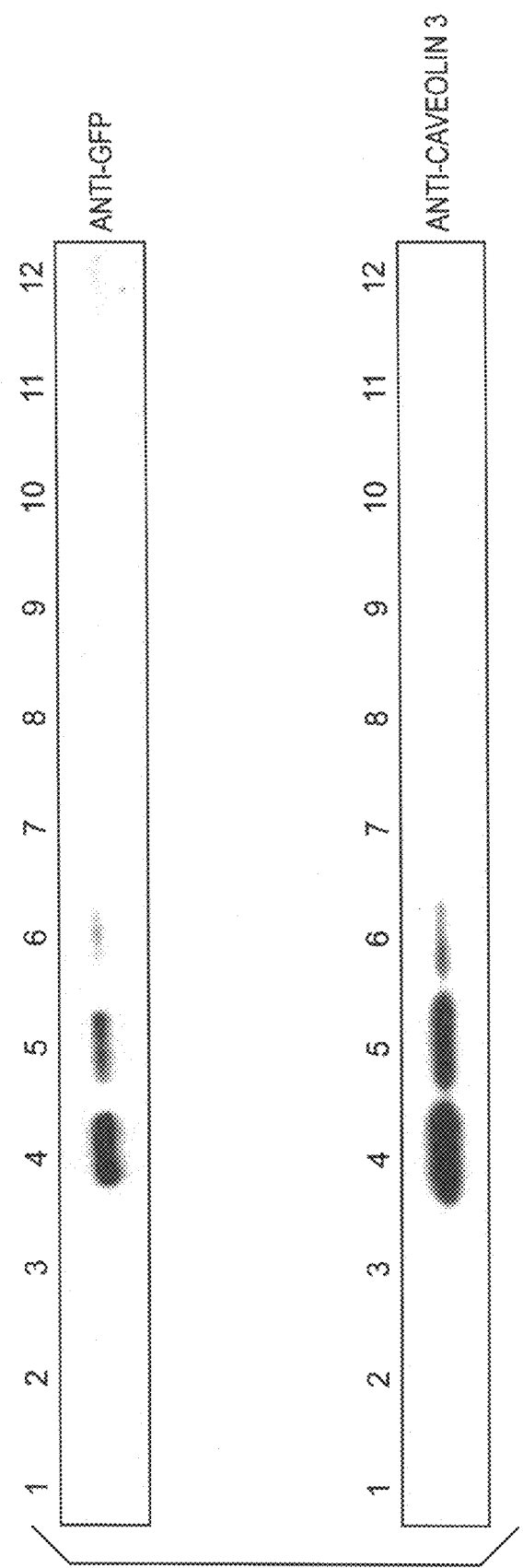

Neurons do not contain caveolin or morphologically distinct caveolae (Anderson, 1998), but significant fractions of cholesterol and glycosphingolipids are found in detergent-insoluble complexes, which are indistinguishable using the criteria of detergent insolubility from those associated with caveolae (Schnitzer et al., 1995). Thus, caveolin 3, a specific muscular caveolar marker (Tang et al., 1996), was used to identify the detergent-resistant fractions. Immunoblot analysis revealed that GFP-TTC co-migrated with raft microdomains, which contain caveolin 3 (FIG. 10A).

Figure 10B:
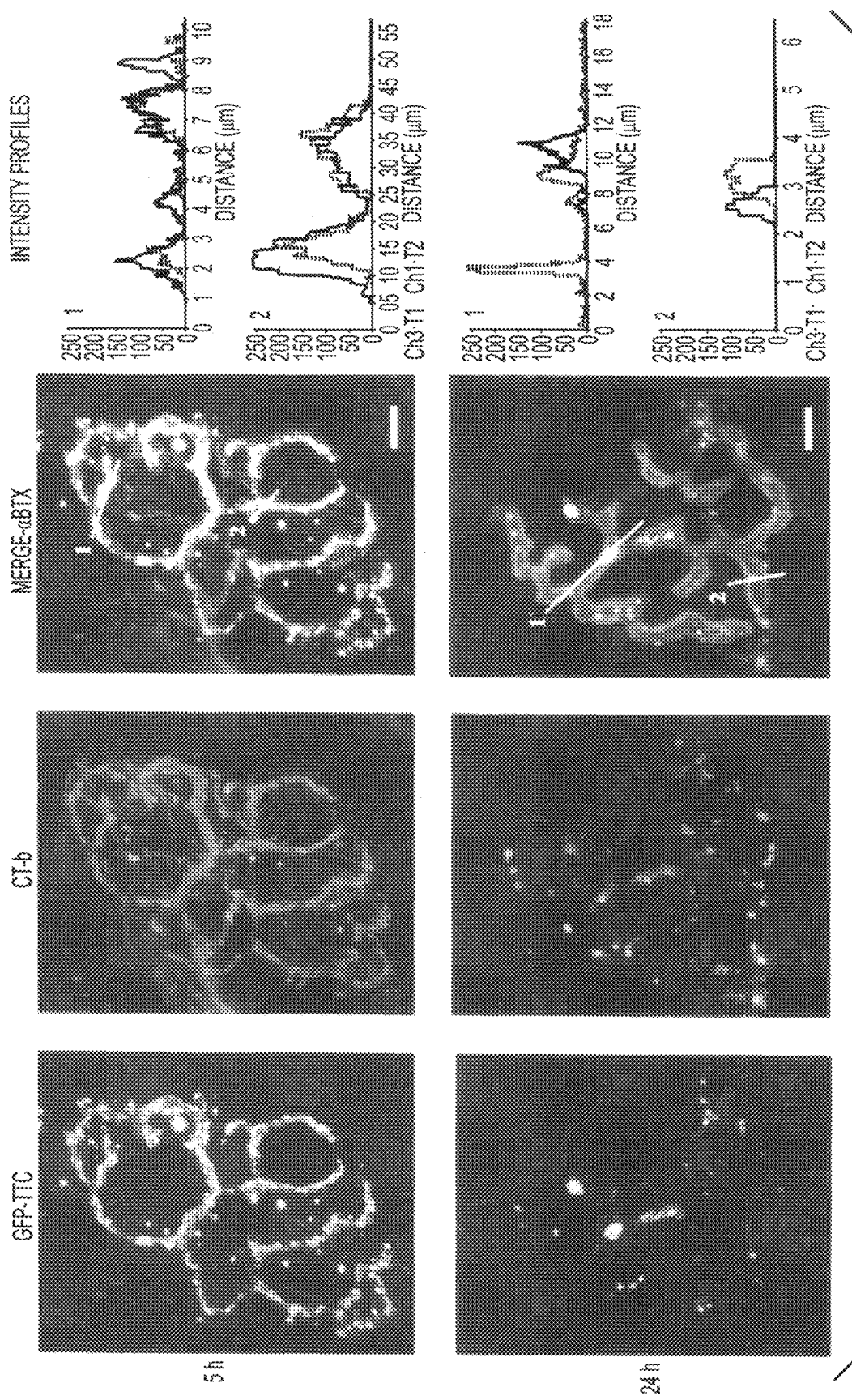
Figure 11B:
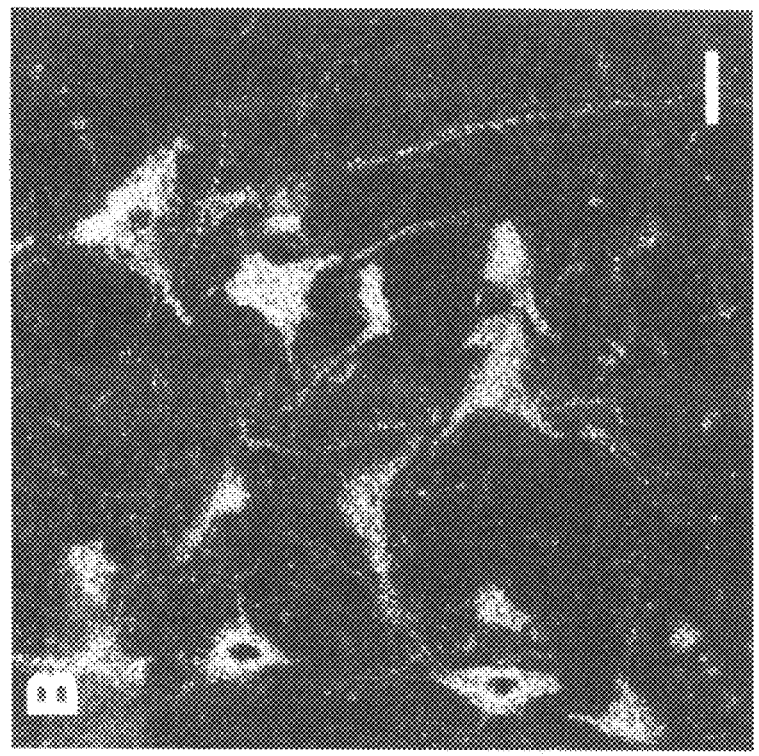
Figure 11A:
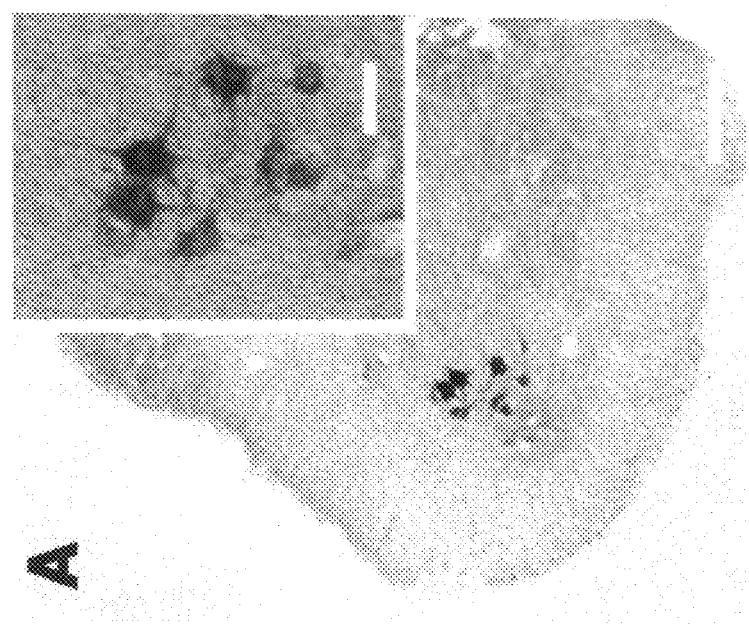
Figure 11C:
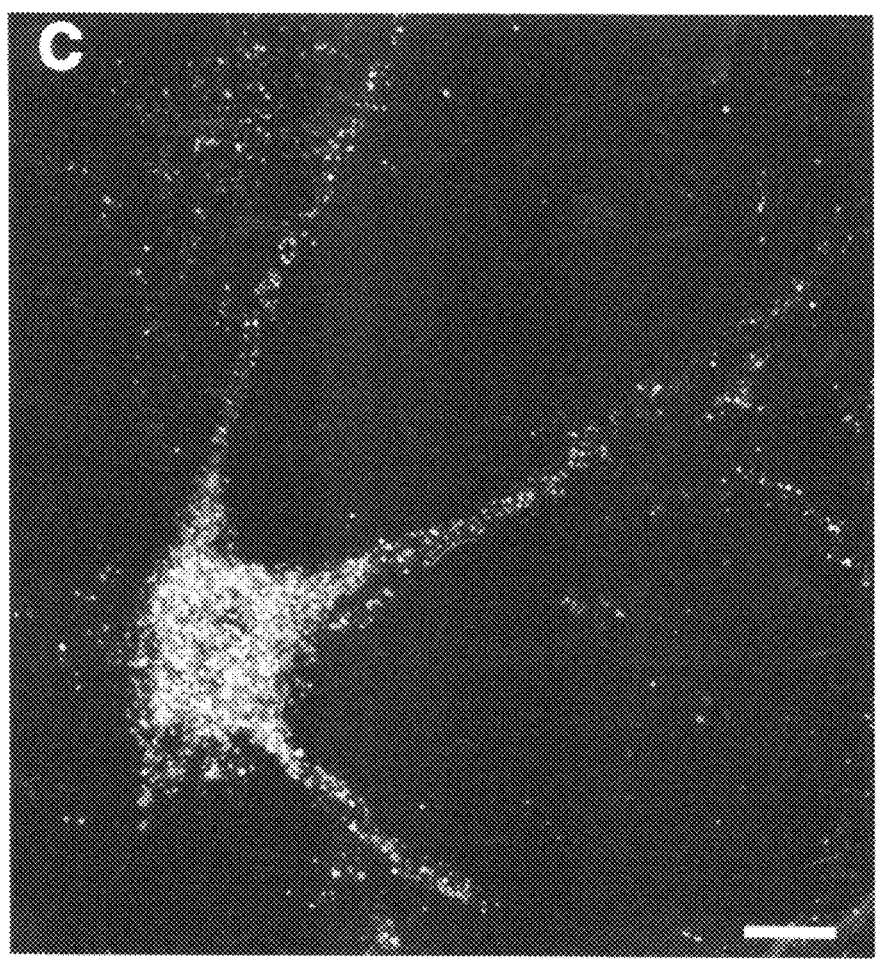
Figure 11E:
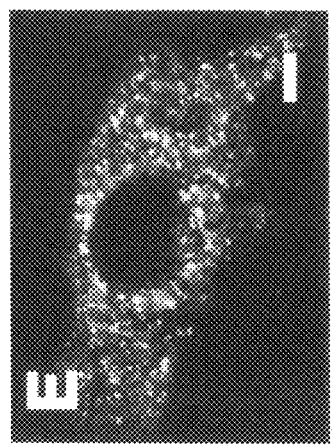
Figure 11D:
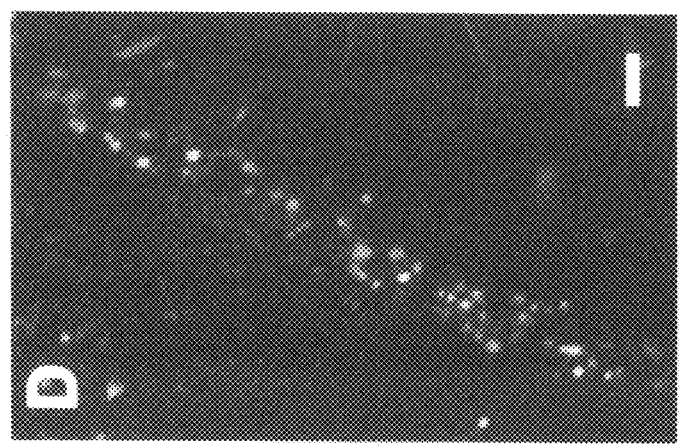

To investigate whether the GFP-TTC patches observed in vivo in motor nerve terminals correspond to lipid microdomains, we performed co-staining with Alexa 594-conjugated cholera toxin-B fragment (CT-b). CT-b specifically binds to ganglioside GM1, which is enriched in cholesterol-rich membrane microdomains, and is commonly used as a marker for membrane rafts and caveolae (Orlandi and Fishman, 1998; Schnitzer et al., 1995; Wolf et al., 1998). GFP-TTC and Alexa 594-conjugated CT-b fragment were co-injected into the gastrocnemius and confocal analysis was performed 1; 3; 5; 9 and 24 h later, with the NMJ being identified by AlexaFluor 647-conjugated α-BTX (FIG. 10B). Although the GFP-TTC labeling of motor nerve terminals was easily visualized in less than the 5 min necessary to process the tissue (FIGS. 6D and D'), CT-b was detectable at the NMJ only several hours after injection (3-5 h). Thus, the dynamics of trafficking of CT-b and TTC receptors to active synapse are clearly different. However, after 5 h, the distribution obtained for CT-b was similar to GFP-TTC staining, as characterized by diffuse staining and patches having an extensive overlap of the staining patterns obtained with GFP-TTC, indicating a localization of the TTC probe in lipid microdomains in motor nerve endings (FIG. 10B). Twenty four hours after gastrocnemius injection, both toxins had been internalized since only few patches, most of them positive for both toxins, persisted at the NMJ (FIGS. 10B and C). At this time, GFP-TTC and CT-b staining were detected in the same motoneuron cell bodies in the ventral horn of the spinal cord, but in different vesicular compartments (FIG. 11). Taken together, these results indicate that GFP-TTC used different lipid microdomains for neuronal binding and/or internalization pathways than CT-b.

MATERIALS AND METHODS

Antibodies and Reagents.

Rabbit anti-GFP polyclonal antibodies was obtained from Invitrogen (1:5000 dilution). Mouse monoclonal antibody against caveolin 3 was from Transduction Laboratories (1:500). The monoclonal anti-neurofilament 200 (clone NE14) and the rabbit polyclonal antitroponin T were obtained from Sigma. AlexaFluor 594-conjugated Cholera toxin subunit B (CT-b); AlexaFluor 488-conjugated goat-antirabbit IgG, AlexaFluor 647-conjugated α-bungarotoxin (α-BTX) and RH414 were obtained from Molecular Probes. Cy3-conjugated goat anti-rabbit IgG and Cy3-conjugated rat anti-mouse IgG were from Jackson Laboratories. TRITC-conjugated α-bungarotoxin was obtained from Calbiochem. The rabbit anti-TrkB (794) and the anti-p-Trk polyclonal antibody were obtained from SantaCruz. The monoclonal antibody against synaptic vesicle protein SV2, developed by K. Buckley, was obtained from the Developmental Studies Hybridoma Bank developed under the auspices of the NICHD and maintained by The University of Iowa, Department of Biological Sciences, Iowa City. Monoclonal antibody against synaptic vesicle synaptophysin protein was obtained from Chemicon. The goat anti-rabbit and anti-mouse IgG antibodies conjugated to horseradish peroxydase were obtained from Pierce as well as the SuperSignal detection reagent. Recombinant neurotrophic factors rat CNTF; human NT3; human NT-4, human BDNF, human GDNF and purified mouse NGF 7S were purchased from Alomone labs. Neurotrophic factors were prepared as stock solutions (10 μg/ml) and kept in aliquots at −80° C.

In Vivo Intramuscular Injection

Experiments were performed in accordance with French and European Community guidelines for laboratory animal handling. Six-week-old Swiss female mice were obtained from Charles River Breeding Laboratories. Intramuscular injections of β-gal-TTC, GFP-TTC fusion proteins, produced as previously described (Coen et al., 1997), or AlexaFluor 594-conjugated CT-b were intramuscular injected into the gastrocnemius muscle or subcutaneously in the immediate vicinity of the Levator auris longus (LAL) muscle on anesthetized mice. For fluorescence quantification, 25 μg of GFP-TTC fusion protein were injected in PBS in 50 μl final volume. For immunodetection or biochemical extraction, 50 μg of GFP-TTC probe were used. When co-injections with neurotrophic factors were performed, the volume injected was kept constant (50 μl). For injection in high $K^+$, a physiological solution containing 60 mM KCl was co-injected with the probe.

Botulinum type-A toxin injection.

Clostridium botulinum type-A toxin (BoTx/A) was injected subcutaneously as a single dose of 0.05 ml containing about 0.5 μg of the purified neurotoxin in the vicinity of the LAL muscle of female Swiss mice (body weight 24-27 g). 48 h after BoTx/A treatment, a time sufficient for inducing muscle paralysis in the LAL due to blockade of neurotransmitter release (de Paiva et al., 1999), GFP-TTC (25 μg) was injected associated or not with BDNF (50 ng) in the vicinity of the LAL muscle. Mice were killed by intracardial injection of PFA 4% 30 min after injection and LAL muscle harvested and processed for confocal analysis.

In vitro analysis of GFP-TTC localization and confocal acquisition.

LAL muscles with their associated nerves were isolated from female Swiss-Webster mice (20-25 g), killed by dislocation of the cervical vertebrae. LAL muscles were mounted in Rhodorsil$^R$-lined organ baths (2 ml volume) superfused with a standard oxygenated physiological solution of the following composition (mM): NaCl 154; KCl 5; $CaCl_2$ 2; $MgCl_2$ 1; HEPES buffer 5 (pH=7.4) and glucose 11. Muscles were loaded for 45 min in the dark and at room temperature with both 25 μg GFP-TTC and 30 μM of RH414, dissolved in standard solution or, for synaptic vesicle recycling, in high $K^+$ isotonic solution (with 60 mM KCl replacing 60 mM NaCl). Preparations were washed out of the GFP-TTC and RH414 dye, and rinsed several times with dye-free standard medium before being imaged with a Leica TCS SP2 confocal laser scanning microscope system (Leica Microsystems, Germany) mounted on a Leica DM-RXA2 upright microscope equipped with a ×40 water immersion lens (Leica, NA 0.8). The confocal system was controlled through Leica-supplied software running on a Windows NT workstation.

Preparation of Detergent-Resistant Membrane (DRMs) Fractions and Western Blot.

Preparation of detergent-resistant membrane fractions is one of the most widely used methods for studying lipid rafts. Two hours after GFP-TTC injection (50 μg), mouse gastrocnemius muscle tissue was harvested, minced with scissors and homogenized in 2 ml of MES-buffered saline containing 1% (v/v) Triton X-100. Homogenization was carried out with a Polytron tissue grinder. After centrifugation at low speed for 5 min, supernatant was adjusted to 40% sucrose. A 5-30% linear sucrose gradient was formed above the homogenate and centrifuged at 39,000 rpm for 18 h in a SW41 rotor. Then, 11-12 fractions of 1 ml were collected from the top of the gradient and precipitated with 6.5% trichloroacetic acid in the presence of 0.05% sodium deoxycholate and washed with 80% cold acetone. Samples were analyzed by Western Blot after separating on a 4-15% SDS-PAGE followed by Western Blot. Membranes were probed first with polyclonal anti-GFP and monoclonal anti-caveolin 3 antibodies, and then incubated with goat anti-rabbit IgGs and goat anti-mouse IgGs antibodies conjugated with horseradish peroxydase. The SuperSignal (Pierce) was used to visualize the reaction Quantification of GFP-TTC Fluorescence Intensity at the NMJ.

After intracardiac perfusion and fixation, LAL muscles were harvested, washed in PBS for 20 min, stained with TRITC-conjugated a-bungarotoxin (TRITC-a-BTX) (2 μg/ml) for 45 min at 37° C. in PBS and washed twice in PBS. Images were acquired on an Axiovert 200M laser scanning confocal microscope (LSM-510 Zeiss; version 3.2) through a ×40/1.2 water-immersion objective using LP560 and BP505-550 filters. The pinhole aperture was set to 1 airy unit, and images were digitized at 8-bit resolution into a 512×512 pixel array. To be able to compare the intensity of GFP staining between different experiments, laser illumination, photomultiplier gain in regard of linear response, and other acquisition variables were standardized. To quantify GFP-TTC localization at the NMJ, series of "look-through" projection (of MIP: Maximum Intensity Projection) was generated. Images from each NMJ were processed identically: NMJ surface area (in $μm^2$) was determined by TRITC-a-BTX labeling and GFP fluorescence global intensity (sum of each pixel intensity) was then measured only in this predefined area. This value, divided by the NMJ area yielded GFP fluorescence intensity per square micrometer, which thus defined the fluorescence level expressed as arbitrary units. For each condition, ~15 to 20 synapses were quantified and results were expressed as the mean±SD. Statistical significance was defined as $p<0.05$ using a two-tailed t test. Each experiment was repeated at least two or three times.

Analysis of Spinal Cord.

24 hours after β-gal-TTC or GFP-TTC and CT-b injection into the gastrocnemius muscle (50 μg each), mice deeply anesthetized were perfused intracardially with 4% PFA. The spinal cord was harvested and embedded in Tissue Tek embedding media after overnight incubation in 25% sucrose in PBS 0.1 M. Longitudinal cryostat sections (30 μm thickness) were cut and mounted onto coated slides.

X-gal reaction.

X-gal reaction was performed as previously described (Coen et al., 1997).

REFERENCES

The following publications, which have been cited herein, are relied upon and incorporated by reference in their entireties herein.

1. Eisel, U., Jarausch, W., Goretzki, K., Henschen, A., Engels, J., Weller, U., Hudel, M., Habermann, E. & Niemann, H. (1986) *EMBO J.* 5, 2495-2502.
2. Fairweather, N. F. & Lyness, V. A. (1986) *Nucleic Acids Res.* 14, 7809-7812.
3. Montecucco, O. & Schiavo, G. (1995) *Quart. Rev. Biophys.* 28, 423-472.
4. Schwab, M. E. & Thoenen, H. (1976) *Brain Res.* 105, 213-227.
5. Schwab, M. E. & Thoenen, H. (1977) *Brain Res.* 122, 459-474.
6. Price, D. L., Griffin, J. W. & Peck. K. (1977) *Brain Res.* 121, 379-384.
7. Bizzini, B., Stoeckel, K. & Schwab, M. (1977) *J. Neurochem.* 28, 529-542.
8. Evinger, O. & Erichsen, J. T. (1986) *Brain Res.* 380, 383-388.
9. Fishman, P. S. & Carrigan, D. R. (1987) *Brain Res.* 406, 275-279.
10. Manning, K. A., Erichsen, J. T. & Evinger, O. (1990) *Neurosci.* 34, 251-263.
11. Halpern, J. L., Habig, W. H., Neale, E. A. & Stibitz, S. (1990) *Infection and Immunity* 58, 1004-1009.
12. Bizzini, B., Grob, P., Glicksman, M. A. & Akert, K. (1980) *Brain Res.* 193, 221-227.
13. Dobrenis, K., Joseph, A. & Rattazzi, M. G. (1992) *Proc. Natl. Acad. Sci. USA* 89, 2297-2301.
14. Fishman, P. S. & Savitt, J. M. (1989) *Exp. Neurol.* 106, 197-203.
15. Beaude, P., Delacour, A., Bizzini, B., Domuado, D. & Remy, M. H. (1990) *Biochem.* 271, 87-91.
16. Francis, J. W., Hosler, B. H., Brown, R. H., Jr. & Fishman, P. S. (1995) *J. Biol. Chem.* 270, 15434-15442.
17. Fellous. M., Gunther, E., Kemler, R., Weils, J., Berger, R., Guenet, J. L., Jakob, H. & Jacob, F. (1978) *J. Exp. Med.* 148, 58-70.
18. Jakob, H. & Nicolas, J. F. (1987) *Methods Enzymol.* 151, 66-84.
19. Whitehouse, R. L. S., Benichou, J. O. & Ryter, A. (1977) *Biol Cell.* 30, 155-158.
20. Wojcik, B. E., Nothias, F., Lazar, M., Jouin, H., Nicolas, J. F. & Peschanski, M. (1993) *Proc. Natl. Acad. Sci. USA* 90, 1305-1309.
21. Price, D. L., Griffin, J. Young, A. Peck, K. & Stocks, A. (1975) *Science* 188, 945-947.
22. Matteoli, M., Verderio, C., Rossetto, O., Iezzi, N., Ooco. S. Schiavo, G. & Montecucco, G, (1996) *Proc. Natl. Acad. Sci. USA* 93, 13310-13315.
23. Stockel, K., Schwab, M. & Thoenen, H. (1975) *Brain Res.* 99, 1-16.
24. Ugolini, G. (1995a) in *Viral Vectors: Gene Therapy and Neuroscience Applications*, eds. Loewy, A. D. & Kaplitt M. G. (New York: Academic Press), pp. 293-317.
25. Ugolini, G. (1995b) *The Journal of Comparative Neurology* 356, 457-480.
26. Borke, R. C., Nau, M. E. & R. L Ringler, J. (1983) *Brain Research* 269, 47-55.
27. Horst, G. T. T., Copray, J. C. V. M., Iiem, R. S. B. & Willigen, J. D. V. (1991) *Neuroscience* 40, 735-758.
28. O'Reilly, P. M. R. & Fitzgerald, M. J. T. (1990) *J. Anat.* 172, 227-243.
29. Chalfie, M. Tu, Y., Euskirchen, G., Ward, W. W. & Prasher, D. C. (1994) *Science* 263, 802-805.
30. Miesenböck, G. & Rothman, J. E. (1997) *Proc. Nat. Acad. Sci. USA* 94, 3402-3407.
31. Le Mouellic, H., Lallemand, Y. & Brûlet, P. (1990) *Proc. Natl. Acad. Sci. USA* 87, 4712-4716.
32. Le Mouellic, H., Lallemand, Y. & Brûlet, P. (1992) *Cell* 69, 251-264.
33. Mombaerts, P., Wang, F., Dulac, C. Chao, S. K., Nemes, A., Mendelsohn, M., Edmondson, J. & Axel, R. (1996) *Cell* 87, 675-686.
34. Mounfford, P. S. & Smith, A. G. (1995) *Trends Genet.* 11, 179-184.
35. Rosen, D. R. & al (1993) *Nature* 362, 59-62.
36. Lefebvre, S., Büglen, L., Reboullet, S. Clermont, O., Bûrlet, P., Viollet, L, Benichou, B., Cruaud, O., Millasseau, P., Zeviani, M., Paslier, D. L., Frézal, J., Cohen, D., Weissenbach, J., Munnich, A. & Melki, J. (1995) *Cell* 80, 155-165.
37. Roy, N. & al (1995) *Cell* 80, 167-178.
38. Wolfe, J. H., Deshmane, S. L. & Fraser, N. W. (1992) *Nature genetics* 1, 379-384.
39. Sango, K., Yamanaka, S., Hoffmann, A., Okuda, Y., Grinberg, A., Westphal, H., McDonald, M. P., Crawley, J. N., Sandhoff, K., Suzuki, K. & Proia, R. L. (1995) *Nature Genetics* 11, 170-176.
40. Duarte, R. G. (1995) *Neurologia* 1, 56-61.
41. Ghadge, G. D., Roos, R. P., Kang, U. J., Wollmann, R., Fishman, P. S., Kalynych, A M., Barr, E. & Leiden, J. M. (1995) *Gene Therapy* 2, 132-137.

Anderson, R. G. W. 1998. The caveolae membrane system. *Annu. Rev. Biochem.* 67:199-225.

Bothwell, M. 1995. Functionnal interactions of neurotrophins and neurotrophin receptors. *Annu. Rev. Neurosci.* 18:223-225.

Coen, L., R. Osta, M. Maury, and P. Brûlet. 1997. Construction of hybrid proteins that migrate retrogradely and transsynaptically into the central nervous system. *Proc. Natl. Acad. Sci. USA.* 94:9400-9405.

de Paiva, A. M., F. A. Meunier, J. Molgo, R. Aoki, and J. O. Dolly. 1999. Functional repair of motor endplates after botulinum neurotoxin type A poisoning: biphasic switch of synaptic activity between nerve sprouts and their parent terminals. *Proc. Natl. Acad. Sci. USA.* 96:3200-3205.

Du, J., L. Feng, F. Yang, and B. Lu. 2000. Activity and $Ca^{2+}$-dependent modulation of surface expression of brain-derived neurotrophic factor receptors in hippocampal neurons. *J. Cell Biol.* 150:1423-1434.

Funakoshi, H., N. Belluardo, E. Arenas, Y. Yamamoto, A. Casabona, H. Persson, and C. F. Ibanez. 1995. Muscle-derived neurotrophin-4 as an activity-dependent trophic signal for adult motor neurons. *Science.* 268:1495-1499.

Funakoshi, H., J. Frisen, G. Barbany, T. Timmusk, O. Zachrisson, V. M. K. Verge, and H. Persson. 1993. Differential expression of mRNAs for neurotrophins and their receptors after axotomy of the sciatic nerve. *J. Cell Biol.* 123:455465.

Gil, C., I. Chaib, J. Blasi, and J. Aguilera. 2001. Hc fragment of tetanus toxin activates protein kinase C isoforms and phosphoproteins involved in signal transduction. *Biochem. J.* 356:97-103.

Gil, C., I. Chaib, P. Pellicioni, and J. Aguilera. 2000. Activation of signal transduction pathways involving TrkA, PLCγ, PKC isoforms and ERK-1/2 by tetanus toxin. *FEBS.* 481:177-182.

Gil, C., I. Chaib-Oukadour, and J. Aguilera. 2003. C-terminal fragment of tetanus toxin heavy chain activates Akt and MEK/ERK signaling pathways in a Trk receptor-dependent manner in cultured cortical neurons. Biochem. J. 373:613-620.

Gonzalez, M., F. P. Ruggiero, Q. Chang, Y.-J. Shi, M. M. Rich, S. Kraner, and R. J. Balice-Gordon. 1999. Disruption of TrkB-mediated signaling induces disassembly of postsynaptic receptor clusters at neuromuscular junction. *Neuron.* 24:567-583.

Griesbeck, O., A. S. Parsadenian, M. Sendtner, and H. Thoenen. 1995. Expression of neurotrophins in skeletal muscle: quantitative comparison and significance for motoneuron survival and maintenance of function. *J. Neurosci. Res.* 42:21-33.

Harder, T., P. Scheiffele, P. Verkade, and K. Simons. 1998. Lipid domain structure of the plasma membrane revealed by patching of membrane components. *J. Cell Biol.* 141:929-942.

Herreros, J., T. Ng, and G. Schiavo. 2001. Lipid rafts act as specialized domains for tetanus toxin binding and internalization into neurons. *Mol. Biol. Cell.* 12:2947-2960.

Higuchi, H., T. Yamashita, H. Yoshikawa, and M. Tohyama. 2003. PKA phosphorylates the p75 receptor and regulates its localization to lipid rafts. *Embo J.* 22:1790-1800.

Huang, E. J., and L. F. Reichardt. 2003. Trk receptors: roles in neuronal signal transduction. *Annu. Rev. Biochem.* 72:609-642.

Klein, R., R. J. Smeyne, W. Wurst, L. K. Long, A. B. A, A. L. Joyner, and M. Barbacid. 1993. Targeted disruption of the trkB neurotrophin receptor gene results in nervous system lessions and neonatal death. *Cell.* 75:113-122.

Lalli, G., and G. Schiavo. 2002. Analysis of retrograde transport in motor neurons reveals common endocytic carriers for tetanus toxin ans neurotrophin receptor p75$^{NTR}$. *J. Cell Biol.* 156:233-239.

Lang, T., D. Bruns, D. Wenzel, D. Riedel, P. Holroyd, C. Thiele, and R. Jahn. 2001. SNAREs are concentrated in cholesterol-dependent clusters that define docking and fusion sites for exocytosis. *Embo J.* 20:2202-2213.

Lohof, A. M., N. Y. Ip, and M. M. Poo. 1993. Potentiation of developing neuromuscular synapses by the neurotrophins NT-3 and BDNF. *Nature.* 363:350-353.

Madore, N., K. L. Smith, C. H. Graham, A. Jen, K. Brady, S. Hall, and R. Morris. 1999. Functionally different GPI proteins are organized in different domains on the neuronal surface. *Embo J.* 18:6917-6926.

Maskos, U., K. Kissa, C. Saint Cloment, and P. Brûlet. 2002. Retrograde trans-synaptic transfer of green fluorescent protein allows the genetic mapping of neuronal circuits in transgenic mice. *Proc. Natl. Acad. Sci. USA.* 95:10120-10125.

Matteoli, M., C. Verderio, O. Rossetto, N. Iezzi, S. Coco, G. Schiavo, and C. Montecucco. 1996. Synaptic vesicle endocytosis mediates the entry of tetanus neurotoxin into hippocampal neurons. *Proc. Natl. Acad. Sci. USA.* 93:13310-13315.

McAllister, A. K., L. C. Katz, and D. C. Lo. 1999. Neurotrophins and synaptic plasticity. *Annu. Rev. Neurosci.* 22:295-318.

Meyer-Franke, A., G. A. Wilkinson, A. Kruttgen, M. Hu, E. Munro, M. G. J. Hanson, L. F. Reichardt, and B. A. Barres. 1998. Depolarization and cAMP elevation rapidly recruit TrkB to the plasma membrane of CNS neurons. *Neuron.* 21:681-693.

Miana-Mena, F. J., S. Roux, J.-C. Benichou, R. Osta, and P. Brûlet. 2002. Neuronal activity-dependent membrane traffic at the neuromuscular junction. *Proc. Natl. Acad. Sci. USA.* 99:3234-3239.

Minshall, R. D., C. Tiruppathi, S. M. Vogel, W. D. Niles, A. Gilchrist, H. E. Hamm, and A. B. Malik. 2000. Endothelial cell-surface gp60 activates vesicle formation, and trafficking via Gi-coupled Src kinase signaling pathway. *J. Cell Biol.* 150:1057-1069.

Mundy, D. I., T. Machleidt, Y. S. Ying, R. G. W. Anderson, and G. S. Bloom. 2002. Dual control of caveolar membrane traffic by microtubules and the actin cytoskeleton. *J. Cell Science.* 115:4327-4339.

Orlandi, P. A., and P. H. Fishman. 1998. Filipin-dependent inhibition of cholera toxin: evidence for toxin internalization and activation through caveolae-like domain. *J. Cell Biol.* 141:905-915.

Paratcha, G., F. Ledda, L. Baars, M. Coulpier, V. Besset, J. Anders, R. Scott, and C. F. Ibanez. 2001. Released GFRalpha 1 potentiates dowstream signaling, neuronal survival, and differenciation via a novel mechanism of recruitment of c-Ret to lipid rafts. *Neuron.* 29:171-184.

Pelkmans, L., J. Kartenbeck, and A. Helenius. 2001. Caveolar endocytosis of simian virus 40 reveals a new two-step vesicular-transport pathway to the ER. *Nat. Cell Biol.* 3:473-483.

Poo, M. M. 2001. Neurotrophins as synaptic modulators. *Nature Rev. Neurosci.* 2:24-32.

Richards, D. A., C. Guatimosim, and W. J. Betz. 2000. Two endocytic recycling routes selectively fill two vesicle pools in frog motor nerve terminals. *Neuron.* 27:551-559.

Sakuma, K., K. Watanabe, M. Sano, I. Uramoto, H. Nakano, Y.-J. Li, S. Kaneda, Y. Sorimachi, K. Yoshimoto, M. Yasuhara, and T. Totsuka. 2001. A possible role for BDNF, NT-4 and TrkB in the spinal cord and muscle of rat subjected to mechanical overload, bupivacaine injection and axotomy. *Brain Res.* 907:1-19.

Schnitzer, J. E., D. P. Mcintosh, A. M. Dvorak, J. Liu, and P. Oh. 1995. Separation of caveolae from associated microdomains of GPI-anchored proteins. *Science.* 269:1435-1439.

Silas-Santiago, I., A. M. Fagan, M. Garber, B. Fritzsch, and M. Barbacid. 1997. Severe sensory deficits but normal CNS development in newborn mice lacking TrkB and TrkC tyrosine protein kinase receptors. *Eur. J. Neurosci.* 9:2045-2056.

Simons, K., and D. Toomre. 2000. Lipid rafts and signal transduction. *Nat. Rev. Mol. Cell Biol.* 1:31-40.

Stoop, R., and M. M. Poo. 1996. Synaptic modulation by neurotrophic factors:differential and synergistic effects of brain-derived neurotrophic factor and ciliary neurotrophic factor. *J. Neurosci.* 16:3256-3264.

Tang, Z. L., P. E. Scherer, T. Okamoto, K. Song, C. Chu, D. S. Kohtz, I. Nishimoto, H. F. Lodish, and M. P. Lisanti. 1996. Molecular cloning of caveolin-3, a novel member of the caveolin gene family expressed predominantly in muscle. *J. Biol. Chem.* 271:2255-2261.

Tansey, M., R. H. Baloh, J. Milbrandt, and E. M. J. Johnson. 2000. GFRα mediated localization of RET to lipid rafts is required for effective downstream signaling, differenciation and neuronal survival. *Neuron.* 25:611-623.

Tao, H. W., and M. M. Poo. 2001. Retrograde signaling at central synapses. *Proc. Natl. Acad. Sci. USA.* 98:11009-11015.

Tsui-Pierchala, B. A., M. Encinas, J. Milbrandt, and E. M. J. Johnson. 2002. Lipid raft in neuronal signaling and function. *Trends Neurosci.* 25:412-417.

Tyler, W. J., and L. D. Pozzo-Miller. 2001. BDNF enhances quantal neurotransmitter release and increases the number of docked vesicles at the active zones of the hippocampal excitatory synapses. *J. Neurosci.* 21:4249-4258.

Vyas. 2001. Segregation of gangliosides GM1 and GD3 on cell membranes, isolated membrane rafts and defined supported lipid monolayers. *Biol. Chem.* 382:241-250.

Wang, X. H., and M. M. Poo. 1997. Potentiation of developing synapses by postsynaptic release of neurotrophin-4. *Neuron.* 19:825-835.

Wolf, A. A., M. G. Jobling, S. Wimer-Mackin, M. Ferguson-Maltzman, J. L. Madara, R. K. Holmes, and W. I. Lencer. 1998. Ganglioside structure dictates signal transduction by cholera toxin and association with caveolae-like membrane domains in polarized epithelia. J. Cell Biol. 141:917-927.

Wu, C., S. Butz, Y. Ying, and R. G. W. Anderson. 1997. Tyrosine kinase receptors concentrated in caveolae-like domains from neuronal plasma membrane. *J. Biol. Chem.* 272:3554-3559.

Xie, K., T. Wang, P. Olafsson, K. Mizuno, and B. Lu. 1997. Activity-dependent expression of NT-3 in muscle cells in culture: implications in the development of neuromuscular junctions. *J. Neurosci.* 17:2947-2958.

Yamashita, T., H. Higuchi, and M. Tohyama. 2002. The p75 receptor transduces the signal from myelin-associated glycoprotein to Rho. *J. Cell Biol.* 157:565-570.

Yan, Q., M. J. Radeke, D. R. Matheson, J. Talvenheimo, A. A. Welcher, and P. Feinstein. 1997. Immunocytochemical localization of trkB in the central nervous system of the adult rat. *J. Comp. Neurol.* 378:135-157.

---

What is claimed is:

1. A method of increasing the transport in a neuron of a tetanus toxin or a fusion protein comprising a fragment C of the tetanus toxin, wherein the method comprises
   a) administering to the neuron a tetanus toxin or a fusion protein comprising a fragment C; and
   b) administering to the neuron a Brain Derived Neurotrophic Factor (BDNF), a Neurotrophin 4 (NT-4), or Glial-Derived Neurotrophic Factor (GDNF) in an amount sufficient to increase the neuronal transport of the tetanus toxin or the fusion protein.

2. The method according to claim 1, wherein the tetanus toxin is administered with Brain Derived Neurotrophic Factor (BDNF).

3. The method according to claim 1, wherein the fusion protein comprising a fragment C of the tetanus toxin is administered with Brain Derived Neurotrophic Factor (BDNF).

4. The method of claim 2 or 3, wherein the BDNF is injected into the Levator auris longus (LAL) muscle.

5. The method of claim 2 or 3, wherein the BDNF is injected into the gastrocnemeius muscle.

6. The method according to claim 1, wherein the tetanus toxin is administered with Neurotrophin 4 (NT-4).

7. The method according to claim 1, wherein the fusion protein comprising a fragment C of the tetanus toxin is administered with Neurotrophin 4 (NT-4).

8. The method of claim 6 or 7, wherein the NT-4 is injected into the Levator auris longus (LAL) muscle.

9. The method of claim 6 or 7, wherein the NT-4 is injected into the gastrocnemeius muscle.

10. The method according to claim 1, wherein the tetanus toxin is administered with Glial-Derived Neurotrophic Factor (GDNF).

11. The method according to claim 1, wherein the fusion protein comprising a fragment C of the tetanus toxin is administered with Glial- Derived Neurotrophic Factor (GDNF).

12. The method of claim 10 or 11, wherein the GDNF is injected into the Levator auris longus (LAL) muscle.

13. The method of claim 10 or 11, wherein the GDNF is injected into the gastrocnemeius muscle.

14. The method of claim 1, wherein the tetanus toxin or a fusion protein comprising a fragment C is administered before, after, or simultaneously with the administration of a Brain Derived Neurotrophic Factor (BDNF), a Neurotrophin 4 (NT-4), or Glial-Derived Neurotrophic Factor (GDNF).

* * * * *

UNITED STATES PATENT AND TRADEMARK OFFICE
CERTIFICATE OF CORRECTION

| | | |
|---|---|---|
| PATENT NO. | : 7,923,216 B2 | Page 1 of 1 |
| APPLICATION NO. | : 10/662808 | |
| DATED | : April 12, 2011 | |
| INVENTOR(S) | : Roux et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1521 days.

Signed and Sealed this
Twenty-second Day of November, 2011

David J. Kappos
*Director of the United States Patent and Trademark Office*